US009404122B2

(12) United States Patent
Yu et al.

(10) Patent No.: US 9,404,122 B2
(45) Date of Patent: Aug. 2, 2016

(54) ENDOTHELIAL CELL PRODUCTION BY PROGRAMMING

(71) Applicant: Cellular Dynamics International, Inc., Madison, WI (US)

(72) Inventors: Junying Yu, Madison, WI (US); Maksym A. Vodyanyk, Madison, WI (US)

(73) Assignee: Cellular Dynamics International, Inc., Madison, WI (US)

( * ) Notice: Subject to any disclaimer, the term of this patent is extended or adjusted under 35 U.S.C. 154(b) by 98 days.

(21) Appl. No.: 14/302,621

(22) Filed: Jun. 12, 2014

(65) Prior Publication Data

US 2014/0349398 A1 Nov. 27, 2014

Related U.S. Application Data

(62) Division of application No. 13/178,239, filed on Jul. 7, 2011, now Pat. No. 8,785,192.

(60) Provisional application No. 61/362,085, filed on Jul. 7, 2010.

(51) Int. Cl.

| | |
|---|---|
| ***C12N 5/00*** | (2006.01) |
| ***C12N 15/85*** | (2006.01) |
| ***C12N 5/071*** | (2010.01) |
| ***G01N 33/50*** | (2006.01) |

(52) U.S. Cl.

CPC ................ *C12N 15/85* (2013.01); *C12N 5/069* (2013.01); *C12N 5/0692* (2013.01); *G01N 33/5064* (2013.01); *C12N 2501/40* (2013.01); *C12N 2506/02* (2013.01); *C12N 2506/45* (2013.01); *G01N 2500/10* (2013.01)

(58) Field of Classification Search

CPC ....... C12N 15/85; C12N 5/069; C12N 5/0692

See application file for complete search history.

(56) References Cited

U.S. PATENT DOCUMENTS

| | | | | |
|---|---|---|---|---|
| 5,486,359 | A | 1/1996 | Caplan et al. | 424/93.7 |
| 5,736,396 | A | 4/1998 | Bruder et al. | 435/366 |
| 5,811,094 | A | 9/1998 | Caplan et al. | 424/93.7 |
| 5,827,735 | A | 10/1998 | Young et al. | 435/325 |
| 5,827,740 | A | 10/1998 | Pittenger | 435/372 |
| 5,837,539 | A | 11/1998 | Caplan et al. | 435/332 |
| 5,837,670 | A | 11/1998 | Hartshorn | 510/490 |
| 6,602,286 | B1 | 8/2003 | Strecker | 623/1.24 |
| 6,833,269 | B2 | 12/2004 | Carpenter | 435/377 |
| 7,015,036 | B2 | 3/2006 | Prachumsri et al. | 435/370 |
| 7,473,555 | B2 | 1/2009 | Mandalam et al. | 435/377 |
| 7,781,214 | B2 | 8/2010 | Smith et al. | 435/377 |
| 2005/0266556 | A1 | 12/2005 | Yoder et al. | 435/372 |
| 2009/0130064 | A1 | 5/2009 | Rogiers et al. | 424/93.7 |
| 2009/0317365 | A1 | 12/2009 | Lee et al. | 424/93.7 |

FOREIGN PATENT DOCUMENTS

| | | |
|---|---|---|
| EP | 0412700 | 2/1991 |
| WO | WO 03/040319 | 5/2003 |
| WO | WO 03/042405 | 5/2003 |
| WO | WO 2008/036209 | 3/2008 |
| WO | WO 2010/014949 | 2/2010 |

OTHER PUBLICATIONS

"ERG v-ets erythroblastosis virus E26 oncogene homolog (avian) [*Homo sapiens*]" Gene ID: 2078. Entrez Gene. Updated May 29, 2010.

Amit et al., "Clonally derived human embryonic stem cell lines maintain pluripotency and proliferative potential for prolonged periods of culture," *Dev. Bio.*, 227:271-278, 2000.

Bailey et al., "Transplanted adult hematopoietic stem cells differentiate into functional endothelial cells," *Blood*, 103(1):13-19, 2004.

Bhatia et al., "Bone morphogenetic proteins regulate the developmental program of human hematopoietic stem cells," *J. Exp. Med.*, 189:1139-1148, 1999.

Boyer et al., "Core transcriptional regulatory circuitry in human embryonic stem cells," *Cell*, 122(6):947-56, 2005.

Chadwick et al.., "Cytokines and BMP-4 promote hematopoietic differentiation of human embryonic stem cells," *Blood*, 102(3):906-915, 2003.

Chambers et al., "Functional expression cloning of Nanog, a pluripotency sustaining factor in embryonic stem cells," *Cell*, 113(5):643-55, 2003.

David et al., "Forward programming of pluripotent stem cells towards distinct cardiovascular cell types," Cardiovascular Research, 84:263-272, 2009.

De Val and Black, "Transcriptional control of endothelial cell development," *Developmental Cell*, 16:180-195, 2009.

Dzau et al., "Therapeutic potential of endothelial progenitor cells in cardiovascular diseases," *Hypertension*, 46-7-18, 2005.

Extended European Search Report issued in European Application No. 11804353.8, mailed Dec. 10, 2013.

Extended European Search Report issued in European Application No. 11769522.1, mailed Feb. 3, 2014.

Genbank Accession No. NM 000545.4 "*Homo sapiens* HNF-1A homeobox a (HNF1A), mRNA", 1990.

Genbank Accession No. NM_000457.3 "*Homo sapiens* hepatocyte nuclear factor 4, alpha (HNF4A), transcript variant 2, mRNA," 1994.

Genbank Accession No. NM_005996.3, "*Homo sapiens* T-box 3 (TBX3), transcript variant 1, mRNA," 1997.

Genbank Accession No. NM_153675.2, "*Homo sapiens* forkhead box A2 (FOXA2), transcript variant 2, mRNA," 1997.

Genbank Accession No. NM_178849.1, "*Homo sapiens* hepatocyte nuclear factor 4, alpha (HNF4A), transcript variant 1, mRNA" 1994.

Genbank Accession No. NM_178850.1, "*Homo sapiens* hepatocyte nuclear factor 4, alpha (HNF4A), transcript variant 3, mRNA," 1994.

(Continued)

*Primary Examiner* — Marcia S Noble

(74) *Attorney, Agent, or Firm* — Parker Highlander PLLC

(57) ABSTRACT

The invention generally regards methods for providing endothelial cells and precursors of endothelial cells from a variety of cell sources, such as pluripotent stem cells. Also provided are therapeutic compositions including the provided endothelial cells, and methods of using them for the treatment of subjects.

7 Claims, 19 Drawing Sheets

(56) References Cited

OTHER PUBLICATIONS

Genbank Accession No. NM_001030003.1, "*Homo sapiens* hepatocyte nuclear factor 4, alpha (HNF4A), transcript variant 5, mRNA," 1994.
Genbank Accession No. NM_001030004.1, "*Homo sapiens* hepatocyte nuclear factor 4, alpha (HNF4A), transcript variant 6, mRNA," 1994.
Harding and Gibson, "Therapeutic liver repopulation for phenylketonuria," *J Inherit Metab Dis*, 33:681-687, 2010.
Hayhurst et al., "Hepatocyte nuclear factor 4alpha (nuclear receptor 2A1) is essential for maintenance of hepatic gene expression and lipid homeostasis," *Mol. Cell Biol.*, 21(4):1393-403, 2001.
Huang et al., "Induction of functional hepatocyte-like cells from mouse fibroblasts by defined factors," Nature, 475(7356):386-389, 2011.
Huber et al., "Cooperative effects of growth factors involved in the induction of hematopoietic mesoderm," *Blood*, 92: 4128-4137, 1998.
Ishizaka et al., "Development of hepatocytes from embryonic stem cells after transfection with the HNF-3β gene," *The FASEB Journal* express article, doi:10.1096/fj.01-0806fje. Published online Jul. 1, 2002.
Ishizaka et al., "Development of hepatocytes from ES cells after transfection with the HNF-3β gene," *FASEB J.*, 16(11):1444-1446, 2002.
Kanda et al., "In vitro differentiation of hepatocyte-like cells from embryonic stem cells promoted by gene transfer of hepatocyte nuclear factor 3 β," *Hepatology Research*, 26:225-231, 2003.
Kheolamai and Dickson, "Liver-enriched transcription factors are critical for the expression of hepatocyte marker genes in mES-derived hepatocyte-lineage cells," *BMC Molecular Biology*, 10:35, doi:10 .11861/1471-2199-10-35, 2009.
Khurana et al., "Hepatocyte nuclear factor-4α induces transdifferentiation of hematopoietic cells into hepatocytes," *Journal of Biological Chemistry*, 285(7):4725-4731, 2010.
Kubo et al., "The homeobox gene Hex regulates hepatocyte differentiation from embryonic stem cell-derived endoderm," *Hepatology*, 51:633-641, 2010.
Kuzuya et al., "VEGF protects against oxidized LDL toxicity to endothelial cells by an intracellular glutathione-dependent mechanism through the KDR receptor," *Arterioscl., Thromb. Vascular Biol.*, 21:765-70, 2001.
Kweon et al., "ER71 regulates endothelial and hematopoietic cell development during embryogenesis," Abstract, *Circulation*, 122:A18885, 2010.
Lavon et al., "Differentiation and isolation of hepatic-like cells from human embryonic stem cells," *Differentiation*, 72:230-238, 2004.
Lavon et al., "Study of hepatocyte differentiation using embryonic stem cells," *Journal of Cellular Biochemistry*, 96:1193-1202, 2005.
Lee et al., "ER71 acts downstream of BMP, notch, and Wnt signaling in blood and vessel progenitor specification," *Cell Stem Cell*, 2:497-507, 2008.
Levinson-Dushnik et al., "Involvement of hepatocyte nuclear factor 3 in endoderm differentiation of embryonic stem cells," *Molecular and Cellular Biology*, 17(7):3817-3822, 1997.
Li et al., "Mammalian hepatocyte differentiation requires the transcription factor HNF-4alpha," *Genes Dev.*, 14(4):464-74, 2000.
Li et al., "Transplantation of human embryonic stem cell-derived endothelial cells for vascular diseases," *J. Cell Biochem.*, 106:194-199, 2009.
Marshall et al., "Polarized expression of bone morphogenetic protein-4 in the human aorta-gonad-mesonephros region," *Blood*, 96:1591-1593, 2000.
Nagaki and Moriwaki, "Transcription factor HNF and hepatocyte differentiation," *Hepatology Research*, 38:961-969, 2008.
Nikolova-Krstevski et al., "ERG is required for the differentiation of embryonic stem cells along the endothelial lineage," *BMC Developmental Biology*, 9:72, 2009.
Office Action issued in U.S. Appl. No. 13/086,159, mailed Aug. 17, 2012.
Office Action issued in U.S. Appl. No. 13/086,159, mailed Oct. 10, 2012.
Office Action issued in U.S. Appl. No. 13/178,239, mailed Aug. 6, 2013.
Office Action issued in U.S. Appl. No. 13/178,239, mailed Jan. 13, 2014.
Office Action issued in U.S. Appl. No. 13/178,239, mailed Mar. 7, 2013.
PCT International Preliminary Report on Patentability issued in International Application No. PCT/US2011/043218, mailed Jan. 17, 2013.
PCT International Preliminary Report on Patentability issued in International Application No. PCT/US2011/032309, mailed Oct. 26, 2012.
PCT International Search Report and Written Opinion issued in International application No. PCT/US2011/032309, dated Dec. 9, 2011.
PCT International Search Report and Written Opinion issued in International application No. PCT/US2001/043218, dated Feb. 17, 2012.
Ria et al., "Endothelial differentiation of hematopoietic stem and progenitor cells from patients with multiple myeloma," *Clinical Cancer Research*, 14:1678-1685, 2008.
Sekiya and Suzuki, "Direct conversion of mouse fibroblasts to hepatocyte-like cells by defined factors," Nature, 475(7356):390-393, 2011.
Si-Tayeb et al., "Highly efficient generation of human hepatocyte-like cells from induced pluripotent stem cells," *Hepatology*, 51(1):297-305, 2010.
Snykers et al., "In vitro differentiation of embryonic and adult stem cells into hepatocytes: state of the art," *Stem Cells*, 27:577-605, 2009.
Sullivan et al., "Generation of functional human hepatic endoderm from human induced pluripotent stem cells," *Hepatology*, 51(1):329-335, 2010.
Sumanas et al., "Interplay among Etsrp/ER71, Scl, and ALK8 signaling controls endothelial and myeloid cell formation," *Blood*, 111(9):4500-4510, 2008.
Takahashi and Yamanaka, "Induction of pluripotent stem cells from mouse embryonic and adult fibroblast cultures by defined factors," *Cell*, 126(4):663-676, 2006.
Takahashi et al., "Induction of pluripotent stem cells from adult human fibroblasts by defined factors," *Cell*, 131:861-872, 2007.
Thomson et al. "Isolation of a primate embryonic stem cell line," *Proc. Natl. Acad. Scie. USA*, 92:7844-7848, 1995.
Thomson et al., "Embryonic stem cell lines derived from human blastocysts," *Science*, 282:1145, 1998.
U.S. Appl. No. 61/058,858 entitled Methods for the Production of iPS Cells Using Non Viral Approach, by Amanda Mack, filed Jun. 4, 2008.
U.S. Appl. No. 61/184,546 entitled "Reprogramming T Cells," by Matthew Brown et al., filed Jun. 5, 2009.
Watt et al., "HNF4: A central regulator of hepatocyte differentiation and function," *Hepatology*, 37(6): 1249-1253, 2003.
Wong et al., "Identification of vasculature-specific genes by microarray analysis of Etsrp/Etv2 overexpressing zebrafish embryos," *Developmental Dynamics*, 238(7):1836-1850, 2009.
Yu and Thompson, "Pluripotent stem cell lines," *Genes Dev.*, 22(15):1987-97, 2008.
Yu et al., "Human induced pluripotent stem cells free of vector and transgene sequences," *Science*, 324(5928):797-801, 2009.
Yu et al., *Science*, "Induced pluripotent stem cell lines derived from human somatic cells," 318(5858):1917-1920, 2007.
Zhao et al., "Derivation and characterization of hepatic progintor cells from human embryonic stem cells," *PLoSONE*, 4(7):e6468, pp. 1010, 2009.

ENDOTHELIAL CELL PRODUCTION BY PROGRAMMING

This application is a divisional of U.S. application Ser. No. 13/178,239, filed Jul. 7, 2011, which claims benefit of priority to U.S. Provisional Application No. 61/362,085, filed Jul. 7, 2010, the entire contents of each of which are specifically incorporated herein by reference without disclaimer.

BACKGROUND OF THE INVENTION

1. Field of the Invention

The present invention relates generally to the field of molecular biology, stem cells, and differentiated cells. More particularly, it concerns programming of somatic cells and undifferentiated cells toward specific cell lineages, particularly endothelial cells and precursors of endothelial cells, such as endothelial progenitor cells.

2. Description of Related Art

Endothelial cells and precursors of endothelial cells have many potential therapeutic uses, including treatment of tissue ischemia—e.g., as occurs in atherosclerosis, myocardial infarction, and limb ischemia—repair of injured blood vessels, and bioengineering of grafts. Preliminary studies have shown that transplantation of endothelial progenitor cells (EPCs) may be useful in treating ischemia in patients with myocardial infarction or limb ischemia (Dzau et al., 2005). However, the clinical usefulness of EPCs obtained from patients is limited because patients in need of endothelial cell therapies often produce too few EPCs or EPCs that are functionally deficient.

In addition to such clinical applications, endothelial cells are in high demand for use in screening compounds and drugs for vascular toxicity, vascular permeability, and anti-cancer activity. However, primary endothelial cells have a finite proliferative potential due to their age, donor, and organ-type specific variations, all of which limit the ability to standardize endothelial cell culture protocols and to expand these cells in sufficient numbers for drug-screening purposes.

Endothelial cells may also be obtained from human embryonic stem cells (ESCs) or induced pluripotent stem cells (iPSCs), both of which are capable of unlimited proliferation in vivo and retain their potential to differentiate into all somatic cell types. Differentiation of human ESCs or iPSCs into cells of endothelial lineage in vitro recapitulates normal in vivo development and includes stages of mesoderm induction and specification of angiogenic mesodermal precursors. The process requires the addition of specific inductive factors. Endothelial cells derived from human ESCs or iPSCs are functional in in vitro assays and capable of transplantation in vivo (Li et al., 2009). However, differentiation of endothelial cells from human ESCs or iPSCs is an inefficient process.

Therefore, there is a need for efficient production of endothelial cells and endothelial cell precursors for therapeutic and research uses.

SUMMARY OF THE INVENTION

The present invention overcomes a major deficiency in the art in providing endothelial cells and precursors of endothelial cells by forward programming or transdifferentiation to provide an unlimited supply of endothelial cells or precursors of endothelial cells. The methods may be particularly useful in providing an unlimited supply of patient-specific endothelial cells.

Methods disclosed herein provide endothelial cells or endothelial precursor cells by programming a variety of cell types. In certain aspects, programming methods include culturing pluripotent stem cells or somatic cells under conditions that increase the expression level of one or more genes that, when expressed alone or in combination with other programming factor genes, are capable of promoting programming to the endothelial lineage. Such genes are termed "endothelial programming factor genes." Endothelial programming factor genes useful in the invention may include any genes that, alone or in combination, directly impose endothelial fate upon non-endothelial cells and may include transcription factor genes or other genes that are important in endothelial cell differentiation or function. The process of programming alters the type of progeny a cell can produce and includes the distinct processes of forward programming and transdifferentiation. In some embodiments, forward programming of multipotent cells or pluripotent cells provides endothelial cells or endothelial precursor cells. In other embodiments, transdifferentiation of non-endothelial somatic cells provides endothelial cells or endothelial precursor cells. In certain aspects, programming may comprise increasing the expression level of a sufficient number of endothelial programming factor genes to cause forward programming or transdifferentiation of non-endothelial cells to endothelial precursor cells or endothelial cells. Sources of cells suitable for endothelial programming may include any stem cells or non-endothelial cell somatic cells. For example, the stem cells may be pluripotent stem cells or any non-pluripotent stem cells. As used herein, a "pluripotent cell" or "pluripotent stem cell" is a cell that has the capacity to differentiate into essentially any fetal or adult cell type. Exemplary types of pluripotent stem cells may include, but are not limited to, embryonic stem cells and induced pluripotent stem cells (or iPS cells). Such a pluripotent stem cell may be a mammalian pluripotent stem cell. In certain embodiments, the pluripotent stem cell is a human pluripotent stem cell. Sources of cells suitable for programming of endothelial precursors or endothelial cells by transdifferentiation may include any non-endothelial somatic cells. Such somatic cells may be any cells forming the body of an organism. In a particular aspect, the somatic cells may be immortalized to provide an unlimited supply of cells, for example, by increasing the level of telomerase reverse transcriptase (TERT). For example, the level of TERT can be increased by increasing the transcription of TERT from the endogenous gene, or by introducing a transgene through any gene delivery method or system.

Pluripotent stem cells useful in the invention may be induced pluripotent stem cells, embryonic stem cells, or pluripotent stem cells derived by nuclear transfer or cell fusion. The stem cells may also include multipotent stem cells, oligopotent stem cells, or unipotent stem cells. The stem cells may also include fetal stem cells or adult stem cells, such as hematopoietic stem cells, mesenchymal stem cells, neural stem cells, epithelial stem cells, or skin stem cells. In certain aspects, the stem cells may be isolated from umbilical tissue, placenta, amniotic fluid, chorion villi, blastocysts, bone marrow, adipose tissue, brain, peripheral blood, cord blood, menstrual blood, blood vessels, skeletal muscle, skin or liver.

A "progenitor cell" or "precursor cell" refers to a lineage-committed cell derived from a pluripotent stem cell. Thus, progenitor cells or precursor cells are more differentiated than pluripotent stem cells, but still have the capacity to differentiate into more than one type of cell. Endothelial cells provided by methods disclosed here may be mature endothelial cells. In other embodiments, the disclosed methods provide endothelial progenitor cells or endothelial precursor cells. Such cells are more differentiated than pluripotent stem cells but are capable of differentiating into endothelial cells or into other types of cells. In some aspects, the disclosed methods provide hematoendothelial (or hemangioblast) progenitor cells, which are capable of differentiating into hematopoietic cells or endothelial cells. In yet other embodiments, methods are provided for differentiating endothelial progenitor cells or endothelial precursor cells into endothelial cells by forward programming.

In certain embodiments, endothelial cells or endothelial precursor cells are provided by forward programming of pluripotent stem cells or transdifferentiation of somatic cells. Such a method may comprise providing the endothelial cells or endothelial precursor cells by culturing the pluripotent stem cells or somatic cells under conditions to increase the expression level of one or more endothelial programming factor genes capable of causing forward programming of the pluripotent stem cells or transdifferentiation of the somatic cells into endothelial cells or endothelial precursor cells, thereby forward programming the pluripotent stem cells or transdifferentiating the somatic cells into endothelial cells or endothelial precursor cells.

As a skilled artisan would understand, methods for increasing the expression of the endothelial programming factor genes in the cells to be programmed may include any method known in the art, for example, by induction of expression of one or more expression cassettes previously introduced into the cells, or by introduction of nucleic acids such as DNA or RNA, polypeptides, or small molecules to the cells. Increasing the expression of certain endogenous but transcriptionally repressed programming factor genes may also comprise reversing the silencing or inhibitory effect on the expression of these programming factor genes by regulating the upstream transcription factor expression or epigenetic modulation.

In certain aspects, endothelial cells or endothelial precursor cells are provided by forward programming of pluripotent stem cells. Such pluripotent stem cells may be induced pluripotent stem cells. In other aspects, endothelial cells or endothelial precursor cells are provided by transdifferentiation of somatic cells. In some embodiments, the somatic cells are human somatic cells such as skin fibroblasts, adipose tissue-derived cells, keratinocytes, or blood cells. Somatic cells useful for transdifferentiation may be immortalized somatic cells. In a particular aspect, the somatic cells may be immortalized to provide an unlimited supply of cells, for example, by increasing the level of telomerase reverse transcriptase (TERT). For example, the level of TERT can be increased by increasing the transcription of TERT from the endogenous gene, or by introducing a transgene through any gene delivery method or system.

Endothelial cells or endothelial precursor cells may be provided by forward programming of pluripotent stem cells or transdifferentiation of somatic cells that comprise at least one exogenous expression cassette. The expression cassette may comprise one or more endothelial programming factor genes. In some aspects, pluripotent stem cells or somatic cells are contacted with one or more such endothelial programming factors comprising gene products of the one or more endothelial programming factor genes in an amount sufficient to cause forward programming of the pluripotent cells or transdifferentiation of the somatic cells into endothelial cells or endothelial precursor cells. In some embodiments, the one or more gene products are polypeptide products of one or more endothelial programming factor genes. In certain aspects, the one or more endothelial programming factors include a protein transduction domain to facilitate intracellular entry of polypeptides of the endothelial programming factor genes. Such protein transduction domains are well known in the art, such as an HIV TAT protein transduction domain, HSV VP22 protein transduction domain, *Drosophila* Antennapedia homeodomain, or variants thereof. In other embodiments, the one or more gene products are RNA transcripts of one or more endothelial programming factor genes.

Endothelial programming factor genes useful in the invention may include any genes that, alone or in combination, directly impose endothelial fate upon non-endothelial cells, especially transcription factor genes or genes that are important in endothelial cell differentiation or endothelial cell function when expressed in cells. Endothelial cell programming factor genes include, but are not limited to v-ets erythroblastosis virus E26 oncogene homolog (avian) (ERG), v-ets erythroblastosis virus E26 oncogene homolog 1 (avian) (ETS1), v-ets erythroblastosis virus E26 oncogene homolog 2 (avian) (ETS2), ELF-1, ELF-4, FLI-1, TEL, ETV2 (ets variant 2, ER71, or Etsrp71), TAL1 (SCL), GATA2, or the Forkhead (FOX) transcription factors (e.g., FoxC, FoxF, FoxH, and FoxO families). For example, one, two, three, four, five, six, seven, eight, nine, ten, or more of these exemplary genes, isoforms of such genes, or variants thereof may be used in certain aspects of the invention. Many of these genes have different isoforms, which may have similar functions and thus are contemplated for use in certain aspects of the invention.

In particular aspects, the endothelial programming factor gene is ERG. In certain embodiments, the endothelial programming factor gene is ERG isoform 3 (ERG-3); however, the programming factor gene may be any isoform of ERG, including ERG isoform 1 (ERG-1), ERG isoform 2 (ERG-2), and ERG isoform 4 (ERG-4). In yet other particular embodiments, the endothelial programming factor gene is ETV2.

"Forward programming," as used herein, refers to a process having essentially no requirement to culture cells through intermediate cellular stages using culture conditions that are adapted for each such stage and/or, optionally, having no need to add different growth factors during different time points between the starting cell source and the desired end cell product, e.g., endothelial cells or endothelial cell precursors, as exemplified in the upper part of FIG. 1. On the other hand, the bottom part of FIG. 1 demonstrates various developmental stages present in a step-wise differentiation process and the need to add different growth factors at different times during the process, which involves more labor, time, and expense than methods described in certain aspects of the current invention. Therefore, the methods of forward programming in certain aspects of the present invention are advantageous by avoiding the need to add different growth factors at different stages of programming or differentiation to improve efficiency.

In certain aspects, the cells for endothelial cell or endothelial precursor programming, such as, for example, pluripotent stem cells or somatic cells, comprise at least one exogenous expression cassette, wherein the expression cassette comprises one or more endothelial programming factor genes. One or more expression cassettes may drive expression of one or more endothelial programming factor genes in an amount sufficient to cause forward programming of pluripotent cells into endothelial cells or transdifferentiation of somatic cells into endothelial cells. In certain embodiments, one or more expression cassettes drive expression of v-ets erythroblastosis virus E26 oncogene homolog (avian) (ERG). In other certain aspects, one or more expression cassettes may drive expression of ETV2. Alternatively, the expression of one or more endothelial programming factor genes may be increased without the use of an expression cassette.

In methods utilizing one or more exogenous expression cassettes, such an expression cassette may include an externally inducible transcriptional regulatory element for inducible expression of one or more endothelial programming factor genes. For example, an exogenous expression cassette useful in the invention may contain an inducible promoter, such as a promoter that includes a tetracycline response element. In some embodiments, the exogenous expression cassette is comprised in a gene delivery system. For example, such a gene delivery system may be a transposon system, a viral gene delivery system, or an episomal gene delivery system. A viral gene delivery system useful in the invention may be an RNA-based or DNA-based viral vector. An episomal gene delivery system useful in the invention may be a plasmid, an Epstein-Ban virus (EBV)-based episomal vector, a yeast-based vector, an adenovirus-based vector, a simian virus 40 (SV40)-based episomal vector, a bovine papilloma virus (BPV)-based vector, or the like. In certain aspects, an expression cassette for use in forward programming or transdifferentiation may include an endothelial-specific transcriptional regulatory element operably linked to a reporter gene.

In certain methods, cells for endothelial cell programming, such as pluripotent stem cells, are contacted with one or more endothelial programming factors in an amount sufficient to cause forward programming of the cells into endothelial cells. Endothelial programming factors include endothelial programming factor genes, products of such genes, or fragments of products of such genes. Endothelial programming factors may be gene products of one or more endothelial programming factor genes. For example, the one or more gene products may be polypeptides of one or more endothelial programming factor genes or fragments of polypeptides of one or more endothelial programming factor genes. In particular embodiments, an endothelial programming factor is a product of the ERG gene (including any isoform thereof), ETS1 gene, ETS2 gene, ELF-1 gene, ELF-4 gene, FLI-1 gene, TEL gene, ETV2 (ER71 or Etsrp71) gene, TAL1 (SCL) gene, GATA2 gene, or a Forkhead (FOX) transcription factor gene (e.g., a member of the FoxC, FoxF, FoxH, or FoxO family).

In some embodiments, methods of providing endothelial cells or endothelial precursor cells by forward programming of pluripotent stem cells or transdifferentiation of somatic cells are provided wherein the pluripotent stem cells, somatic cells, or progeny cells of pluripotent stem cells or somatic cells contain a reporter expression cassette. Such an expression cassette may comprise an endothelial programming factor gene. In certain embodiments, such an expression cassette may comprise an endothelial cell-specific transcriptional regulatory element operably linked to a reporter gene. In particular embodiments, an endothelial cell-specific promoter may be operably linked to a reporter. For example, the promoter of FLT-1, von Willebrand factor (vWF), or TIE1 may be operably linked to a reporter in an expression cassette in some embodiments.

Endothelial cells or endothelial precursor cells generated by any of the methods provided here may have one or more characteristics of endothelial cells. For example, such endothelial cells may express one or more endothelial cell markers. Endothelial cell markers include, but are not limited to, VE-cadherin (CD144), ACE (angiotensin-converting enzyme) (CD143), BNH9/BNF13, CD31, CD34, CD54 (ICAM-1), CD62E (E-Selectin), CD105 (Endoglin), CD146, Endocan (also called ESM-1), Endoglyx-1, Endomucin, Eotaxin-3, EPAS1 (Endothelial PAS domain protein 1), Factor VIII related antigen, FLI-1, Flk-1 (KDR, VEGFR-2), FLT-1 (VEGFR-1), GATA2, GBP-1 (guanylate-binding protein-1), GRO-alpha, HEX, ICAM-2 (intercellular adhesion molecule 2), LMO2, LYVE-1, MRB (magic roundabout), Nucleolin, PAL-E (pathologische anatomie Leiden-endothelium), RTKs, sVCAM-1, TAL1, TEM1 (Tumor endothelial marker 1), TEM5 (Tumor endothelial marker 5), TEM7 (Tumor endothelial marker 7), Thrombomodulin (TM, CD141), VCAM-1 (vascular cell adhesion molecule-1) (CD106), VEGF (Vascular endothelial growth factor), vWF (von Willebrand factor, also called Factor VIII), ZO-1, endothelial cell-selective adhesion molecule (ESAM), CD102, CD93, CD184, CD304, and DLL4. In particular embodiments, an endothelial cell marker useful in the invention is one or more of CD144, CD31, CD34, ESAM, CD102, CD143, CD93, CD184, CD105, CD146, von Willebrand factor, ZO-1, CD304, and DLL4. In some embodiments, the endothelial cells produced by forward programming or transdifferentiation do not express certain markers or exhibit decreased expression of certain markers, such as markers of mesenchymal cells (e.g., CD140a, CD140b), markers of hematopoietic cells (e.g., CD43, CD45, CD235a, or CD41a) or markers of human pluripotent stem cells (e.g., TRA1-60).

Other characteristics of endothelial cells useful in the invention are functional characteristics of endothelial cells. For example, one such functional characteristic is the ability to take up acetylated low density lipoprotein (ac-LDL). Yet another functional characteristic of endothelial cells is the ability to form tube-like structures in a three dimensional matrix, such as matrigel. An additional functional characteristic of endothelial cells is barrier function. Another characteristic of endothelial cells useful in the invention is the ability to respond to one or more pro-inflammatory stimuli (e.g., TNF, and IL-1) by upregulating the expression of cell-adhesion molecules (e.g., CD54 (ICAM-1), CD106, and CD62E). Yet another characteristic of endothelial cells useful in the invention is the expression of tight junction proteins (e.g., Claudin 5 and ZO-1). Other additional characteristics of endothelial cells useful in the invention are morphological features, such as a flattened (or squamous) appearance and a large, central nucleus.

In certain embodiments, methods may further include one or more steps that select or enrich for endothelial cells. For example, the selected or enriched endothelial cells may express a reporter gene that is operably linked to an endothelial cell-specific transcriptional regulatory element. In other embodiments, the selected or enriched endothelial cells may exhibit one or more endothelial cell characteristics. For example, the selected or enriched endothelial cells may express one or more endothelial cell markers, exhibit one or more functional characteristics of endothelial cells, or exhibit one or more morphological characteristics of endothelial cells.

In certain embodiments, pluripotent stem cells used in methods disclosed here are cultured in a medium that contains one or more growth factors. For example, the medium may contain basic FGF, VEGF, or both. Such culturing may be prior to, during, or after the increased expression of endothelial programming factors.

Endothelial cells provided by methods disclosed herein may be provided at least, about or up to 3, 4, 5, 6, 7, 8, 9, 10, 11, 12, 13, 14, 15, 16, 17, 18, 19, 20 days (or any range derivable therein) after the increased expression or culturing in the presence or absence of growth factors. In some particular methods, the provided endothelial cells are obtained after up to 10 days of the increased expression of one or more endothelial programming factor genes. In other embodiments, the provided endothelial cells are obtained after up to 4 days of the increased expression.

In certain aspects, the methods include one or more additional steps wherein cell groupings are dispersed into essentially individual cells. The dispersing may be performed, for example, at least about 24 hours after the increased expression. In some embodiments, the dispersing is performed at least 1, 2, 3, 4, or more days after the increased expression. The methods may also include one or more steps wherein the essentially individual cells are dispersed onto a surface coated with a matrix component. For example, the surface may be coated with fibronectin, gelatin, collagen, poly-d-lysine, matrigel, or an RGD peptide. Cells plated onto a surface coated with a matrix component may be cultured. In some embodiments, cells plated onto a surface coated with a matrix component are cultured for at least about 12 hours. After the culturing, unattached cells may be removed, and the attached cells may be further cultured. For example, the attached cells may be further cultured for at least two days.

Dispersing of cell groupings may be performed by mechanical or enzymatic means. For example, the cells may be dispersed by treatment with an effective amount of one or more enzymes, such as trypsin or trypLE, or a mixture of enzymes such as Accutase®. Dispersed cells may be cultured in a medium comprising one or more growth factors. For example, the dispersed cells may be cultured in a medium that contains basic FGF, VEGF, or both.

Also provided are methods of providing endothelial progenitor cells by forward programming of pluripotent stem cells or transdifferentiation of somatic cells. In such methods, the endothelial progenitor cells may be provided by culturing pluripotent stem cells or somatic cells under conditions to increase the expression level of one or more endothelial programming factor genes capable of causing forward programming of the pluripotent cells or transdifferentiation of the somatic cells into endothelial progenitor cells, thereby forward programming the pluripotent stem cells into endothelial progenitor cells or transdifferentiating the somatic cells into endothelial progenitor cells.

Methods of providing arterial endothelial cells are also provided. In some aspects, the method includes increasing the expression of one or more endothelial programming factors such as, for example ERG or ETV2. In certain embodiments, the arterial endothelial cells express one or more arterial endothelial cells markers such as, for example, CD304, CD184, or DLL4.

In certain aspects, methods of providing hemogenic endothelial cells are provided. In some aspects, the hemogenic endothelial cells are provided by increasing expression of an endothelial programming factor, such as, for example, ETV2. Such hemogenic endothelial cells may be used to generate hematopoietic cells when cultured in a hematopoietic culture medium. The hematopoietic culture medium may be any medium suitable for generating hematopoietic cells. For example, the hematopoietic culture medium may include one or more components selected from the group consisting of ESFM, StemLine HSC medium (Sigma), fibroblast growth factor (FGF), vascular endothelial growth factor (VEGF), stem cell factor (SCF), thrombopoietin (TPO), interleukin-3 (IL-3), and interleukin-6 (IL-6). In particular embodiments, the hematopoietic culture medium includes ESFM, StemLine HSC medium (Sigma), FGF, VEGF, SCF, TPO, IL-3, and IL-6. The generated hematopoietic cells may comprise one or more hematopoietic cell markers selected from the group consisting of CD43, CD45, CD235a, and CD41a. In certain aspects, the hematopoietic cells are CD43+, CD45+, CD235a+ and/or CD41a+.

In other aspects, methods of providing mesenchymogenic endothelial cells are provided. In some aspects, the mesenchymogenic endothelial cells are provided by increasing expression of an endothelial programming factor, such as ERG or ETV2. In particular embodiments, the mesenchymogenic endothelial cells are provided by increasing expression of ERG. Such mesenchymogenic endothelial cells may be used to generate mesenchymal cells when cultured in a mesenchymal culture medium. The mesenchymal culture medium may be any medium suitable for generating mesenchymal cells. For example, the mesenchymal culture medium may include one or more components selected from the group consisting of FGF and a TGF-beta inhibitor such as, for example, A83-01. In particular embodiments, the mesenchymal culture medium includes FGF and A83-01. The generated mesenchymal cells may comprise one or more mesenchymal cell markers selected from the group consisting of CD73 and CD105. In some aspects, the generated mesenchymal cells are CD31-CD73+CD105+.

The endothelial cells, endothelial progenitor cells, or precursors of endothelial cells provided herein may be used in any methods and applications currently known in the art for endothelial cells, such as clinical or screening applications. For example, the invention provides methods of assessing a compound for an effect on an endothelial cell. In such methods, an endothelial cell, which may be provided by any method disclosed here, may be contacted with a compound, and the effect of the compound on the endothelial cell may be assayed. For example, a pharmacological or toxicological effect on the endothelial cell may be assayed. In certain embodiments, endothelial cells of the invention are used to assess drug vascular toxicity or vascular permeability. In other embodiments, endothelial cells of the invention are used for development of anti-cancer drugs. Arterial endothelial cells may be used to study diseases such as thrombosis, atherosclerosis, and hypertension.

In some aspects, methods of treating a subject are provided. For example, the subject may have, or is at risk for, a cardiovascular disease or a cardiovascular injury. In some embodiments, the subject has, or is at risk for, ischemia. In yet other embodiments, the subject has a tissue injury or is in need of a tissue graft. In certain aspects, any such subject is treated by administering to the subject a therapeutically effective amount of endothelial cells or endothelial progenitor cells that are provided by any method disclosed herein. In addition, in some embodiments, endothelial cells provided by methods of the invention may be used to bioengineer a tissue graft that is administered to a patient in need of such therapy. In some embodiments, arterial endothelial cells are used in methods of treatment, such as in methods of treating arterial insults, injuries, or diseases.

In certain embodiments, the invention is directed to an endothelial cell or endothelial precursor cell. Such an endothelial cell or endothelial precursor may be provided by a process in accordance with any of the methods disclosed herein. In other certain embodiments, the invention is directed to an endothelial progenitor cell or endothelial precursor cell. Such endothelial progenitor cells or precursor cells may be provided by a process in accordance with any of the methods disclosed herein.

In yet other embodiments, a cell population is provided. Such a cell population may comprise pluripotent stem cells, somatic cells, endothelial cells, endothelial progenitor cells, other precursors of endothelial cells, stem cells, or progeny of any of these. For example, the cell population may consist of endothelial cells, wherein at least 1, 5, 10, 15, 20, 25, 30, 35, 40, 45, 50, 60, 70, 80, 90, 99% or more of the endothelial cells, or any range derivable therein, carry an exogenous expression cassette that includes one or more endothelial programming factor genes. In particular embodiments, 80% of the endothelial cells carry an exogenous expression cassette that includes one or more endothelial programming factor genes. In other aspects, the cell population may consist of endothelial progenitor cells, wherein at least 80% of the endothelial progenitor cells carry an exogenous expression cassette that includes one or more endothelial programming factor genes. In yet other aspects, a cell population is provided that contains pluripotent stem cells or somatic cells where 15, 20, 25, 30, 35, 40, 45, 50, 60, 70, 80, 90, 99% or more of the cells, or any range derivable therein, carry an exogenous expression cassette that includes one or more endothelial programming factor genes. For example, the endothelial programming factor gene may be ERG or ETV2.

Also provided is a composition comprising a cell population comprising two cell types, i.e., the cells to be programmed to endothelial cells and endothelial cells, and essentially free of other intermediate cell types. For example, such a cell population may have two cell types including stem cells and endothelial cells, but essentially free of other cell types in the intermediate developmental stages along the endothelial cell differentiation process. In particular, a composition comprising a cell population consisting of stem cells and endothelial cells may be provided. The stem cells may be particularly pluripotent stem cells, e.g., induced pluripotent stem cells. Endothelial cells may be at least, about, or up to 1, 5, 10, 15, 20, 25, 30, 35, 40, 45, 50, 60, 70, 80, 90, 99% of the cell population, or any range derivable therein.

In certain embodiments, endothelial cells are provided by forward programming of endothelial progenitor cells. For example, the endothelial progenitor cells may be cultured under conditions to increase the expression level of one or more endothelial programming factor genes, such as those described herein, capable of causing forward programming of the endothelial progenitor cells into endothelial cells, thereby forward programming the progenitor cells into endothelial cells. In other embodiments, endothelial cells are provided by transdifferentiation of non-endothelial immortalized somatic cells. For example, the non-endothelial immortalized somatic cells may be cultured under conditions to increase the expression level of one or more endothelial programming factor genes, such as those described herein, capable of causing transdifferentiation of the somatic cells to endothelial cells, thereby transdifferentiating the somatic cells into endothelial cells.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms “encode” or “encoding” with reference to a nucleic acid are used to make the invention readily understandable by the skilled artisan however these terms may be used interchangeably with “comprise” or “comprising” respectively.

As used herein the specification, “a” or “an” may mean one or more. As used herein in the claim(s), when used in conjunction with the word “comprising,” the words “a” or “an” may mean one or more than one.

The use of the term “or” in the claims is used to mean “and/or” unless explicitly indicated to refer to alternatives only or the alternatives are mutually exclusive, although the disclosure supports a definition that refers to only alternatives and “and/or.” As used herein “another” may mean at least a second or more.

Throughout this application, the term “about” is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4A. A two-vector PiggyBac stable gene expression system; Ptight is an rtTET-responsive inducible promoter; pEF is the eukaryotic elongation factor 1α promoter; hPBase is the coding region for the PiggyBac transposase with codons optimized for expression in human cells. FIG. 4B. Flow cytometric analysis of EGFP expression in human ESC inducible lines after 4 days induction with or without Doxycycline (1 μg/mL). Gray lines: Human ESC inducible lines with transfection of the EGFP vector; Black lines: Human ESC R/I lines with stable PiggyBac transposon integration after 4 days induction with or without Doxycycline.

DESCRIPTION OF ILLUSTRATIVE EMBODIMENTS

Figure 1:
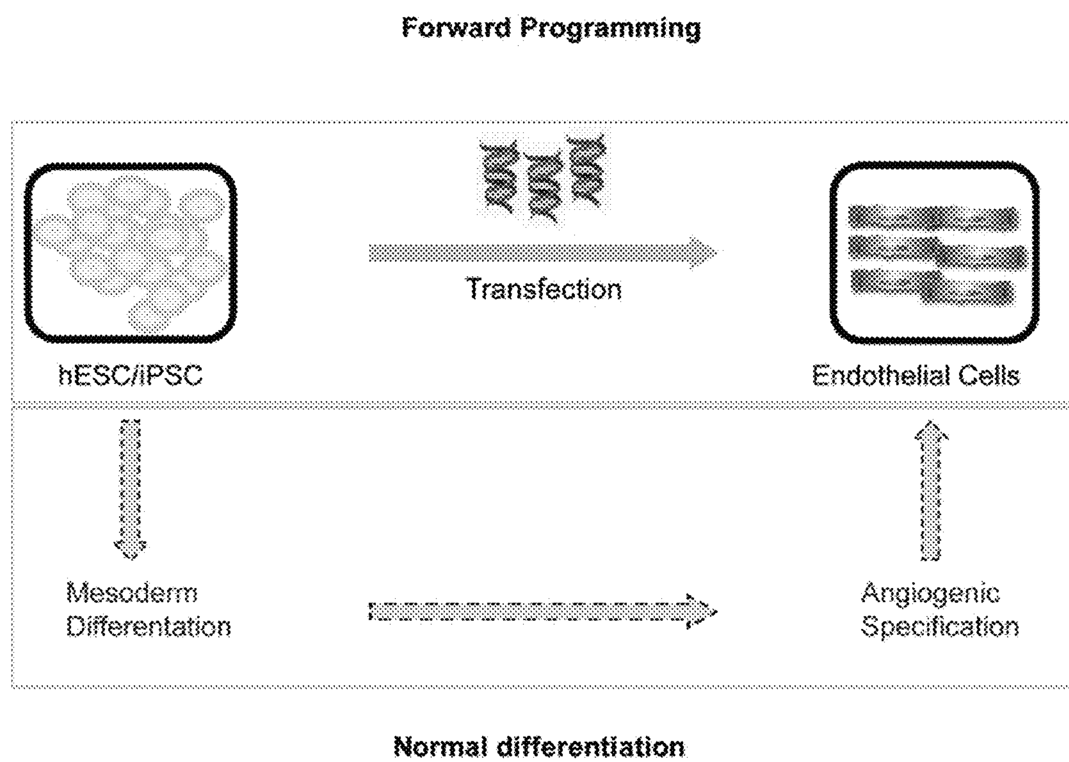
FIG. 1. Alternative approaches for endothelial cell differentiation from human ESCs/iPSCs. ECs can be efficiently induced from human ESCs/iPSCs via expression of appropriate transgene(s) (top box), bypassing most, if not all, developmental stages observed during normal differentiation (bottom box).

Endothelial cells comprise the lining of the blood vessels and are important for a variety of processes in the body. For example, endothelial cells play roles in angiogenesis, regulation of blood pressure, blood clotting, inflammation, and filtration. Endothelial cells are a heterogeneous group of cells and may have a variety of characteristics depending upon vessel size, specification to a specific organ, and morphology. Some characteristics of endothelial cells include expression of CD31, CD105 (endoglin), and Willebrand factor (also called Factor VIII), as well as the ability to take up acetylated low density lipoprotein (ac-LDL).

The present invention overcomes several major problems with current technologies by providing methods and compositions for endothelial cell production by forward programming or transdifferentiation. In contrast to previous methods using step-wise differentiation protocols, certain aspects of these methods increase the level of endothelial programming transcription factors in non-endothelial cells to provide endothelial cells by forward programming or transdifferentiation. Extra steps, such as adding different growth factors during various intermediate developmental stages may be unnecessary in certain aspects of the present methods. Therefore, certain aspects of the present methods may be more time- and cost-efficient and may enable manufacture of endothelial cells or endothelial progenitor cells for therapeutics from a renewable source, such as, for example, stem cells or somatic cells. Further embodiments and advantages of the invention are described below.

I. Definitions

"Programming" is a process that alters the type of progeny a cell can produce. For example, a cell has been programmed when it has been altered so that it can form progeny of at least one new cell type, either in culture or in vivo, as compared to what it would have been able to form under the same conditions without programming. This means that after sufficient proliferation, a measurable proportion of progeny having phenotypic characteristics of the new cell type are observed, if essentially no such progeny could form before programming; alternatively, the proportion having characteristics of the new cell type is measurably more than before programming. This process includes differentiation, dedifferentiation and transdifferentiation. "Differentiation" is the process by which a less specialized cell becomes a more specialized cell type. "Dedifferentiation" is a cellular process in which a partially or terminally differentiated cell reverts to an earlier developmental stage, such as pluripotency or multipotency. "Transdifferentiation" is a process of transforming one differentiated cell type into another differentiated cell type. Under certain conditions, the proportion of progeny with characteristics of the new cell type may be at least about 1%, 5%, 25% or more in order of increasing preference.

The term "endothelial programming factor" is a gene that, when expressed alone or in combination with another programming factor gene, is capable of causing direct differentiation of pluripotent cells or non-endothelial somatic cells into endothelial cells or endothelial precursor cells.

The term "forward programming" refers to the programming of a multipotent or pluripotent cell, as opposed to a differentiated somatic cell that has no pluripotency, by the provision of one or more specific lineage-determining genes or gene products to the multipotent or pluripotent cell. For example, forward programming may describe the process of programming ESCs or iPSCs to endothelial cells, endothelial precursor cells, other precursor cells, or other differentiated somatic cells.

The term "exogenous," when used in relation to a protein, gene, nucleic acid, or polynucleotide in a cell or organism refers to a protein, gene, nucleic acid, or polynucleotide that has been introduced into the cell or organism by artificial or natural means; or in relation to a cell, refers to a cell that was isolated and subsequently introduced to other cells or to an organism by artificial or natural means. An exogenous nucleic acid may be from a different organism or cell, or it may be one or more additional copies of a nucleic acid that occurs naturally within the organism or cell. An exogenous cell may be from a different organism, or it may be from the same organism. By way of a non-limiting example, an exogenous nucleic acid is one that is in a chromosomal location different from that of natural cells, or is otherwise flanked by a different nucleic acid sequence than that found in nature. An exogenous nucleic acid may also be extra-chromosomal, such as an episomal vector.

By "expression construct" or "expression cassette" is meant a nucleic acid molecule that is capable of directing transcription. An expression construct includes, at a minimum, one or more transcriptional control elements (such as promoters, enhancers or a structure functionally equivalent thereof) that direct gene expression in one or more desired cell types, tissues or organs. Additional elements, such as a transcription termination signal, may also be included.

A "vector" or "construct" (sometimes referred to as a gene delivery system or gene transfer "vehicle") refers to a macromolecule or complex of molecules comprising a polynucleotide to be delivered to a host cell, either in vitro or in vivo.

A "plasmid," a common type of a vector, is an extra-chromosomal DNA molecule separate from the chromosomal DNA that is capable of replicating independently of the chromosomal DNA. In certain cases, it is circular and double-stranded.

An "origin of replication" ("ori") or "replication origin" is a DNA sequence, e.g., in a lymphotrophic herpes virus, that when present in a plasmid in a cell is capable of maintaining linked sequences in the plasmid, and/or a site at or near where DNA synthesis initiates. An on for EBV includes FR sequences (20 imperfect copies of a 30 bp repeat), and preferably DS sequences; however, other sites in EBV bind EBNA-1, e.g., Rep* sequences can substitute for DS as an origin of replication (Kirshmaier and Sugden, 1998). Thus, a replication origin of EBV includes FR, DS or Rep* sequences or any functionally equivalent sequences through nucleic acid modifications or synthetic combination derived therefrom. For example, the present invention may also use genetically engineered replication origin of EBV, such as by insertion or mutation of individual elements, as specifically described in Lindner, et. al., 2008.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence “TATAC” corresponds to a reference sequence “TATAC” and is complementary to a reference sequence “GTATA.”

A “gene,” “polynucleotide,” “coding region,” “sequence,” “segment,” “fragment,” or “transgene” that “encodes” a particular protein, is a nucleic acid molecule that is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term “control elements” refers collectively to promoter regions, polyadenylation signals, transcription termination sequences, upstream regulatory domains, origins of replication, internal ribosome entry sites (IRES), enhancers, splice junctions, and the like, which collectively provide for the replication, transcription, post-transcriptional processing, and translation of a coding sequence in a recipient cell. Not all of these control elements need be present so long as the selected coding sequence is capable of being replicated, transcribed, and translated in an appropriate host cell.

The term “promoter” is used herein in its ordinary sense to refer to a nucleotide region comprising a DNA regulatory sequence, wherein the regulatory sequence is derived from a gene that is capable of binding RNA polymerase and initiating transcription of a downstream (3' direction) coding sequence.

By “enhancer” is meant a nucleic acid sequence that, when positioned proximate to a promoter, confers increased transcription activity relative to the transcription activity resulting from the promoter in the absence of the enhancer domain.

By “operably linked” with reference to nucleic acid molecules is meant that two or more nucleic acid molecules (e.g., a nucleic acid molecule to be transcribed, a promoter, and an enhancer element) are connected in such a way as to permit transcription of the nucleic acid molecule. “Operably linked” with reference to peptide and/or polypeptide molecules means that two or more peptide and/or polypeptide molecules are connected in such a way as to yield a single polypeptide chain, i.e., a fusion polypeptide, having at least one property of each peptide and/or polypeptide component of the fusion. The fusion polypeptide is preferably chimeric, i.e., composed of heterologous molecules.

“Homology” refers to the percent of identity between two polynucleotides or two polypeptides. The correspondence between one sequence and another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions that promote the formation of stable duplexes between homologous regions, followed by digestion with single strand-specific nuclease(s), and size determination of the digested fragments. Two DNA, or two polypeptide, sequences are “substantially homologous” to each other when at least about 80%, preferably at least about 90%, and most preferably at least about 95% of the nucleotides, or amino acids, respectively match over a defined length of the molecules, as determined using the methods above.

The term “cell” is herein used in its broadest sense in the art and refers to a living body that is a structural unit of tissue of a multicellular organism, is surrounded by a membrane structure that isolates it from the outside, has the capability of self-replicating, and has genetic information and a mechanism for expressing it. Cells used herein may be naturally-occurring cells or artificially modified cells (e.g., fusion cells, genetically modified cells, etc.).

As used herein, the term “stem cell” refers to a cell capable of giving rising to at least one type of a more specialized cell. A stem cells has the ability to self-renew, i.e., to go through numerous cycles of cell division while maintaining the undifferentiated state, and has potency, i.e., the capacity to differentiate into specialized cell types. Typically, stem cells can regenerate an injured tissue. Stem cells herein may be, but are not limited to, embryonic stem (ES) cells, induced pluripotent stem cells, or tissue stem cells (also called tissue-specific stem cells, or somatic stem cells). Any artificially produced cell having the above-described abilities (e.g., fusion cells, reprogrammed cells, or the like used herein) may be a stem cell.

“Embryonic stem (ES) cells” are pluripotent stem cells derived from early embryos. An ES cell was first established in 1981, which has also been applied to production of knockout mice since 1989. In 1998, a human ES cell was established, which is currently becoming available for regenerative medicine.

Unlike ES cells, tissue stem cells have a limited differentiation potential. Tissue stem cells are present at particular locations in tissues and have an undifferentiated intracellular structure. Therefore, the pluripotency of tissue stem cells is typically low. Tissue stem cells have a higher nucleus/cytoplasm ratio and have few intracellular organelles. Most tissue stem cells have low pluripotency, a long cell cycle, and proliferative ability beyond the life of the individual. Tissue stem cells are separated into categories, based on the sites from which the cells are derived, such as the dermal system, the digestive system, the bone marrow system, the nervous system, and the like. Tissue stem cells in the dermal system include epidermal stem cells, hair follicle stem cells, and the like. Tissue stem cells in the digestive system include pancreatic (common) stem cells, liver stem cells, and the like. Tissue stem cells in the bone marrow system include hematopoietic stem cells, mesenchymal stem cells, and the like. Tissue stem cells in the nervous system include neural stem cells, retinal stem cells, and the like.

“Induced pluripotent stem cells,” commonly abbreviated as iPS cells or iPSCs, refer to a type of pluripotent stem cell artificially prepared from a non-pluripotent cell, typically an adult somatic cell, or terminally differentiated cell, such as a fibroblast, a hematopoietic cell, a myocyte, a neuron, an epidermal cell, or the like, by inserting certain genes, referred to as reprogramming factors.

“Pluripotency” refers to a stem cell that has the potential to differentiate into all cells constituting one or more tissues or organs, or preferably, any of the three germ layers: endoderm (interior stomach lining, gastrointestinal tract, the lungs), mesoderm (muscle, bone, blood, urogenital), or ectoderm (epidermal tissues and nervous system). “Pluripotent stem cells” used herein refer to cells that can differentiate into cells derived from any of the three germ layers, for example, direct descendants of totipotent cells or induced pluripotent cells.

As used herein “totipotent stem cells” refers to cells having the ability to differentiate into all cells constituting an organism, such as cells that are produced from the fusion of an egg and sperm cell. Cells produced by the first few divisions of the fertilized egg are also totipotent. These cells can differentiate into embryonic and extraembryonic cell types. Pluripotent stem cells can give rise to any fetal or adult cell type. However, alone they cannot develop into a fetal or adult animal because they lack the potential to contribute to extraembryonic tissue, such as the placenta.

In contrast, many progenitor cells are multipotent stem cells, i.e., they are capable of differentiating into a limited number of cell fates. Multipotent progenitor cells can give rise to several other cell types, but those types are limited in number. An example of a multipotent stem cell is a hematopoietic cell—a blood stem cell that can develop into several types of blood cells, but cannot develop into brain cells or other types of cells. At the end of the long series of cell divisions that form the embryo are cells that are terminally differentiated, or that are considered to be permanently committed to a specific function.

As used herein, the term "somatic cell" refers to any cell other than a germ cell, such as an egg, a sperm, or the like, that does not directly transfer its DNA to the next generation. Typically, somatic cells have limited or no pluripotency. Somatic cells used herein may be naturally-occurring or genetically modified.

Cells are "substantially free" of certain undesired cell types, as used herein, when they have less that 10% of the undesired cell types, and are "essentially free" of certain cell types when they have less than 1% of the undesired cell types. However, even more desirable are cell populations wherein less than 0.5% or less than 0.1% of the total cell population comprise the undesired cell types. Thus, cell populations wherein less than 0.1% to 1% (including all intermediate percentages) of the cells of the population comprise undesirable cell types are essentially free of these cell types. A medium is "essentially free" of certain reagents, as used herein, when there is no external addition of such agents. More preferably, these agents are absent or present at an undetectable amount.

II. Cells Involved in Endothelial Cell Programming

In certain embodiments of the invention, there are disclosed methods and compositions for providing endothelial cells by forward programming of cells that are not endothelial cells. There may be also provided cells that comprise exogenous expression cassettes including one or more endothelial programming factor genes and/or reporter expression cassettes specific for endothelial cell identification. In some embodiments, the cells may be stem cells, including but not limited to, embryonic stem cells, fetal stem cells, or adult stem cells. In further embodiments, the cells may be any somatic cells.

A. Stem Cells

Stem cells are cells found in most, if not all, multi-cellular organisms. They are characterized by the ability to renew themselves through mitotic cell division and the ability to differentiate into a diverse range of specialized cell types. The two broad types of mammalian stem cells are: embryonic stem cells that are found in blastocysts, and adult stem cells that are found in adult tissues. In a developing embryo, stem cells can differentiate into all of the specialized embryonic tissues. In adult organisms, stem cells and progenitor cells act as a repair system for the body, replenishing specialized cells, and also maintain the normal turnover of regenerative organs, such as blood, skin or intestinal tissues.

Human embryonic stem cells (ESCs) and induced pluripotent stem cells (iPSCs) are capable of long-term proliferation in vitro, while retaining the potential to differentiate into all cell types of the body, including endothelial cells. Thus these cells could potentially provide an unlimited supply of patient-specific functional endothelial cells for both drug development and therapeutic uses. The differentiation of human ESCs/iPSCs to endothelial cells in vitro recapitulates normal in vivo development; i.e. they undergo the normal sequential developmental stages including mesoderm differentiation and angiogenic specification (FIG. 1). That sequential developmental process requires the addition of different growth factors at different stages of differentiation. Certain aspects of the invention provide fully functional endothelial cells by forward programming from human ESCs/iPSCs via expression of a combination of transcription factors important for endothelial cell differentiation/function, similar to the generation of iPSCs, bypassing most, if not all, normal developmental stages (FIG. 1). This approach may be more time- and cost-efficient, and generate endothelial cells with functions highly similar, if not identical, to human primary adult endothelial cells. In addition, human ESC/iPSCs, with their unlimited proliferation ability, have a unique advantage over somatic cells as the starting cell population for endothelial cell differentiation.

1. Embryonic Stem Cells

Embryonic stem cell lines (ES cell lines) are cultures of cells derived from the epiblast tissue of the inner cell mass (ICM) of a blastocyst or earlier formula stage embryos. A blastocyst is an early stage embryo—approximately four to five days old in humans and consisting of 50-150 cells. ES cells are pluripotent and give rise during development to all derivatives of the three primary germ layers: ectoderm, endoderm and mesoderm. In other words, they can develop into each of the more than 200 cell types of the adult body when given sufficient and necessary stimulation for a specific cell type. They do not contribute to the extra-embryonic membranes or the placenta.

Nearly all research to date has taken place using mouse embryonic stem cells (mES) or human embryonic stem cells (hES). Both have the essential stem cell characteristics, yet they require very different environments in order to maintain an undifferentiated state. Mouse ES cells may be grown on a layer of gelatin and require the presence of Leukemia Inhibitory Factor (LIF). Human ES cells could be grown on a feeder layer of mouse embryonic fibroblasts (MEFs) and often require the presence of basic Fibroblast Growth Factor (bFGF or FGF-2). Without optimal culture conditions or genetic manipulation (Chambers et al., 2003), embryonic stem cells will rapidly differentiate.

A human embryonic stem cell may also be defined by the presence of several transcription factors and cell surface proteins. The transcription factors Oct-4, Nanog, and Sox-2 form the core regulatory network that ensures the suppression of genes that lead to differentiation and the maintenance of pluripotency (Boyer et al., 2005). The cell surface antigens most commonly used to identify hES cells include the glycolipids SSEA3 and SSEA4 and the keratan sulfate antigens Tra-1-60 and Tra-1-81.

Methods for obtaining mouse ES cells are well known. In one method, a preimplantation blastocyst from the 129 strain of mice is treated with mouse antiserum to remove the trophoectoderm, and the inner cell mass is cultured on a feeder cell layer of chemically inactivated mouse embryonic fibroblasts in medium containing fetal calf serum. Colonies of undifferentiated ES cells that develop are subcultured on mouse embryonic fibroblast feeder layers in the presence of fetal calf serum to produce populations of ES cells. In some methods, mouse ES cells can be grown in the absence of a feeder layer by adding the cytokine leukemia inhibitory factor (LIF) to serum-containing culture medium (Smith, 2000). In other methods, mouse ES cells can be grown in serum-free medium in the presence of bone morphogenetic protein and LIF (Ying et al., 2003).

Human ES cells can be obtained from blastocysts using previously described methods (Thomson et al., 1995; Thomson et al., 1998; Thomson and Marshall, 1998; Reubinoff et al, 2000.) In one method, day-5 human blastocysts are exposed to rabbit anti-human spleen cell antiserum, then exposed to a 1:5 dilution of Guinea pig complement to lyse trophectoderm cells. After removing the lysed trophectoderm cells from the intact inner cell mass, the inner cell mass is cultured on a feeder layer of gamma-inactivated mouse embryonic fibroblasts and in the presence of fetal bovine serum. After 9 to 15 days, clumps of cells derived from the inner cell mass can be chemically (i.e. exposed to trypsin) or mechanically dissociated and replated in fresh medium containing fetal bovine serum and a feeder layer of mouse embryonic fibroblasts. Upon further proliferation, colonies having undifferentiated morphology are selected by micropipette, mechanically dissociated into clumps, and replated (see U.S. Pat. No. 6,833,269). ES-like morphology is characterized as compact colonies with apparently high nucleus to cytoplasm ratio and prominent nucleoli. Resulting ES cells can be routinely passaged by brief trypsinization or by selection of individual colonies by micropipette. In some methods, human ES cells can be grown without serum by culturing the ES cells on a feeder layer of fibroblasts in the presence of basic fibroblast growth factor (Amit et al., 2000). In other methods, human ES cells can be grown without a feeder cell layer by culturing the cells on a protein matrix such as Matrigeff or laminin in the presence of "conditioned" medium containing basic fibroblast growth factor (Xu et al., 2001). The medium is previously conditioned by coculturing with fibroblasts.

Methods for the isolation of rhesus monkey and common marmoset ES cells are also known (Thomson, and Marshall, 1998; Thomson et al., 1995; Thomson and Odorico, 2000).

Another source of ES cells are established ES cell lines. Various mouse cell lines and human ES cell lines are known and conditions for their growth and propagation have been defined. For example, the mouse CGR8 cell line was established from the inner cell mass of mouse strain 129 embryos, and cultures of CGR8 cells can be grown in the presence of LIF without feeder layers. As a further example, human ES cell lines H1, H7, H9, H13 and H14 were established by Thompson et al. In addition, subclones H9.1 and H9.2 of the H9 line have been developed. It is anticipated that virtually any ES or stem cell line known in the art may be used with the present invention, such as, e.g., those described in Yu and Thompson, 2008, which is incorporated herein by reference.

The source of ES cells for use in connection with the present invention can be a blastocyst, cells derived from culturing the inner cell mass of a blastocyst, or cells obtained from cultures of established cell lines. Thus, as used herein, the term "ES cells" can refer to inner cell mass cells of a blastocyst, ES cells obtained from cultures of inner mass cells, and ES cells obtained from cultures of ES cell lines.

2. Induced Pluripotent Stem Cells

Induced pluripotent stem (iPS) cells are cells that have the characteristics of ES cells but are obtained by the reprogramming of differentiated somatic cells. Induced pluripotent stem cells have been obtained by various methods. In one method, adult human dermal fibroblasts are transfected with transcription factors Oct4, Sox2, c-Myc and Klf4 using retroviral transduction (Takahashi et al., 2007). The transfected cells are plated on SNL feeder cells (a mouse cell fibroblast cell line that produces LIF) in medium supplemented with basic fibroblast growth factor (bFGF). After approximately 25 days, colonies resembling human ES cell colonies appear in culture. The ES cell-like colonies are picked and expanded on feeder cells in the presence of bFGF.

Based on cell characteristics, cells of the ES cell-like colonies are induced pluripotent stem cells. The induced pluripotent stem cells are morphologically similar to human ES cells, and express various human ES cell markers. Also, when grown under conditions that are known to result in differentiation of human ES cells, the induced pluripotent stem cells differentiate accordingly. For example, the induced pluripotent stem cells can differentiate into cells having endothelial cell structures and endothelial cell markers. It is anticipated that virtually any iPS cells or cell lines may be used with the present invention, including, e.g., those described in Yu and Thompson, 2008.

In another method, human fetal or newborn fibroblasts are transfected with four genes, Oct4, Sox2, Nanog and Lin28 using lentivirus transduction (Yu et al., 2007). At 12-20 days post infection, colonies with human ES cell morphology become visible. The colonies are picked and expanded. The induced pluripotent stem cells making up the colonies are morphologically similar to human ES cells, express various human ES cell markers, and form teratomas having neural tissue, cartilage, and gut epithelium after injection into mice.

Methods of preparing induced pluripotent stem cells from mouse are also known (Takahashi and Yamanaka, 2006). Induction of iPS cells typically require the expression of or exposure to at least one member from Sox family and at least one member from Oct family. Sox and Oct are thought to be central to the transcriptional regulatory hierarchy that specifies ES cell identity. For example, Sox may be Sox-1, Sox-2, Sox-3, Sox-15, or Sox-18; Oct may be Oct-4. Additional factors may increase the reprogramming efficiency, like Nanog, Lin28, Klf4, or c-Myc; specific sets of reprogramming factors may be a set comprising Sox-2, Oct-4, Nanog and, optionally, Lin-28; or comprising Sox-2, Oct4, Klf and, optionally, c-Myc.

iPS cells, like ES cells, have characteristic antigens that can be identified or confirmed by immunohistochemistry or flow cytometry, using antibodies for SSEA-1, SSEA-3 and SSEA-4 (Developmental Studies Hybridoma Bank, National Institute of Child Health and Human Development, Bethesda Md.), and TRA-1-60 and TRA-1-81 (Andrews et al., 1987). Pluripotency of embryonic stem cells can be confirmed by injecting approximately $0.5\text{-}10\times10^6$ cells into the rear leg muscles of 8-12 week old male SCID mice. Teratomas develop that demonstrate at least one cell type of each of the three germ layers.

In certain aspects of the present invention, iPS cells are made from reprogramming somatic cells using reprogramming factors comprising an Oct family member and a Sox family member, such as Oct4 and Sox2 in combination with Klf or Nanog as described above. The somatic cell for reprogramming may be any somatic cell that can be induced to pluripotency, such as a fibroblast, a keratinocyte, a hematopoietic cell, a mesenchymal cell, a liver cell, a stomach cell, or a β cell. In a certain aspect, T cells may also be used as source of somatic cells for reprogramming (see U.S. Application No. 61/184,546, incorporated herein by reference).

Reprogramming factors may be expressed from expression cassettes comprised in one or more vectors, such as an integrating vector or an episomal vector, e.g., an EBV element-based system (see U.S. Application No. 61/058,858, incorporated herein by reference; Yu et al., 2009). In a further aspect, reprogramming proteins could be introduced directly into somatic cells by protein transduction (see U.S. Application No. 61/172,079, incorporated herein by reference).

3. Embryonic Stem Cells Derived by Somatic Cell Nuclear Transfer

Pluripotent stem cells can be prepared by means of somatic cell nuclear transfer, in which a donor nucleus is transferred into a spindle-free oocyte. Stem cells produced by nuclear transfer are genetically identical to the donor nuclei. In one method, donor fibroblast nuclei from skin fibroblasts of a rhesus macaque are introduced into the cytoplasm of spindle-free, mature metaphase II rhesus macaque ooctyes by electrofusion (Byrne et al., 2007). The fused oocytes are activated by exposure to ionomycin, then incubated until the blastocyst stage. The inner cell mass of selected blastocysts are then cultured to produce embryonic stem cell lines. The embryonic stem cell lines show normal ES cell morphology, express various ES cell markers, and differentiate into multiple cell types both in vitro and in vivo. As used herein, the term "ES cells" refers to embryonic stem cells derived from embryos containing fertilized nuclei. ES cells are distinguished from embryonic stem cells produced by nuclear transfer, which are referred to as "embryonic stem cells derived by somatic cell nuclear transfer."

4. Other Stem Cells

Fetal stem cells are cells with self-renewal capability and pluripotent differentiation potential. They can be isolated and expanded from fetal cytotrophoblast cells (European Patent EPO412700) and chorionic villi, amniotic fluid and the placenta (WO/2003/042405). These references are hereby incorporated by reference in their entirety. Cell surface markers of fetal stem cells include CD117/c-kit$^+$, SSEA3$^+$, SSEA4$^+$ and SSEA1$^-$.

Somatic stem cells have been identified in most organ tissues. The best characterized is the hematopoietic stem cell. This is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages (see U.S. Pat. Nos. 5,635,387; 5,460,964; 5,677,136; 5,750,397; 5,759,793; 5,681,599; 5,716,827; Hill et al., 1996; all of which are hereby incorporated by reference in their entirety). When transplanted into lethally irradiated animals or humans, hematopoietic stem cells can repopulate the erythroid, neutrophil-macrophage, megakaryocyte and lymphoid hematopoietic cell pool. In vitro, hematopoietic stem cells can be induced to undergo at least some self-renewing cell divisions and can be induced to differentiate to the same lineages as is seen in vivo. Therefore, this cell fulfills the criteria of a stem cell.

The next best characterized is the mesenchymal stem cells (MSC), originally derived from the embryonic mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A number of mesenchymal stem cells have been isolated (see, for example, U.S. Pat. Nos. 5,486,359; 5,827,735; 5,811,094; 5,736,396; 5,837,539; 5,837,670; 5,827,740; Jaiswal et al., 1997; Cassiede et al., 1996; Johnstone et al., 1998; Yoo et al., 1998; Gronthos, 1994; Makino et al., 1999, all of which are hereby incorporated by reference in their entirety). Of the many mesenchymal stem cells that have been described, all have demonstrated limited differentiation to form only those differentiated cells generally considered to be of mesenchymal origin. To date, the most multipotent mesenchymal stem cell expresses the SH2$^+$ SH4$^+$ CD29$^+$ CD44$^+$ CD71$^+$ CD90$^+$ CD106$^+$ CD120a$^+$ CD124$^+$ CD14$^-$ CD34$^-$ CD45$^-$ phenotype.

Other stem cells have been identified, including gastrointestinal stem cells, epidermal stem cells, neural and hepatic stem cells, also termed oval cells (Potten, 1998; Watt, 1997; Alison et al, 1998).

In some embodiments, the stem cells useful for methods described herein include, but are not limited to, embryonic stem cells, induced plurpotent stem cells, mesenchymal stem cells, bone-marrow derived stem cells, hematopoietic stem cells, chrondrocyte progenitor cells, epidermal stem cells, gastrointestinal stem cells, neural stem cells, hepatic stem cells, adipose-derived mesenchymal stem cells, pancreatic progenitor cells, hair follicular stem cells, endothelial progenitor cells, and smooth muscle progenitor cells.

In some embodiments, the stem cells used for methods described herein are isolated from umbilical cord, placenta, amniotic fluid, chorion villi, blastocysts, bone marrow, adipose tissue, brain, peripheral blood, the gastrointestinal tract, cord blood, blood vessels, skeletal muscle, skin, liver, and menstrual blood. Stem cells prepared in the menstrual blood are called endometrial regenerative cells (available from Medistem, Inc.).

One ordinarily skilled in the art can locate, isolate, and expand such stem cells. The detailed procedures for the isolation of human stem cells from various sources are described in Current Protocols in Stem Cell Biology (2007), which is hereby incorporated by reference in its entirety. Alternatively, commercial kits and isolation systems can be used—e.g., the BD FACSAria cell sorting system, BD IMag magnetic cell separation system, and BD IMag mouse hematopoietic progenitor cell enrichment set from BD Biosciences. Methods of isolating and culturing stem cells from various sources are also described in U.S. Pat. Nos. 5,486,359, 6,991,897, 7,015,037, 7,422,736, 7,410,798, 7,410,773, 7,399,632; and these are hereby incorporated by reference in their entirety.

B. Somatic Cells

In certain aspects of the invention, there may also be provided methods of transdifferentiation, i.e., the direct conversion of one somatic cell type into another, e.g., deriving endothelial cells from other somatic cells. However, the human somatic cells may be limited in supply, especially those from living donors. In certain aspects, to provide an unlimited supply of starting cells for programming, somatic cells may be immortalized by introduction of immortalizing genes or proteins, such as hTERT or oncogenes. The immortalization of cells may be reversible (e.g., using removable expression cassettes) or inducible (e.g., using inducible promoters).

Somatic cells in certain aspects of the invention may be primary cells (non-immortalized cells), such as those freshly isolated from an animal, or may be derived from a cell line (immortalized cells). The cells may be maintained in cell culture following their isolation from a subject. In certain embodiments, the cells are passaged once or more than once (e.g., between 2-5, 5-10, 10-20, 20-50, 50-100 times, or more) prior to their use in a method of the invention. In some embodiments the cells will have been passaged no more than 1, 2, 5, 10, 20, or 50 times prior to their use in a method of the invention. They may be frozen, thawed, etc.

The somatic cells used or described herein may be native somatic cells, or engineered somatic cells, i.e., somatic cells which have been genetically altered. Somatic cells of the present invention are typically mammalian cells, such as, for example, human cells, primate cells or mouse cells. They may be obtained by well-known methods and can be obtained from any organ or tissue containing live somatic cells, e.g., blood, bone marrow, skin, lung, pancreas, liver, stomach, intestine, heart, reproductive organs, bladder, kidney, urethra and other urinary organs, etc.

Mammalian somatic cells useful in the present invention include, but are not limited to, Sertoli cells, endothelial cells, granulosa cells, neurons, pancreatic islet cells, epidermal cells, epithelial cells, hepatocytes, hair follicle cells, keratinocytes, hematopoietic cells, melanocytes, chondrocytes, lymphocytes (B and T lymphocytes), erythrocytes, macrophages, monocytes, mononuclear cells, cardiac muscle cells, and other muscle cells, etc.

In some embodiments, cells are selected based on their expression of an endogenous marker known to be expressed only or primarily in a desired cell type. For example, vimentin is a fibroblast marker. Other useful markers include various keratins, cell adhesion molecules such as cadherins, fibronectin, CD molecules, etc. The population of somatic cells may have an average cell cycle time of between 18 and 96 hours, e.g., between 24-48 hours, between 48-72 hours, etc. In some embodiments, at least 90%, 95%, 98%, 99%, or more of the cells would be expected to divide within a predetermined time such as 24, 48, 72, or 96 hours.

Methods described herein may be used to program one or more somatic cells, e.g., colonies or populations of somatic cells into endothelial cells. In some embodiments, a population of cells of the present invention is substantially uniform in that at least 90% of the cells display a phenotype or characteristic of interest. In some embodiments at least 95%, 96%, 97%, 98%, 99%, 99.5%, 99.8%, 99.9, 99.95% or more of the cells display a phenotype or characteristic of interest. In certain embodiments of the invention the somatic cells have the capacity to divide, i.e., the somatic cells are not post-mitotic.

Somatic cells may be partially or completely differentiated. Differentiation is the process by which a less specialized cell becomes a more specialized cell type. Cell differentiation can involve changes in the size, shape, polarity, metabolic activity, gene expression and/or responsiveness to signals of the cell. For example, hematopoietic stem cells differentiate to give rise to all the blood cell types including myeloid (monocytes and macrophages, neutrophils, basophils, eosinophils, erythrocytes, megakaryocytes/platelets, dendritic cells) and lymphoid lineages (T-cells, B-cells, NK-cells). During progression along the path of differentiation, the ultimate fate of a cell becomes more fixed. As described herein, both partially differentiated somatic cells and fully differentiated somatic cells can be programmed as described herein to produce desired cell types such as endothelial cells.

III. Endothelial Programming Factors

Certain aspects of the invention provide endothelial programming factors for endothelial programming. The endothelial cells could be produced directly from other cell sources by increasing the level of endothelial programming factors in cells. The numerous functions of endothelial cells could be controlled at the transcriptional level by the concerted actions of a limited number of endothelial cell-enriched transcription factors. Any transcription factors important for endothelial cell differentiation or function may be used herein, like endothelial cell-enriched transcription factors, particularly the genes thereof listed in this section. The inventors also contemplate that all the isoforms and variants of the genes listed in this section are included in this invention, and non-limiting examples of accession numbers for certain isoforms or variants are provided.

For example, by effecting expression of a combination of transcription factors disclosed herein, the differentiation into endothelial cells from pluripotent stem cells may bypass most, if not all, normal developmental stages.

In certain embodiments, the endothelial programming factor is ERG, which is also known as: transcriptional regulator ERG, ets-related transforming protein ERG, TMPRSS2-ERG prostate cancer specific, v-ets erythroblastosis virus E26 oncogene like, v-ets avian erythroblastosis virus E26 oncogene related, transforming protein ERG. In some embodiments, the endothelial programming factor may be an isoform of ERG, such as ERG-1 (accession number: NM_182918.3; GI: 209954798) (SEQ ID NOS:13 and 14), ERG-2 (SEQ ID NOS:9 and 10), ERG isoform 3 (SEQ ID NOS:11 and 12), or ERG-4 (accession number: NM_001136155.1; GI: 209954807) (SEQ ID NOS:15 and 16). In particular embodiments, the endothelial programming factor is ERG-3. In other particular embodiments, the endothelial programming factor is ETV2 (also called ER71, ETSRP71) (NCBI Accession No. NM_014209, Version NM_014209.2, GI: 153791177) (SEQ ID NOS:17 and 18).

In other embodiments, the one or more endothelial programming factors is v-ets erythroblastosis virus E26 oncogene homolog 1 (avian) (ETS1) isoform 1 (NCBI Accession No. NM_001143820, Version NM_001143820.1, GI: 219689117), ETS1 isoform 3 (NCBI Accession No. NM_001162422, Version NM_001162422.1, GI: 241666445), ETS1 isoform 2 (NCBI Accession No. NM_005238, Version NM_005238.3, GI: 219689116), V-ets erythroblastosis virus E26 oncogene homolog 2 (avian) (ETS2) (NCBI Accession No. NM_005239, Version NM_005239.4, GI: 56119171), E74-like factor 1 (ELF-1) isoform b (NCBI Accession No. NM_001145353, Version NM_001145353.1, GI: 223941928), ELF-1 isoform a (NCBI Accession No. NM_172373, Version NM_172373.3, GI: 223941931), ELK-4 isoform a (NCBI Accession No. NM_001973, Version NM_001973.2, GI: 41872447), ELK-4 isoform b (NCBI Accession No. NM_021795, Version NM_021795.2, GI: 41872461), friend leukemia virus integration 1 (FLI-1) isoform 2 (NCBI Accession No. NM_001167681, Version NM_001167681.1, GI: 264681553), FLI-1 isoform 1 (NCBI Accession No. NM_002017, Version NM_002017.3, GI: 194018460), ETV6 (also called TEL or TEL1) (NCBI Accession No. NM_001987, Version NM_001987.4, GI: 153267458), T-cell acute lymphocytic leukemia 1 (TAL1, also called SCL) (NCBI Accession No. NM_003189, Version NM_003189.2, GI: 197927279), GATA binding protein 2 (GATA2) isoform 1 variant 1 (NCBI Accession No. NM_001145661, Version NM_001145661.1, GI: 224611698), GATA2 isoform 1 variant 2 (NCBI Accession No. NM_032638, Version NM_032638.4, GI: 224611697), GATA2 isoform 2 (NCBI Accession No. NM_001145662, Version NM_001145662.1, GI: 224611700), or a Forkhead (FOX) transcription factors (e.g., a member of the FoxC, FoxF, FoxH, or FoxO family). All accession numbers, version numbers, and GI numbers are incorporated herein by reference as of Jul. 7, 2010.

In yet other embodiments, the one or more endothelial programming factors is BMP-4, which is important for the modulation of the proliferative and differentiative potential of hematopoietic progenitor cells (Bhardwaj et al., 2001; Bhatia et al., 1999; Chadwick 2003). Additionally, BMP-4 can modulate early hematopoietic cell development in human fetal, neonatal, and adult hematopoietic progenitor cells (Davidson and Zon, 2000; Huber et al., 1998; Marshall et al., 2000). For example, BMP-4 can regulate the proliferation and differentiation of highly purified primitive human hematopoietic cells from adult and neonatal sources (Bhatia et al., 1999), and BMP-4 can promote hematopoietic differentiation in human embryonic stem cells (Chadwick, 2003). BMP-4 can also promote differentiation of endothelial cells from endothelial progenitor cells (Wang et al., 2007).

In further embodiments, the one or more endothelial programming factors is vascular endothelial growth factor (VEGF), which is an important signaling protein that is involved in formation of the embryonic circulatory system and angiogenesis. VEGF can affect a variety of cell types including vascular endothelium and other cell types (e.g., neurons, cancer cells, kidney epithelial cells). In vitro, VEGF can stimulate endothelial cell mitogenesis and cell migration. VEGF function has also been shown to be important in a variety of disease states including cancer, diabetes, autoimmune diseases, and ocular vascular diseases.

In still further embodiments, the one or more endothelial programming factors may be Vezf1/DB1, endothelial PAS domain-containing protein 1 (EPAS1), FOXO3a, hypoxia-inducible transcription factor-2, FoxF1, FoxH1, FoxC1, FoxC2, Kruppel-like factor 2, or Kruppel-like factor 6.

Forward programming to provide endothelial cells may be accomplished by increasing the expression of any one or more of the endothelial cell factors described in this section.

IV. Delivery of Gene or Gene Products

In certain embodiments, vectors for delivery of nucleic acids encoding endothelial programming or differentiation factors may be constructed to express those factors in cells. Details of components of such vectors and delivery methods are disclosed below. In addition, protein transduction compositions or methods may be used to effect expression of the endothelial programming factors.

In a further aspect, the following systems and methods may also be used in delivery of a reporter expression cassette for identification of desired cell types, such as endothelial cells. In particular, an endothelial cell-specific regulatory element may be used to drive expression of a reporter gene. Therefore endothelial cells derived from programming may be characterized, selected or enriched via use of the reporter.

A. Nucleic Acid Delivery Systems

One of skill in the art would be well-equipped to construct a vector through standard recombinant techniques (see, for example, Sambrook et al., 2001 and Ausubel et al., 1996, both incorporated herein by reference). Vectors include but are not limited to, plasmids, cosmids, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Ban virus vectors, herpes virus vectors, vaccinia virus vectors, Harvey murine sarcoma virus vectors, murine mammary tumor virus vectors, Rous sarcoma virus vectors.

1. Viral Vectors

In generating recombinant viral vectors, non-essential genes are typically replaced with a gene or coding sequence for a heterologous (or non-native) protein. A viral vector is a kind of expression construct that utilizes viral sequences to introduce nucleic acid and possibly proteins into a cell. The ability of certain viruses to infect cells or enter cells via receptor-mediated endocytosis, and to integrate into host cell genomes and express viral genes stably and efficiently have made them attractive candidates for the transfer of foreign nucleic acids into cells (e.g., mammalian cells). Non-limiting examples of virus vectors that may be used to deliver a nucleic acid of certain aspects of the present invention are described below.

Retroviruses have promise as gene delivery vectors due to their ability to integrate their genes into the host genome, transfer a large amount of foreign genetic material, infect a broad spectrum of species and cell types, and be packaged in special cell-lines (Miller, 1992).

In order to construct a retroviral vector, a nucleic acid is inserted into the viral genome in place of certain viral sequences to produce a virus that is replication-defective. In order to produce virions, a packaging cell line containing the gag, pol, and env genes—but without the LTR and packaging components—is constructed (Mann et al., 1983). When a recombinant plasmid containing a cDNA, together with the retroviral LTR and packaging sequences, is introduced into a special cell line (e.g., by calcium phosphate precipitation), the packaging sequence allows the RNA transcript of the recombinant plasmid to be packaged into viral particles, which are then secreted into the culture medium (Nicolas and Rubenstein, 1988; Temin, 1986; Mann et al., 1983). The medium containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences. For example, recombinant lentivirus capable of infecting a non-dividing cell—wherein a suitable host cell is transfected with two or more vectors carrying the packaging functions, namely gag, pol and env, as well as rev and tat—is described in U.S. Pat. No. 5,994,136, incorporated herein by reference.

2. Episomal Vectors

The use of plasmid- or liposome-based extra-chromosomal (i.e., episomal) vectors may be also provided in certain aspects of the invention. Such episomal vectors may include, e.g., oriP-based vectors, and/or vectors encoding a derivative of EBNA-1. These vectors may permit large fragments of DNA to be introduced unto a cell and maintained extra-chromosomally, replicated once per cell cycle, partitioned to daughter cells efficiently, and elicit substantially no immune response.

In particular, EBNA-1, the only viral protein required for the replication of the oriP-based expression vector, does not elicit a cellular immune response because it has developed an efficient mechanism to bypass the processing required for presentation of its antigens on MHC class I molecules (Levitskaya et al., 1997). Further, EBNA-1 can act in trans to enhance expression of the cloned gene, inducing expression of a cloned gene up to 100-fold in some cell lines (Langle-Rouault et al., 1998; Evans et al., 1997). Finally, the manufacture of such oriP-based expression vectors is inexpensive.

Other extra-chromosomal vectors include other lymphotrophic herpes virus-based vectors. Lymphotrophic herpes virus is a herpes virus that replicates in a lymphoblast (e.g., a human B lymphoblast) and becomes a plasmid for a part of its natural life-cycle. Herpes simplex virus (HSV) is not a "lymphotrophic" herpes virus. Exemplary lymphotrophic herpes viruses include, but are not limited to EBV, Kaposi's sarcoma herpes virus (KSHV); Herpes virus saimiri (HS) and Marek's disease virus (MDV). Other sources of episome-based vectors are also contemplated, such as yeast ARS, adenovirus, SV40, or BPV.

One of skill in the art would be well-equipped to construct a vector through standard recombinant techniques (see, for example, Maniatis et al., 1988 and Ausubel et al., 1994, both incorporated herein by reference).

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide.

Such components also may include markers, such as detectable and/or selection markers that can be used to detect or select for cells that have taken up and are expressing the nucleic acid delivered by the vector. Such components can be provided as a natural feature of the vector (such as the use of certain viral vectors that have components or functionalities mediating binding and uptake), or vectors can be modified to provide such functionalities. A large variety of such vectors are known in the art and are generally available. When a vector is maintained in a host cell, the vector can either be stably replicated by the cells during mitosis as an autonomous structure, incorporated within the genome of the host cell, or maintained in the host cell's nucleus or cytoplasm.

3. Transposon-based System

According to a particular embodiment the introduction of nucleic acids may use a transposon-transposase system. The used transposon-transposase system could be the well known Sleeping Beauty, the Frog Prince transposon-transposase system (for a description of the latter, see, e.g., EP1507865), or the TTAA-specific transposon piggyBac system.

Transposons are sequences of DNA that can move around to different positions within the genome of a single cell, a process called transposition. In the process, they can cause mutations and change the amount of DNA in the genome. Transposons were also once called jumping genes, and are examples of mobile genetic elements.

There are a variety of mobile genetic elements, and they can be grouped based on their mechanism of transposition. Class I mobile genetic elements, or retrotransposons, copy themselves by first being transcribed to RNA, then reverse transcribed back to DNA by reverse transcriptase, and then being inserted at another position in the genome. Class II mobile genetic elements move directly from one position to another using a transposase to "cut and paste" them within the genome.

4. mRNA Delivery

One of skill in the art would be well-equipped to deliver to a cell any mRNA useful in the invention. For example, such techniques are provided in Yamamoto et al., 2009.

5. Homologous Recombination

In certain aspects of the invention, nucleic acid molecules can be introduced into cells in a specific manner for genome engineering, for example, via homologous recombination. As discussed above, some approaches to express genes in cells involve the use of viral vectors or transgenes that integrate randomly in the genome. These approaches, however, have the drawback of integration occurring either at sites that are unable to effectively mediate expression from the integrated nucleic or that result in the disruption of native genes. Problems associated with random integration could be partially overcome by homologous recombination to a specific locus in the target genome, e.g., Rosa26 locus.

Homologous recombination (HR), also known as general recombination, is a type of genetic recombination used in all forms of life in which nucleotide sequences are exchanged between two similar or identical strands of DNA. The technique has been the standard method for genome engineering in mammalian cells since the mid 1980s. The process involves several steps of physical breaking and the eventual rejoining of DNA. This process is most widely used to repair potentially lethal double-strand breaks in DNA. In addition, homologous recombination produces new combinations of DNA sequences during meiosis, the process by which eukaryotes make germ cells like sperm and ova. These new combinations of DNA represent genetic variation in offspring which allow populations to evolutionarily adapt to changing environmental conditions over time. Homologous recombination is also used in horizontal gene transfer to exchange genetic material between different strains and species of bacteria and viruses. Homologous recombination is also used as a technique in molecular biology for introducing genetic changes into target organisms.

Homologous recombination can be used as targeted genome modification. The efficiency of standard HR in mammalian cells is only $10^{-6}$ to $10^{-9}$ of cells treated (Capecchi, 1990). The use of meganucleases, or homing endonucleases, such as I-SceI have been used to increase the efficiency of HR. Both natural meganucleases as well as engineered meganucleases with modified targeting specificities have been utilized to increase HR efficiency (Pingoud and Silva, 2007; Chevalier et al., 2002).

On the path toward increasing the efficiency of HR has been to engineer chimeric endonucleases with programmable DNA specificity domains (Silva et al., 2011). Zinc-finger nucleases (ZFN) are one example of such a chimeric molecule in which Zinc-finger DNA binding domains are fused with the catalytic domain of a Type IIS restriction endonuclease such as FokI (as reviewed in Durai et al., 2005; PCT/US2004/030606).

Another class of such specificity molecules includes Transcription Activator Like Effector (TALE) DNA binding domains fused to the catalytic domain of a Type IIS restriction endonuclease such as FokI (Miller et al., 2011; PCT/IB2010/000154). TALENs can be designed for site-specific genome modification at virtually any given site of interest (Cermak et al., 2011; Christian et al., 2010; Li et al., 2011; Miller et al., 2011; Weber et al., 2011; Zhang et al., 2011). The site-specific DNA binding domain is expressed as a fusion protein with a DNA cleavage enzyme such as Fok I. The DNA binding domain is a scaffold of repeating amino acids; linking each of the repeats are two variable amino acids that bind to a single nucleotide in the DNA. For example, Asn-Asn binds guanosine, Asn-Ile binds adenosine, Asn-Gly bind thymidine, and His-Asp binds Cytosine. These two amino acids are known as the Repeat Variable Diresidue or RVD. There are many different RVD's and they can be engineered into the TAL Effector/Fok1 protein construct to create a specific TALEN. The RNA encoding the recombinant TALEN can then be purified and transfected into a cell for site-specific genome modification. Once the TALEN introduces the double strand DNA break, the DNA can be modified by non-homologous end joining (NHEJ) or by homologous directed repair (HDR). This allows DNA mutagenesis, deletions, or additions depending on what additional sequences are present during the DNA repair.

B. Regulatory Elements:

Eukaryotic expression cassettes included in vectors useful in the invention preferably contain (in a 5'-to-3' direction) a eukaryotic transcriptional promoter operably linked to a protein-coding sequence, splice signals including intervening sequences, and a transcriptional termination/polyadenylation sequence.

1. Promoter/Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription of a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e.g., beta actin promoter (Ng, 1989; Quitsche et al., 1989), GADPH promoter (Alexander et al., 1988, Ercolani et al., 1988), metallothionein promoter (Karin et al., 1989; Richards et al., 1984); and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at Genbank, accession no. X05244, nucleotide 283-341) or a mouse mammary tumor promoter (available from the ATCC, Cat. No. ATCC 45007). A specific example could be a phosphoglycerate kinase (PGK) promoter.

Endothelial cells can be readily identified and purified based on cell-surface antigen expression of, for example, CD31 and/or VE-cadherin. In some embodiments, endothelial cells produced by forward programming may be identified based on expression of a reporter gene. To increase both specificity and activity, the use of cis-acting regulatory elements has been contemplated. For example, an endothelial cell-specific promoter may be used. Many endothelial cell-specific promoters are known in the art. (See, e.g., DeVal and Black, 2009). Examples include, but are not limited to a promoter of Mef2c, Flk1, Tal1, endoglin, LMO2, Fli1, Tie2, Tie1, Flt1, Gata2, Prox1, ECE1, FLT4, PDGFR-beta, FOXP1, NRP1, NOTCH4, LYL1, EPCR, von Willebrand factor, factor VIII-related antigen, CD31/PECAM-1, angiotensin-converting enzyme, vascular endothelial cadherin (Cdh5), CD34, CD102/ICAM-2, CD51/61 (vitronectin receptor), CD105/endoglin, CD36, CD73/VAP-2, or Sca-1.

In certain aspects, methods of the invention also concern enhancer sequences, i.e. nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

Many endothelial cell promoter and enhancer sequences have been identified, and may be useful in methods of the invention. See, e.g., U.S. Patent App. 20100081193; DeVal and Black, 2009; Liu et al. 1995; Collins et al. 1995; Schlaeger et al., 1997.

2. Initiation Signals and Internal Ribosome Binding Sites

A specific initiation signal also may be used for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

4. Selection and Screenable Markers

In certain embodiments of the invention, cells containing a nucleic acid construct of the present invention may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art. One feature of the present invention includes using selection and screenable markers to select for endothelial cells after the programming factors have effected a desired programming change in those cells.

C. Nucleic Acid Delivery

Introduction of a nucleic acid, such as DNA or RNA, into cells to be programmed with the current invention may use any suitable methods for nucleic acid delivery for transformation of a cell., as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by *Agrobacterium*-mediated transformation (U.S. Pat. Nos. 5,591,616 and 5,563,055, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Liposome-Mediated Transfection

In a certain embodiment of the invention, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is a nucleic acid complexed with Lipofectamine (Gibco BRL) or Superfect (Qiagen). The amount of liposomes used may vary based upon the nature of the liposome as well as the cell used, for example, about 5 to about 20 μg vector DNA per 1 to 10 million of cells may be contemplated.

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the invention, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

2. Electroporation

In certain embodiments of the present invention, a nucleic acid is introduced into an organelle, a cell, a tissue or an organism via electroporation. Electroporation involves the exposure of a suspension of cells and DNA to a high-voltage electric discharge. Recipient cells can be made more susceptible to transformation by mechanical wounding. Also the amount of vectors used may vary upon the nature of the cells used, for example, about 5 to about 20 μg vector DNA per 1 to 10 million of cells may be contemplated.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

One type of electroporation is nucleofection, in which nucleic acid is transferred to a cell through the use of a device called a Nucleofector and in combination with cell specific reagents (such as the Amaxa system; Lonza Cologne AG).

3. Calcium Phosphate

In other embodiments of the present invention, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

4. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

5. Sonication Loading

Additional embodiments of the present invention include the introduction of a nucleic acid by direct sonic loading. LTK-fibroblasts have been transfected with the thymidine kinase gene by sonication loading (Fechheimer et al., 1987).

6. Microprojectile Bombardment

Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the invention.

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

D. Protein Transduction

In certain aspects of the present invention, the cells to be programmed into endothelial cells may be contacted with endothelial programming factors comprising polypeptides of endothelial cell transcription factor genes at a sufficient amount for forward programming. Protein transduction has been used as a method for enhancing the delivery of macromolecules into cells. Protein transduction domains may be used to introduce endothelial programming polypeptides or functional fragments thereof directly into cells. Research by many groups has shown that a region of the TAT protein which is derived from the HIV Tat protein can be fused to a target protein allowing the entry of the target protein into the cell. A particular exemplary protein sequence of this domain is RKKRRQRRR (SEQ ID NO:1) where R encodes Arginine, K encodes Lysine and Q encodes Glutamine. This sequence has been shown to enable the entry of a protein fusion both as an N-terminal or C-terminal fusion. The mechanism of TAT mediated entry is thought to be by macropinocytosis (Gump and Dowdy).

A "protein transduction domain" or "PTD" is an amino acid sequence that can cross a biological membrane, particularly a cell membrane. When attached to a heterologous polypeptide, a PTD can enhance the translocation of the heterologous polypeptide across a biological membrane. The PTD is typically covalently attached (e.g., by a peptide bond)

to the heterologous DNA binding domain. For example, the PTD and the heterologous DNA binding domain can be encoded by a single nucleic acid, e.g., in a common open reading frame or in one or more exons of a common gene. An exemplary PTD can include between 10-30 amino acids and may form an amphipathic helix. Many PTDs are basic in character. For example, a basic PTD can include at least 4, 5, 6 or 8 basic residues (e.g., arginine or lysine). A PTD may be able to enhance the translocation of a polypeptide into a cell that lacks a cell wall or a cell from a particular species, e.g., a mammalian cell, such as a human, simian, murine, bovine, equine, feline, or ovine cell.

A PTD can be linked to an artificial transcription factor, for example, using a flexible linker. Flexible linkers can include one or more glycine residues to allow for free rotation. For example, the PTD can be spaced from a DNA binding domain of the transcription factor by at least 10, 20, or 50 amino acids. A PTD can be located N- or C-terminal relative to a DNA binding domain. Being located N- or C-terminal to a particular domain does not require being adjacent to that particular domain. For example, a PTD N-terminal to a DNA binding domain can be separated from the DNA binding domain by a spacer and/or other types of domains. A PTD can be chemically synthesized then conjugated chemically to a separately prepared DNA binding domain with or without a linker peptide. An artificial transcription factor can also include a plurality of PTDs, e.g., a plurality of different PTDs or at least two copies of one PTD.

Several proteins and small peptides have the ability to transduce or travel through biological membranes independent of classical receptor- or endocytosis-mediated pathways. Examples of these proteins include the HIV-1 TAT protein, the herpes simplex virus 1 (HSV-1) DNA-binding protein VP22, and the *Drosophila* Antennapedia (Antp) homeotic transcription factor. The small protein transduction domains (PTDs) from these proteins can be fused to other macromolecules, peptides, or proteins to successfully transport them into a cell. Sequence alignments of the transduction domains from these proteins show a high basic amino acid content (Lys and Arg) which may facilitate interaction of these regions with negatively charged lipids in the membrane. Secondary structure analyses show no consistent structure between all three domains.

The advantages of using fusions of these transduction domains is that protein entry is rapid, concentration-dependent, and appears to work with difficult cell types.

The Tat protein from human immunodeficiency virus type I (HIV-1) has the remarkable capacity to enter cells when added exogenously (Frankel and Pabo, 1988; Mann and Frankel, 1991; Fawell et al., 1994). A particular example of a Tat PTD may include residues 47-57 of the human immunodeficiency virus Tat protein: YGRKKRRQRRR (SEQ ID NO:2). This peptide sequence is referred to as "TAT" herein. This peptide has been shown to successfully mediate the introduction of heterologous peptides and proteins in excess of 100 kDa into mammalian cells in vitro and in vivo (Ho et al., 2001). Schwarze et al. showed that when the 120 kDa β-galactosidase protein fused with TAT was injected into mouse intraperitoneally, the fusion proteins were found in all types of cells and tissues even including brain, which has been thought to be difficult because of the blood-brain-barrier (Schwarze et al., 1999).

The antennapedia homeodomain also includes a peptide that is a PTD (Derossi et al., 1994). This peptide, also referred to as "Penetratin", includes the amino acid sequence: AKIWFQNRRMKWKKENN (SEQ ID NO:3).

The HSV VP22 protein also includes a PTD. This PTD is located at the VP22 C-terminal 34 amino acid residues: DAATATRGRSAASRPTERPRAPARSASRPRRPVE (SEQ ID NO:4). See, e.g., Elliott and O'Hare (1997) and U.S. Pat. No. 6,184,038.

In one embodiment, the PTD is obtained from a human or other mammalian protein. Exemplary mammalian PTDs are described in WO 03/059940 (human SIM-2) and WO 03/059941 (Mph). In certain embodiments, the PTD could be a synthetic PTD. The minimal Tat PTD (aa 47-57) was modified to optimize protein transduction potential (Ho et al., 2001). A FITC coupled with series of synthetic PTDs was tested with cultured T lymphocytes. Some synthetic PTDs showed enhanced protein transduction compared to Tat PTD. These PTD include: YARKARRQARR (SEQ ID NO:5); YARAARRAARR (SEQ ID NO:6); YARAARRAARA (SEQ ID NO:7); YARAAARQARA (SEQ ID NO:8). Especially, the FITC conjugated with synthetic PTD YARAAARQARA (SEQ ID NO:8); showed enhanced uptake by whole blood cells when the mice were i.p. injected.

The poly-arginine peptides composed of about 6-12 arginine residues also can mediate protein transduction in some cases. For additional information about poly-arginine, see, e.g., Rothbard et al. (2000); Wender et al. (2000).

For additional information about PTDs, see also U.S. 2003/0082561; U.S. 2002/0102265; U.S. 2003/0040038; Schwarze et al. (1999); Derossi et al. (1996); Hancock et al. (1991); Buss et al. (1988); Derossi et al. (1998); Lindgren et al. (2000); Kilic et al. (2003); Asoh et al. (2002); and Tanaka et al. (2003).

In addition to PTDs, cellular uptake signals can be used. Such signals include amino acid sequences that are specifically recognized by cellular receptors or other surface proteins. Interaction between the cellular uptake signal and the cell causes internalization of the artificial transcription factor that includes the cellular uptake signal. Some PTDs may also function by interaction with cellular receptors or other surface proteins.

A number of assays are available to determine if an amino acid sequence can function as a PTD. For example, the amino acid sequence can be fused to a reporter protein such as β-galactosidase to form a fusion protein. This fusion protein is contacted with culture cells. The cells are washed and then assayed for reporter activity. Another assay detects the presence of a fusion protein that includes the amino acid sequence in question and another detectable sequence, e.g., an epitope tag. This fusion protein is contacted with culture cells. The cells are washed and then analyzed by Western or immunofluorescence to detect presence of the detectable sequence in cells. Still other assays can be used to detect transcriptional regulatory activity of a fusion protein that includes the putative PTD, a DNA binding domain, and optionally an effector domain. For example, cells contacted with such fusion proteins can be assayed for the presence or amount of mRNA or protein, e.g., using microarrays, mass spectroscopy, and high-throughput techniques.

V. Cell Culturing

Generally, cells of the present invention are cultured in a culture medium, which is a nutrient-rich buffered solution capable of sustaining cell growth.

Culture media suitable for isolating, expanding and differentiating stem cells into endothelial cells according to the method described herein include but not limited to high glucose Dulbecco's Modified Eagle's Medium (DMEM), DMEM/F-15, Liebovitz L-15, RPMI 1640, Iscove's modified Dubelcco's media (IMDM), and Opti-MEM SFM (Invitrogen Inc.). Chemically Defined Medium comprises a minimum essential medium such as Iscove's Modified Dulbecco's Medium (IMDM) (Gibco), supplemented with human serum albumin, human Ex Cyte lipoprotein, transferrin, insulin, vitamins, essential and non essential amino acids, sodium pyruvate, glutamine and a mitogen is also suitable. As used herein, a mitogen refers to an agent that stimulates division of a cell. An agent can be a chemical, usually some form of a protein that encourages a cell to commence cell division, triggering mitosis. In one embodiment, serum free media such as those described in U.S. Ser. No. 08/464,599 and WO96/39487, and the "complete media" as described in U.S. Pat. No. 5,486,359 are contemplated for use with the method described herein. In some embodiments, the culture medium is supplemented with 10% Fetal Bovine Serum (FBS), human autologous serum, human AB serum or platelet rich plasma supplemented with heparin (2 U/mL). Cell cultures may be maintained in a $CO_2$ atmosphere, e.g., 5% to 12%, to maintain pH of the culture fluid, incubated at 37° C. in a humid atmosphere and passaged to maintain a confluence below 85%.

Pluripotent stem cells to be differentiated into endothelial cells may be cultured in a medium sufficient to maintain the pluripotency. Culturing of induced pluripotent stem (iPS) cells generated in certain aspects of this invention can use various medium and techniques developed to culture primate pluripotent stem cells, more specially, embryonic stem cells, as described in U.S. Pat. App. 20070238170 and U.S. Pat. App. 20030211603. For example, like human embryonic stem (hES) cells, iPS cells can be maintained in 80% DMEM (Gibco #10829-018 or #11965-092), 20% defined fetal bovine serum (FBS) not heat inactivated, 1% non-essential amino acids, 1 mM L-glutamine, and 0.1 mM .beta.-mercaptoethanol. Alternatively, ES cells can be maintained in serum-free medium, made with 80% Knock-Out DMEM (Gibco #10829-018), 20% serum replacement (Gibco #10828-028), 1% non-essential amino acids, 1 mM L-glutamine, and 0.1 mM .beta.-mercaptoethanol. Just before use, human bFGF may be added to a final concentration of .about 4 ng/mL (WO 99/20741).

Endothelial cells of this invention can be made by culturing pluripotent stem cells or other non-endothelial cells in a medium under conditions that increase the intracellular level of endothelial programming factors to be sufficient to promote programming of the cells into endothelial cells. The medium may also contain one or more endothelial cell differentiation and maturation agents, like various kinds of growth factors. However, by increasing the intracellular level of endothelial programming transcription factors, aspects of the present invention bypass most stages toward mature endothelial cells without the need to change the medium for each of the stages. Therefore, in view of the advantages provided by the present invention, in particular aspects, the medium for culturing cells under endothelial programming may be essentially free of one or more of the endothelial cell differentiation and maturation agents, or may not undergo serial change with media containing different combination of such agents.

These agents may either help induce cells to commit to a more mature phenotype—or preferentially promote survival of the mature cells—or have a combination of both these effects. Endothelial cell differentiation and maturation agents illustrated in this disclosure may include soluble growth factors (peptide hormones, cytokines, ligand-receptor complexes, and other compounds) that are capable of promoting the growth of cells of the endothelial cell lineage. Non-limiting examples of such agents include but are not limited to endothelial growth factors such as basic FGF (bFGF), BMP-4, and VEGF, or isoforms or variants thereof.

VI. Endothelial Cell Characteristics

Cells can be characterized according to a number of phenotypic criteria. The criteria include but are not limited to the detection or quantitation of expressed cell markers, enzymatic activity, and the characterization of morphological features and intercellular signaling. In other aspects, cells to be programmed may comprise reporter gene expression cassette comprising tissue- or cell-specific transcriptional regulatory element, like endothelial cell-specific promoters for endothelial cell identification.

Endothelial cells embodied in certain aspects of this invention have morphological features characteristic of endothelial cells in the nature. The features are readily appreciated by those skilled in evaluating such things, and include a squamous appearance and a large central nucleus. One or more such features present in a single cell are consistent with the cell being a member of the endothelial cell lineage. Unbiased determination of whether cells have morphologic features characteristic of endothelial cells can be made by coding micrographs of programming progeny cells, adult or fetal endothelial cells, and one or more negative control cells, such as a fibroblast, or RPE (Retinal pigment epithelial) cells—then evaluating the micrographs in a blinded fashion, and breaking the code to determine if the endothelial cells from programming are accurately identified.

Cells of this invention can also be characterized according to whether they express phenotypic markers characteristic of cells of the endothelial cell lineage. Non-limiting examples of cell markers useful in distinguishing endothelial cells include: 7B4 antigen, ACE (angiotensin-converting enzyme), BNH9/BNF13, CD31, CD34, CD54 (ICAM-1), CD62P (p-Selectin GMP140), CD105 (Endoglin), CD144, CD146, Endocan (also called ESM-1), Endoglin (CD105), Endoglyx-1, Endomuci, Eotaxin-3, EPAS1 (Endothelial PAS domain protein 1), Factor VIII related antigen, FLI-1, Flk-1 (VEGFR-2), Flt-1 (VEGFR-1), GATA2, GBP-1 (guanylate-binding protein-1), GRO-alpha, Hex, ICAM-2 (intercellular adhesion molecule 2), LMO2, LYVE-1, MRB (magic roundabout), Nucleolin, PAL-E (pathologische anatomie Leiden-endothelium), RTKs, sVCAM-1, TAL1, TEM1 (Tumor endothelial marker 1), TEM5 (Tumor endothelial marker 5), TEM7 (Tumor endothelial marker 7), Thrombomodulin (TM, CD141), VCAM-1 (vascular cell adhesion molecule-1) (CD106), VE-cadherin (CD144), and vWF (von Willebrand factor, also called Factor VIII).

Assessment of the level of expression of such markers can be determined in comparison with other cells. Positive controls for the markers of mature endothelial cells include adult endothelial cells of the species of interest, and established endothelial cell lines. The reader is cautioned that permanent cell lines or long-term endothelial cells cultures may be metabolically altered, and fail to express certain characteristics of primary endothelial cells. Negative controls include cells of a separate lineage, such as an adult fibroblast cell line, or retinal pigment epithelial (RPE) cells. Undifferentiated stem cells are positive for some of the markers listed above, but negative for markers of mature endothelial cells, as illustrated in the examples below.

Tissue-specific (e.g., endothelial cell-specific) protein and oligosaccharide determinants listed in this disclosure can be detected using any suitable immunological technique—such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific (e.g., endothelial cell-specific) markers can also be detected at the mRNA level by Northern blot analysis, dot-blot hybridization analysis, or by real time polymerase chain reaction (RT-PCR) using sequence-specific primers in standard amplification methods (U.S. Pat. No. 5,843,780). Sequence data for the particular markers listed in this disclosure can be obtained from public databases such as GenBank. Expression at the mRNA level is said to be "detectable" according to one of the assays described in this disclosure if the performance of the assay on cell samples according to standard procedures in a typical controlled experiment results in clearly discernable hybridization or amplification product within a standard time window. Unless otherwise required, expression of a particular marker is indicated if the corresponding mRNA is detectable by RT-PCR. Expression of tissue-specific markers as detected at the protein or mRNA level is considered positive if the level is at least 2-fold, and preferably more than 10- or 50-fold above that of a control cell, such as an undifferentiated pluripotent stem cell, a fibroblast, or other unrelated cell type.

Cells can also be characterized according to whether they display enzymatic activity that is characteristic of cells of the endothelial lineage. For example, assays that detect uptake of acetylated low density lipoprotein, bradykinin degradation, angiotensin I conversion, or nitric oxide production may be useful. See, e.g., Voyta et al., 1984; King, et al., 1989; Graf et al., 1992; Ming et al., 2002. In other embodiments, cells of the invention are assayed for the ability to form tube-like structures or to respond to pro-inflammatory stimuli (e.g., TNF and/or IL-1) by upregulating the expression of one or more cell-adhesion molecules such (e.g., CD54 and/or CD62E). See, e.g., Chalupowicz et al., 1995.

The skilled reader will readily appreciate that an advantage of programming-derived endothelial cells is that they will be essentially free of other cell types that typically contaminate primary endothelial cell cultures isolated from adult or fetal tissue, such as fibroblasts, immune cells, pericytes, Kupffer cells, and other stromal cells. Programming-derived endothelial cells can be characterized as essentially free of some or all of contaminant cell types if less than 0.1% (preferably less than 100 or 10 ppm) bear markers or other features of the undesired cell type, as determined by immunostaining and fluorescence-activated quantitation, or other appropriate techniques. Moreover, programming-derived endothelial cells may be free or essentially free of mesenchymal cells or hematopoietic cells.

Endothelial cells provided by programming according to this invention can have a number of the features of the stage of cell they are intended to represent. The more of these features that are present in a particular cell, the more it can be characterized as a cell of the endothelial cell lineage. Cells having at least 2, 3, 5, 7, or 9 of these features are increasingly more preferred. In reference to a particular cell population as may be present in a culture vessel or a preparation for administration, uniformity between cells in the expression of these features is often advantageous. In this circumstance, populations in which at least about 40%, 60%, 80%, 90%, 95%, or 98% of the cells have the desired features are increasingly more preferred.

VII. Use of Endothelial Cells

The endothelial cells provided by methods and compositions of certain aspects of the invention can be used in a variety of applications. These include but are not limited to transplantation or implantation of the endothelial cells in vivo; screening cytotoxic compounds, carcinogens, mutagens growth/regulatory factors, pharmaceutical compounds, etc., in vitro; elucidating the mechanism of cardiovascular diseases and injuries; studying the mechanism by which drugs and/or growth factors operate; diagnosing and monitoring cancer in a patient; gene therapy; and the production of biologically active products, to name but a few.

A. Test Compound Screening

Programming-derived endothelial cells of this invention can be used to screen for factors (such as solvents, small molecule drugs, peptides, and polynucleotides) or environmental conditions (such as culture conditions or manipulation) that affect the characteristics of endothelial cells provided herein.

In some applications, stem cells (differentiated or undifferentiated) are used to screen factors that promote maturation of cells along the endothelial cell lineage, or promote proliferation and maintenance of such cells in long-term culture. For example, candidate endothelial cell maturation factors or growth factors are tested by adding them to stem cells in different wells, and then determining any phenotypic change that results, according to desirable criteria for further culture and use of the cells.

Particular screening applications of this invention relate to the testing of pharmaceutical compounds in drug research. The reader is referred generally to the standard textbook *In vitro Methods in Pharmaceutical Research*, Academic Press, 1997, and U.S. Pat. No. 5,030,015). In certain aspects of this invention, cells programmed to the endothelial lineage play the role of test cells for standard drug screening and toxicity assays, as have been previously performed on endothelial cell lines or primary endothelial cells in short-term culture. Assessment of the activity of candidate pharmaceutical compounds generally involves combining the endothelial cells provided in certain aspects of this invention with the candidate compound, determining any change in the morphology, marker phenotype, or metabolic activity of the cells that is attributable to the compound (compared with untreated cells or cells treated with an inert compound), and then correlating the effect of the compound with the observed change. The screening may be done either because the compound is designed to have a pharmacological effect on endothelial cells, or because a compound designed to have effects elsewhere may have unintended endothelial cell side effects. Two or more drugs can be tested in combination (by combining with the cells either simultaneously or sequentially), to detect possible drug-drug interaction effects.

In some applications, compounds are screened for toxicity to endothelial cells. See, e.g., Kuzuya et al., 2001. In other applications, endothelial cells derived from the programming methods disclosed herein are used to test the vascular permeability of a compound.

B. Endothelial Cell Therapy and Transplantation

This invention also provides for the use of endothelial cells provided herein to restore a degree of liver function to a subject needing such therapy, perhaps due to a cardiovascular disease, cardiovascular injury, or tissue injury. For example, endothelial cells and endothelial progenitor cells derived by methods disclosed here may be used to treat vascular diseases, cardiovascular diseases, ischemic diseases, vascular or other tissue injury (such as, e.g., by engineering of grafts), or hypertension, as disclosed in, for example, Dzau et al., 2005 and Li et al., 2009.

To determine the suitability of endothelial cells provided herein for therapeutic applications, the cells can first be tested in a suitable animal model. At one level, cells are assessed for their ability to survive and maintain their phenotype in vivo. Endothelial cells provided herein are administered to immunodeficient animals (such as SCID mice, or animals rendered immunodeficient chemically or by irradiation) at a site amenable for further observation, such as under the kidney capsule, into the spleen, or into a liver lobule. Tissues are harvested after a period of a few days to several weeks or more, and assessed as to whether starting cell types such as pluripotent stem cells are still present. This can be performed by providing the administered cells with a detectable label (such as green fluorescent protein, or (3-galactosidase); or by measuring a constitutive marker specific for the administered cells. Where endothelial cells provided herein are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided in elsewhere in this disclosure.

Endothelial cells and endothelial progenitor cells provided by methods of the invention may be tested in various animal models for their ability to treat cardiovascular diseases, vascular disease, vascular injuries, tissue injuries, and the like. Various such animal models that may find use in certain aspects of the present invention are discussed in, for example, Dzau et al., 2005 and Li et al., 2009.

Endothelial cells and endothelial progenitor cells provided in certain aspects of this invention that demonstrate desirable functional characteristics according to their profile of enzymes, or efficacy in animal models, may also be suitable for direct administration to human subjects in need thereof. For purposes of hemostasis, the cells can be administered at any site that has adequate access to the circulation. Endothelial cells may also be delivered at a site of injury or disease.

The endothelial cells or endothelial precursors provided in certain aspects of this invention can be used for therapy of any subject in need thereof. Human conditions that may be appropriate for such therapy include cardiovascular disease, vascular disease, ischemia, vascular injury, tissue injury, diabetes, coronary artery disease, atherosclerosis, peripheral artery disease, aneurysm, or hypertension. For human therapy, the dose is generally between about $10^9$ and $10^{12}$ cells, and typically between about $5\times10^9$ and $5\times10^{10}$ cells, making adjustments for the body weight of the subject, nature and severity of the affliction, and the replicative capacity of the administered cells. The ultimate responsibility for determining the mode of treatment and the appropriate dose lies with the managing clinician.

Certain aspects of the invention include endothelial cells or endothelial progenitor cells provided herein that form part of a bioengineered tissue graft. Such a tissue graft may be a heart tissue graft (see, e.g., U.S. Patent App. 20080199843), a vascularized tissue graft (see, e.g., U.S. Patent App. 20070299508), or any other tissue graft known in the art (see, e.g., U.S. Patent App. Nos. 20080063627; 20070184122; 20070141037; 20100145444; 20090324683; 20090149569; 20070122388).

C. Distribution for Commercial, Therapeutic, and Research Purposes

For purposes of manufacture, distribution, and use, the endothelial lineage cells of this invention are typically supplied in the form of a cell culture or suspension in an isotonic excipient or culture medium, optionally frozen to facilitate transportation or storage.

This invention also includes different reagent systems, comprising a set or combination of cells that exist at any time during manufacture, distribution, or use. The cell sets comprise any combination of two or more cell populations described in this disclosure, exemplified but not limited to programming-derived cells (endothelial lineage cells, their precursors and subtypes), in combination with undifferentiated stem cells, somatic cell-derived endothelial cells, or other differentiated cell types. The cell populations in the set sometimes share the same genome or a genetically modified form thereof. Each cell type in the set may be packaged together, or in separate containers in the same facility, or at different locations, at the same or different times, under control of the same entity or different entities sharing a business relationship.

VIII. Cells and Methods for Testing Candidate Genes in Programming

The ability of a particular candidate gene or a combination of candidate genes to act as programming factors for a specific cell type, such as endothelial cells, can be tested using the methods and cells provided in this disclosure. Efficacy of particular candidate genes or combinations of candidate genes in programming can be assessed by their effect on cell morphology, marker expression, enzymatic activity, proliferative capacity, or other features of interest, which is then determined in comparison with parallel cultures that did not include the candidate genes or combinations. Candidate genes may be transcription factors important for differentiation into desired cell types or for function of the desired cell types.

In certain embodiments, starting cells, such as pluripotent stem cells, comprising at least one expression cassette for expression of a candidate gene or a combination of candidate genes may be provided. The expression cassette may comprise an externally controllable transcriptional regulatory element, such as an inducible promoter. The activity of these promoters may be induced by the presence or absence of biotic or abiotic factors. Inducible promoters are a very powerful tool in genetic engineering because the expression of genes operably linked to them can be turned on or off at certain stages of development of an organism or in a particular tissue. Tet-On and Tet-Off inducible gene expression systems based on the essential regulatory components of the *E. coli* tetracycline-resistance operon may be used. Once established in the starting cells, the inducer doxycycline (Dox, a tetracycline derivative) could controls the expression system in a dose-dependent manner, allowing to precisely modulate the expression levels of candidate genes.

To aid identification of desired cell types, the starting cells may further comprise a cell-specific or tissue-specific reporter expression cassette. The reporter expression cassette may comprise a reporter gene operably linked to a transcriptional regulatory element specific for the desired cell types. For example, the reporter expression cassette may comprise a endothelial cell-specific promoter for endothelial cell production, isolation, selection, or enrichment. The reporter gene may be any selectable or screenable marker gene known in the art and exemplified in the preceding disclosure.

IX. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Forward Programming into Endothelial Cells

Alternative approaches for endothelial cell differentiation from human ESC/iPSCs are shown in FIG. 1. Endothelial cells can likely be efficiently induced from human ESC/iPSCs via expression of an appropriate transgene or transgene combination (top box), bypassing most, if not all, developmental stages required during normal differentiation (bottom box).

Figure 2:
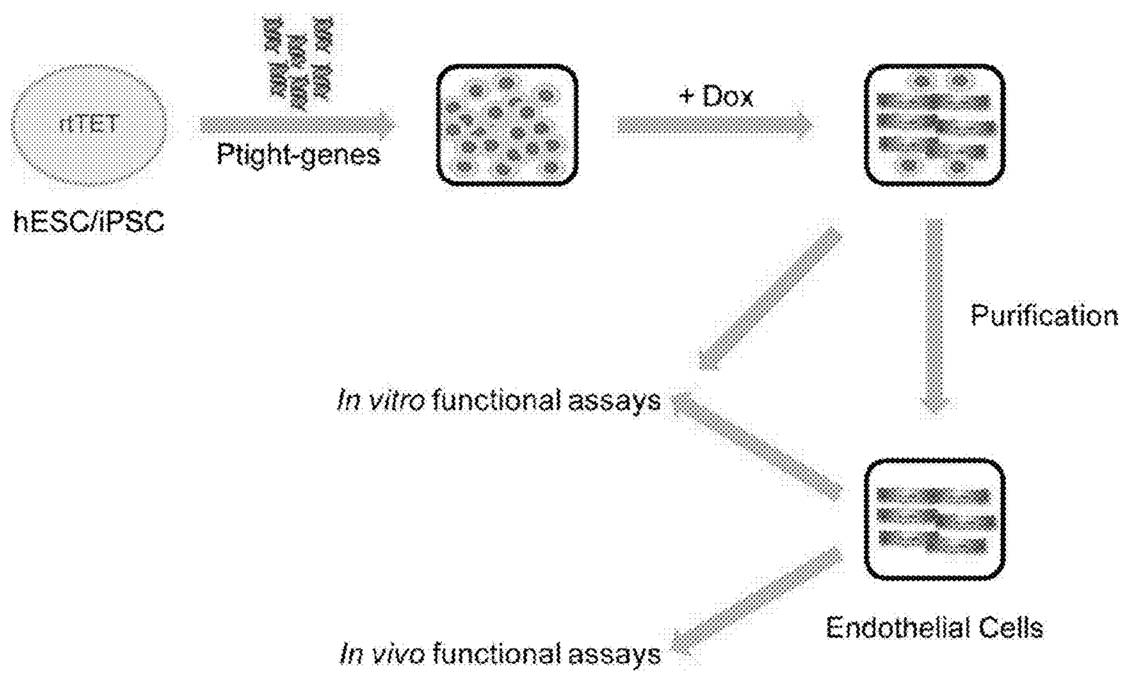
FIG. 2. The strategy employed for identifying transgenes that directly convert human ESC/iPSCs to endothelial cells. Human ESCs/iPSCs were engineered to constitutively express rtTET protein for inducible gene expression. Transgenes under the control of the inducible promoter Ptight are introduced into the engineered hESCs/iPSCs by electroporation. Upon doxycycline (Dox) addition, transgene expression is induced, and EC differentiation is monitored by the characteristic EC morphology, along with expression of EC markers (CD31, CD144 (VE-cadherin)) by flow cytometry.

The strategy employed for identifying transgenes that could directly convert human ESC/iPSCs to mature endothelial cells (FIG. 2). Human ESC/iPSCs were engineered to constitutively express rtTET protein for inducible gene expression. Transgenes under the control of the inducible promoter Ptight were introduced into the engineered hESC/iPSCs by electroporation. Upon doxycycline (Dox) addition, transgene expression is induced, and EC differentiation is monitored by the characteristic EC morphology along with expression of definitive EC markers (e.g., CD31, CD144 (VE-cadherin)) by flow cytometry. Endothelial cells thus programmed are purified for in vitro and in vivo functional assays.

Figure 3:
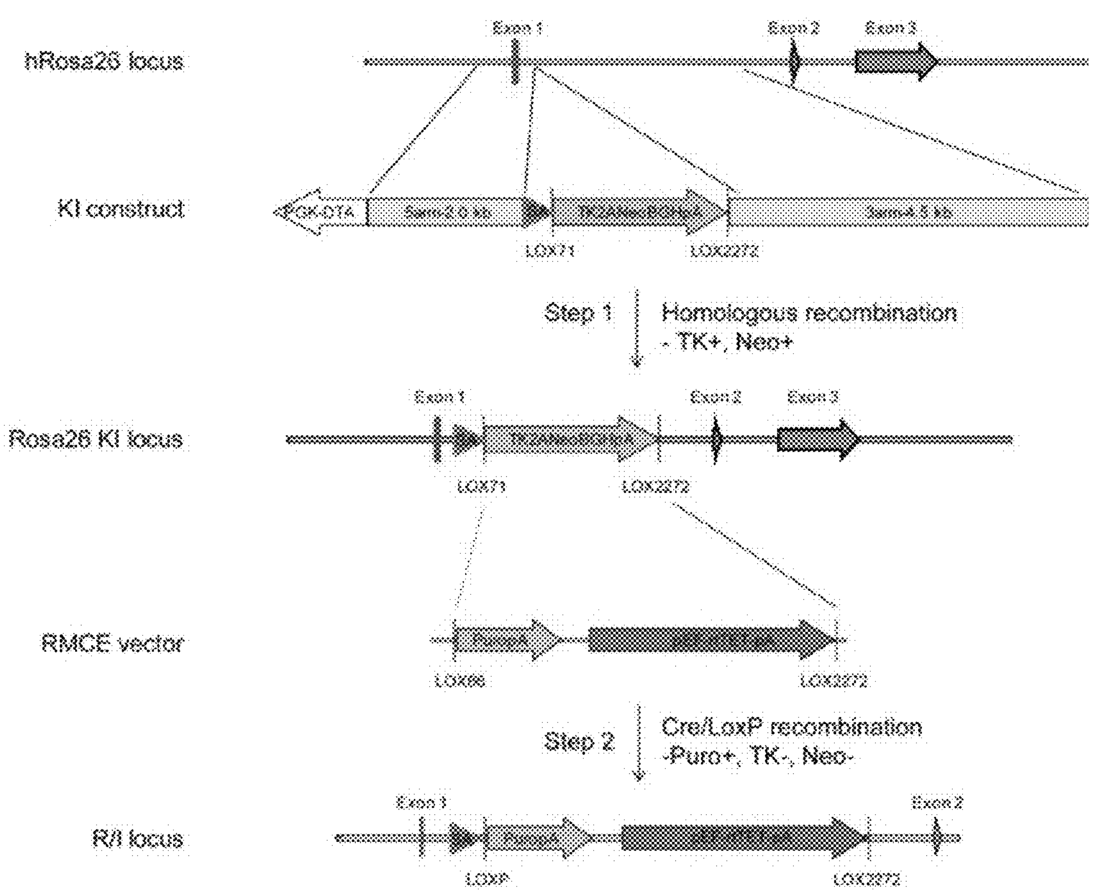
FIG. 3. The establishment of human ESC/iPSC inducible lines for endothelial cell differentiation. The human Rosa26 locus on chromosome 3 was selected to allow the expression of rtTET, while minimizing the chromosome location-dependent silencing effect. First, the LoxP recombination sites (LOX71 and LOX2272) were introduced into a site between exon 1 and exon 2 of the human ROSA 26 gene via homologous recombination. The targeting construct (KI construct) used the phosphoglycerate kinase promoter (PGK)-driven expression of diphtheria toxin A fragment gene (DTA) for negative selection, and contains a ~2.0 kb 5' arm and a 4.5 kb 3' arm. A splicing acceptor signal from human BCL2 gene (SA) was placed in front of LOX71 site to allow the expression of selection markers from the endogenous human ROSA26 promoter. The coding region for thymidine kinase (TK) was included to enable negative selection against incorrect Cre/LoxP recombination events at step 2 using ganciclovir. The neomycin phosphotransferase (Neo) was used for positive selection during homologous recombination (step 1). The foot-and-mouth disease virus peptide (2A) was used to co-express the TK and Neo genes from the endogenous human ROSA26 promoter. BGHpA: polyadenylation signal derived from bovine growth hormone gene. The homologous recombination yielded parental human ESC/iPSC lines for efficient cassette exchange via Cre/LoxP recombination. To establish inducible cell lines for EC differentiation, rtTET driven by the constitutively active eukaryotic elongation factor 1$\alpha$ promoter (pEF) was introduced into the Rosa26 locus by lipid-mediated cotransfection of the recombination mediated cassette exchange (RMCE) vector and a Cre-expressing plasmid. The puromycin N-acetyl-transferase (Puro) was used to select for recombination events. The correctly recombined inducible cells are resistant to puromycin (Puro+) and ganciclovir (TK−), and sensitive to geneticin selection (Neo−).

The establishment of human ESC/iPSC inducible (R/I) lines for endothelial cell differentiation (FIG. 3). The human Rosa26 locus on chromosome 3 was selected to allow the expression of rtTET, while minimizing the chromosome location-dependent silencing effect. First, the LoxP recombination sites (LOX71 and LOX2272) were introduced into a site between exon 1 and exon 2 of the human ROSA26 gene via homologous recombination. The targeting construct (KI construct) used the phosphoglycerate kinase promoter (PGK)-driven expression of diphtheria toxin A fragment gene (DTA) for negative selection, and contains a ~2.0 kb 5' arm and a 4.5 kb 3' arm. A splicing acceptor signal from the human BCL2 gene (SA) was placed in front of the LOX71 site to allow the expression of selection markers from the endogenous human ROSA26 promoter. The coding region for thymidine kinase (TK) was included to enable negative selection against incorrect Cre/LoxP recombination events at step 2 using ganciclovir. The neomycin phosphotransferase (Neo) was used for positive selection during homologous recombination (step 1). The foot-and-mouth disease virus peptide (2A) was used to co-express the TK and Neo genes from the endogenous human ROSA26 promoter. BGHpA is a polyadenylation signal derived from bovine growth hormone gene. The homologous recombination yielded parental human ESC/iPSC lines for efficient cassette exchange via Cre/LoxP recombination.

To establish inducible cell lines for endothelial cell differentiation, rtTET driven by the constitutively active eukaryotic elongation factor 1$\alpha$ promoter (pEF) was introduced into the Rosa26 locus by lipid-mediated cotransfection of the recombination mediated cassette exchange (RMCE) vector and a Cre-expressing plasmid. The puromycin N-acetyl-transferase (Puro) was used to select for recombination events. The correctly recombined inducible cells are resistant to puromycin (Puro+) and ganciclovir (TK−), and sensitive to geneticin selection (Neo−).

Figure 4:
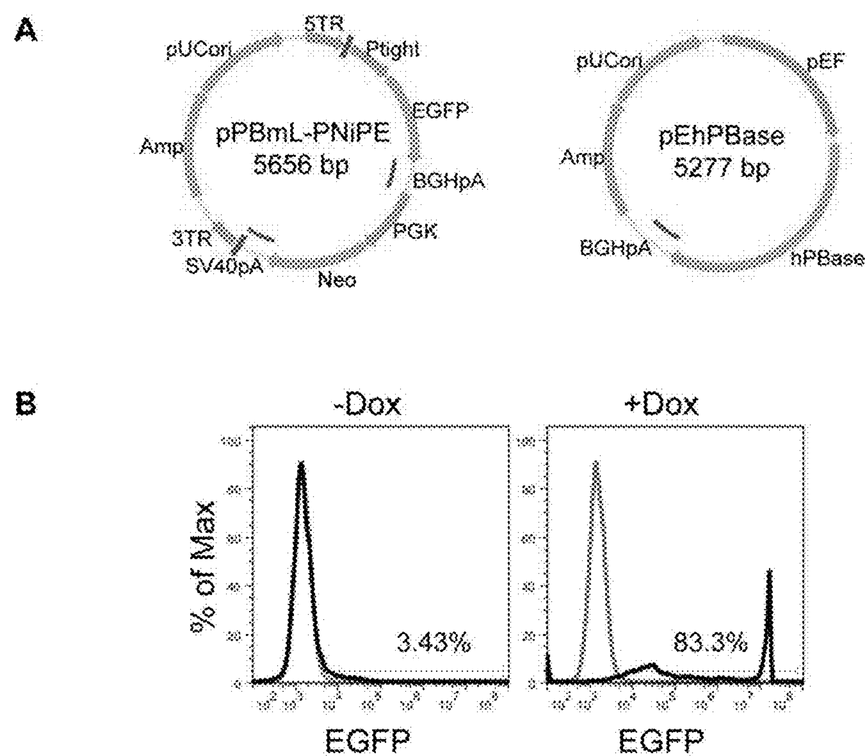
FIGS. 4A, 4B. Confirmation of Tet-On inducible gene expression in human H1 ESC inducible lines.

Confirmation of the Tet-On inducible gene expression in human H1 ESC inducible lines (FIG. 4). FIG. 4A shows a two-vector PiggyBac stable gene expression system. Ptight is an rtTET-responsive inducible promoter; pEF is the eukaryotic elongation factor 1$\alpha$ promoter; and hPBase is the coding region for the PiggyBac transposase with codons optimized for expression in human cells.

EGFP driven by the Ptight promoter was introduced into human ESC inducible lines using Fugene HD-mediated transfection of both shown in FIG. 4A. Human ESCs with stable PiggyBac transposon integration were selected with geneticin (100 μg/mL). The cells were observed after 2 days induction with or without Doxycycline (at 1 μg/mL), and EGFP expression in the Doxycycline-induced cells was confirmed microscopically. FIG. 4B shows flow cytometric analysis of EGFP expression in human ESC inducible lines after 4 days induction with or without Doxycycline (1 μg/mL). Gray lines are Human ESC inducible lines with transfection of the EGFP vector; black lines are Human ESC R/I lines with stable PiggyBac transposon integration after 4 days induction with or without Doxycycline.

Figure 5:
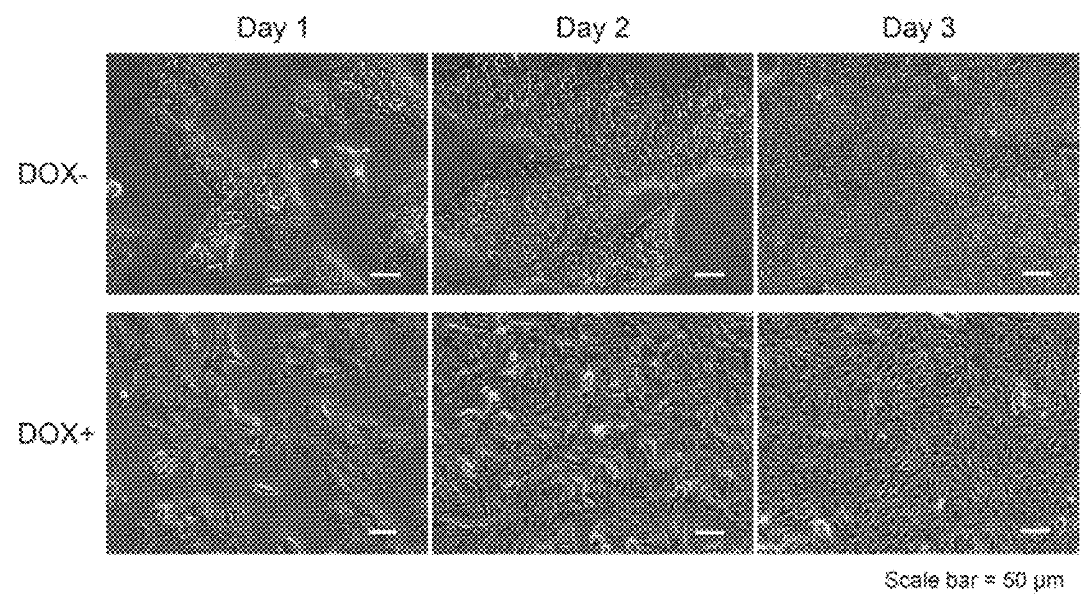
FIG. 5. Bright-field images of direct endothelial cell (EC) induction from human ESC inducible lines via ERG expression. ERG-3 was cloned into the PiggyBac vector (FIG. 4A) under the control of the Ptight promoter and introduced into the human ESC inducible line by electroporation, along with an hPBase-expressing vector. Transfected cells were cultured in TeSR medium on matrigel in the presence of geneticin (100 μg/ml) for selection of transformants having stable genomic transgene integration. Doxycycline (0.2 μg/ml) was added to induce ERG-3 expression, and the TeSR was replaced with endothelial serum-free medium (ESFM; Invitrogen) supplemented with 10 ng/ml basic FGF and 20 ng/ml VEGF (both from Peprotech). Differentiated cells acquire the EC morphology on day 2-3 of ERG induction. Although ERG-3 expression was used in these experiments to provide the results shown here, similar results were obtained with the other ERG isoforms including ERG isoform 1, ERG isoform 2, and ERG isoform 4 (data not shown).

Forward programming of endothelial cells (ECs) from human embryonic stem cell (ESC) inducible lines through ERG-3 expression (FIG. 5). ERG-3 was cloned into the PiggyBac vector (FIG. 4A) under the control of the Ptight promoter and introduced into the human ESC inducible line along with an hPBase-expressing vector by electroporation. Transfected cells were cultured in TeSR medium on matrigel in the presence of geneticin (100 μg/ml) for selection of transformants having stable genomic transgene integration. Doxycycline (0.2 μg/ml) was added to induce ERG expression, and the TeSR was replaced with endothelial serum-free medium (ESFM; Invitrogen) supplemented with 10 ng/ml basic FGF and 20 ng/ml VEGF (both from Peprotech). Differentiated cells acquire the EC morphology on day 2-3 of ERG induction. As shown in FIG. 5, bright-field images of forward programmed ECs showed EC morphology.

Although ERG-3 was selected for these experiments, the other ERG isoforms (including ERG-1, ERG-2, and ERG-4) provided similar results. Thus, although ERG isoform 3 was selected for the experiments because it was consistently the more efficient isoform, all other isoforms can be used as well because all isoforms provide endothelial cells by forward programming.

Figure 6:
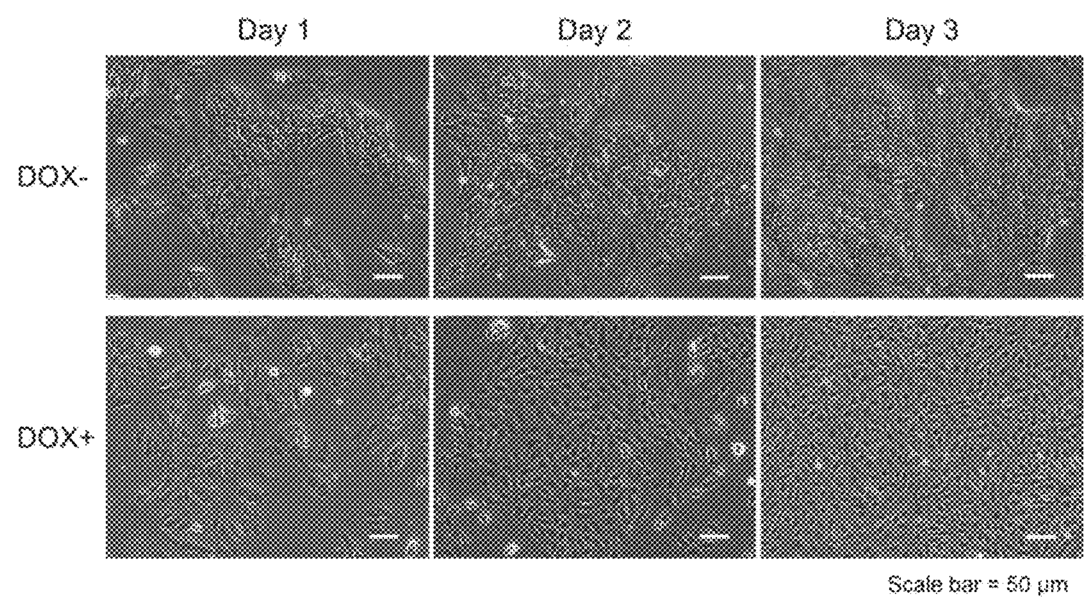
FIG. 6. Bright-field images of forward programming of ECs from human ESC inducible lines via ETV2 expression. ETV2 was cloned into the PiggyBac vector (FIG. 4A) under the control of the Ptight promoter and then introduced into the human ESC inducible line by electroporation along with the hPBase-expressing vector. Transfected cells were cultured in TeSR medium on matrigel in the presence of geneticin (100 μg/ml) for selection of transformants having stable genomic transgene integration. Doxycycline (0.2 μg/ml) was added to induce ETV2 expression, and the TeSR was replaced with endothelial serum-free medium (ESFM; Invitrogen) supplemented with 10 ng/ml basic FGF and 20 ng/ml VEGF (both from Peprotech). Differentiated cells acquire EC morphology on day 2-3 of ETV2 induction.

Forward programming of endothelial cells (ECs) from human embryonic stem cell (ESC) inducible lines through ETV2 expression. ETV2 was cloned into the PiggyBac vector (FIG. 4A) under the control of the Ptight promoter and then introduced into the human ESC inducible line by electroporation along with the hPBase-expressing vector. Transfected cells were cultured in TeSR medium on matrigel in the presence of geneticin (100 μg/ml) for selection of transformants having stable genomic transgene integration. Doxycycline (0.2 μg/ml) was added to induce ETV2 expression, and the TeSR was replaced with endothelial serum-free medium (ESFM; Invitrogen) supplemented with 10 ng/ml basic FGF and 20 ng/ml VEGF (both from Peprotech). Differentiated cells acquire EC morphology on day 2-3 of ETV2 induction. As can be seen in FIG. 6, bright-field images of forward programmed ECs showed EC morphology.

Figure 7:
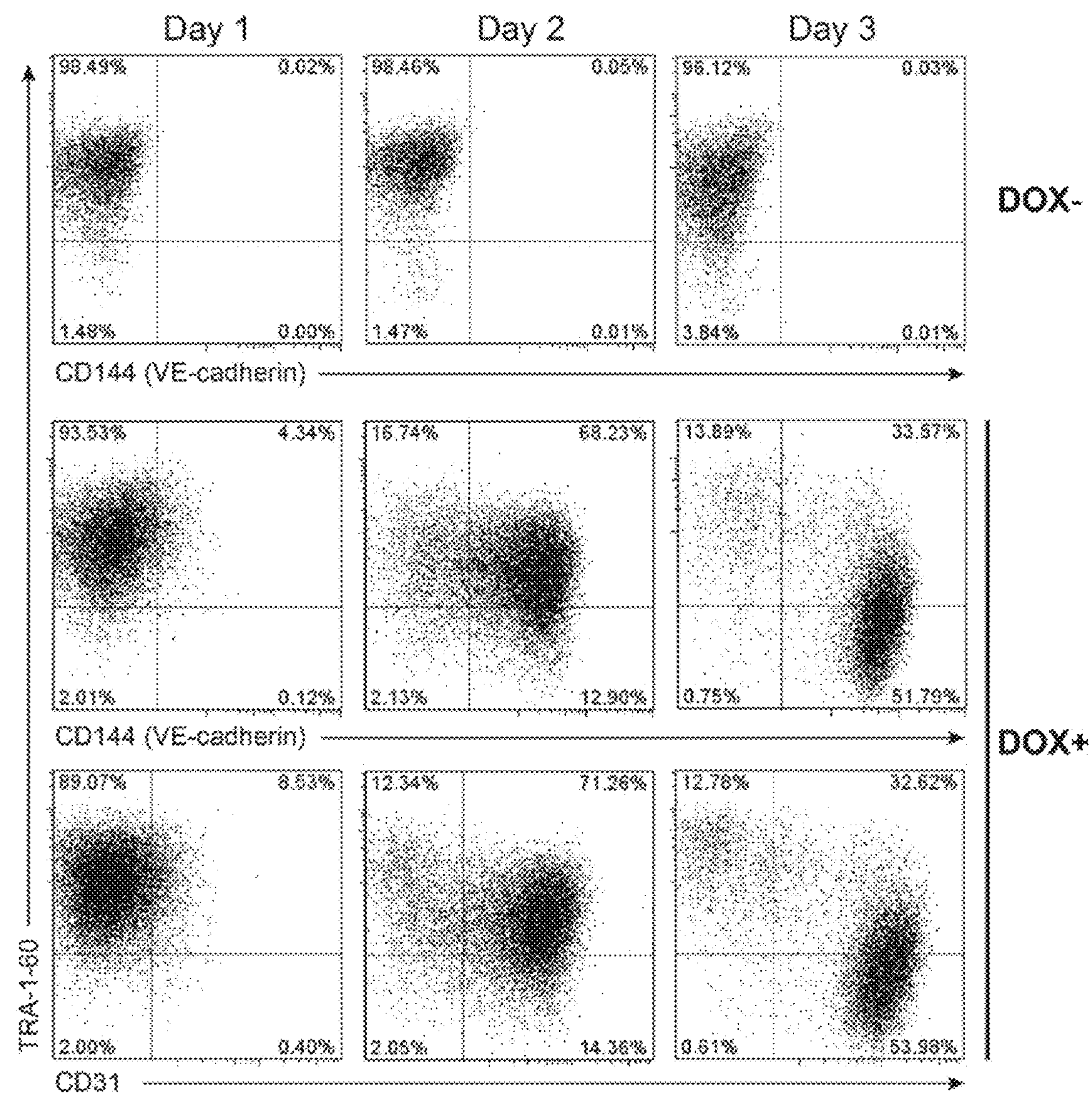
FIG. 7. Flow cytometric expression analysis of the human pluripotent stem cell-specific marker TRA-1-60 and the EC markers (CD144/VE-cadherin and CD31) during ERG-induced EC differentiation from human ESCs. The ERG-induced differentiated cells up-regulated the expression of the EC markers (CD144 and CD31), while down-regulating the expression of the human pluripotent stem cell marker TRA-1-60.
Figure 8:
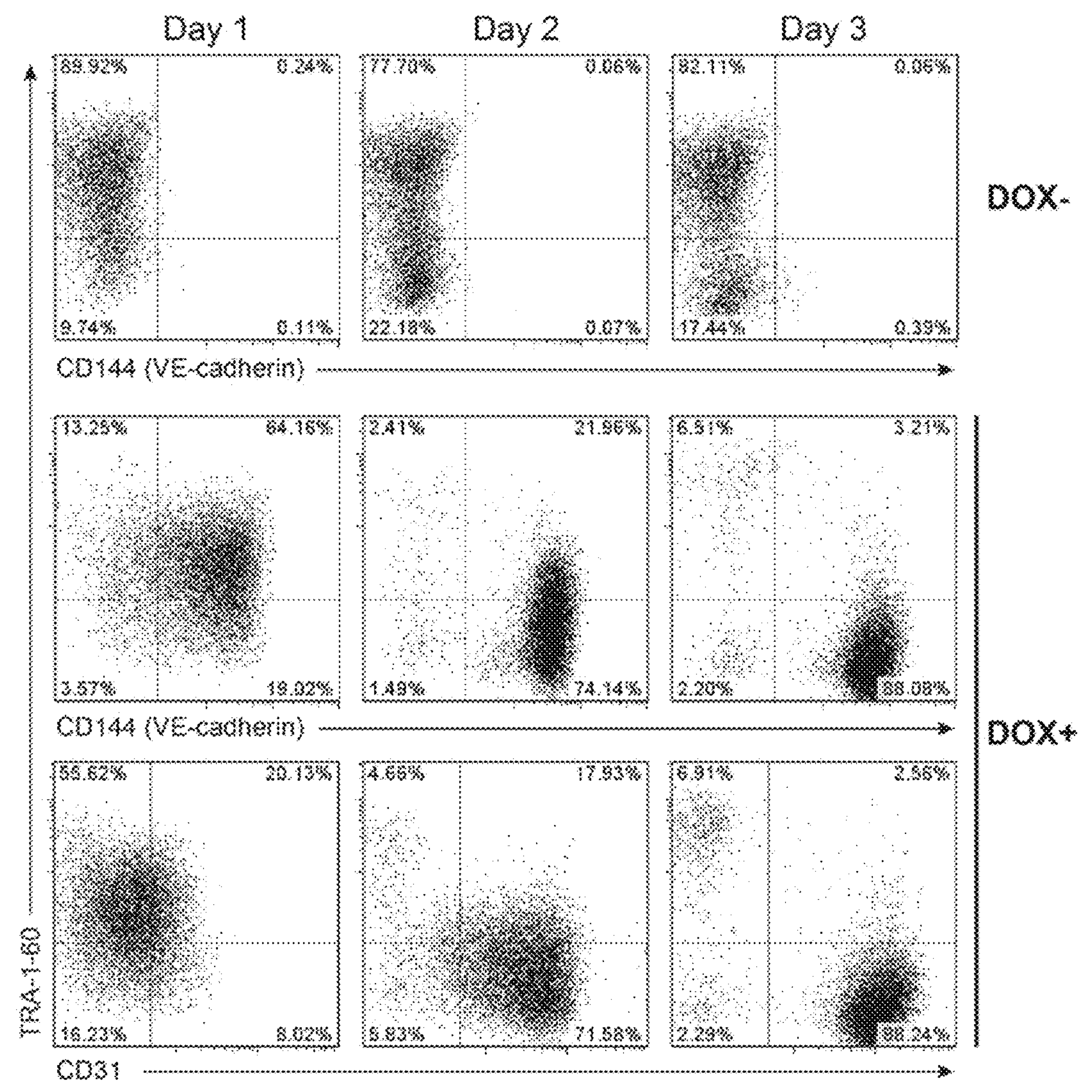
FIG. 8. Flow cytometric expression analysis of the human pluripotent stem cell-specific marker TRA-1-60 and the EC markers (CD144/VE-cadherin and CD31) during ETV2-induced EC differentiation from human ESCs. The ETV2-induced differentiated cells up-regulated the expression of the EC markers (CD144 and CD31), while down-regulated the expression of the human pluripotent stem cell marker TRA-1-60.
Figure 9:
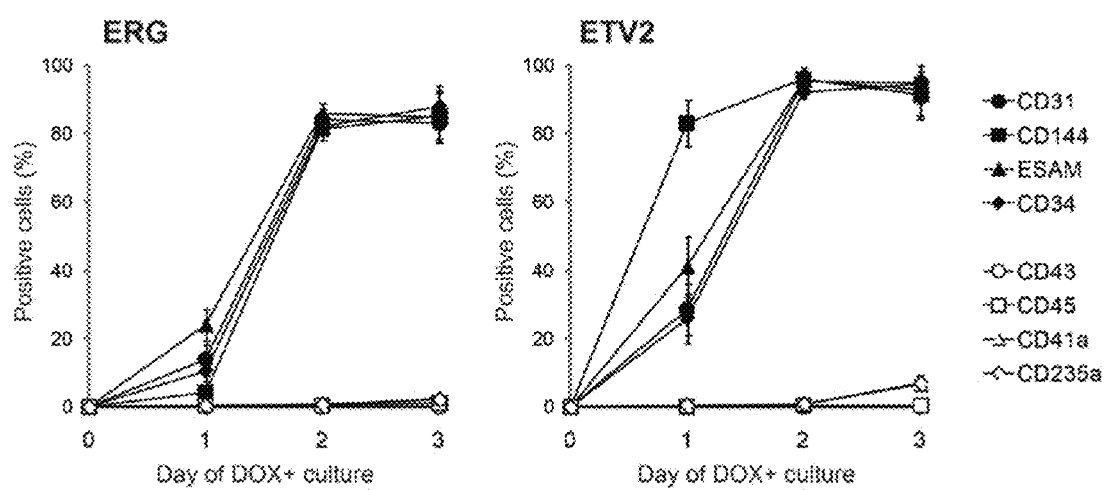
FIG. 9. Kinetic analysis of the expression of EC markers (CD31, CD144, ESAM, CD34) and hematopoietic markers (CD43, CD45, CD41a, CD235a) in ERG- and ETV2-induced hESC cultures.

Flow cytometric expression analysis of markers in forward programmed ECs. The ERG-3-induced differentiated cells up-regulated the expression of the EC markers (CD144 and CD31), while down-regulating the expression of the human pluripotent stem cell marker TRA-1-60 (FIG. 7). The ETV2-induced differentiated cells up-regulated the expression of the EC markers (CD144 and CD31), while down-regulated the expression of the human pluripotent stem cell marker TRA-1-60. (FIG. 8). Over time ERG-3-induced ECs and ETV2-induced ECs increased expression of EC markers (CD31, CD144, ESAM, CD34) but not hematopoietic markers (CD43, CD45, CD41a, CD235a) (FIG. 9).

Figure 10:
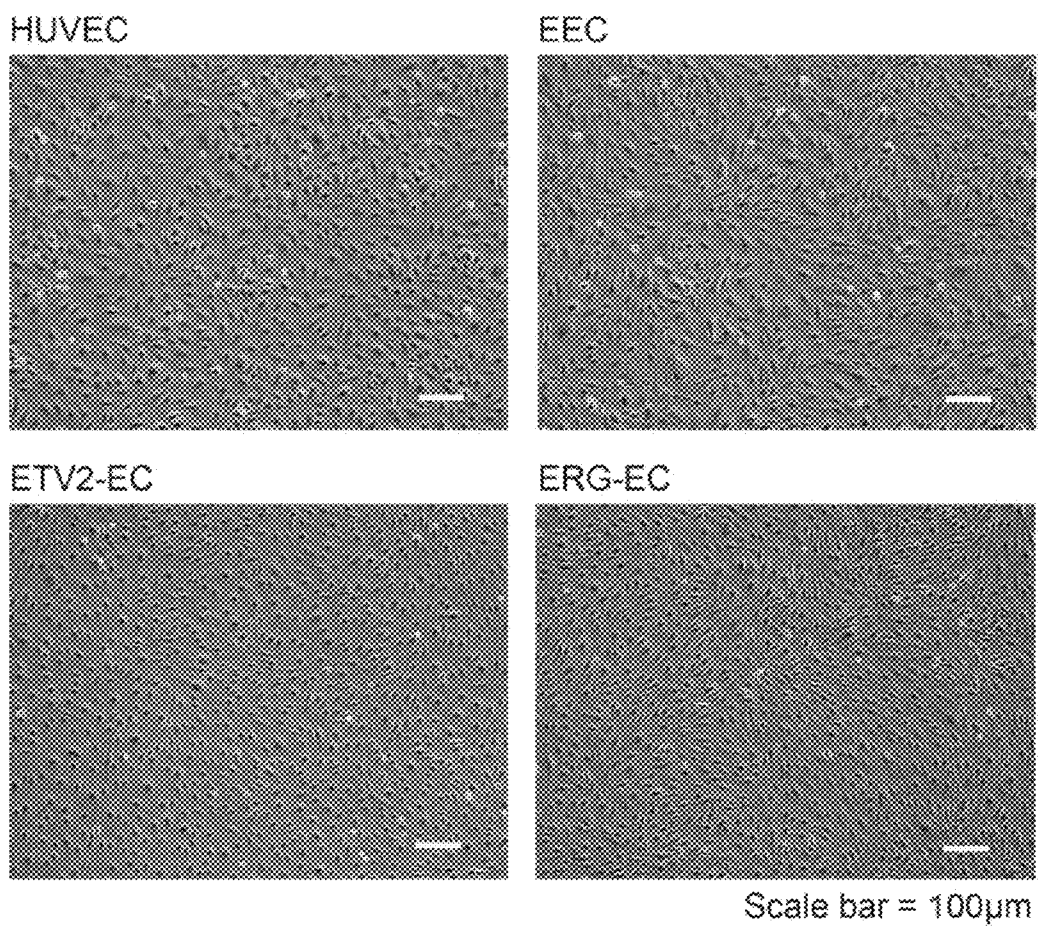
FIG. 10. Bright-field images of established ECs obtained from human ESCs either through normal differentiation (EEC) or via the expression of ERG (ERG-EC) or ETV2 (ETV2-EC). Cell cultures on day 3 of induction were dissociated into single-cell suspension by Accutase treatment (Invitrogen) and plated on gelatin-coated plastic in ESFM supplemented with 10 ng/ml basic FGF. After 2 hours of plating, medium containing non-adherent cells was removed and attached cells were cultured in ESFM supplemented with 10 ng/ml basic FGF and 5 μg/ml human fibronectin (Invitrogen). The morphology of ERG-ECs and ETV2-ECs was highly similar to that of HUVEC and EECs.

Comparison of forward programming to normal differentiation. Cell cultures on day 3 of induction were dissociated into single-cell suspension by Accutase treatment (Invitrogen) and plated on gelatin-coated plastic in ESFM supplemented with 10 ng/ml basic FGF. After 2 hours of plating, medium containing non-adherent cells was removed and attached cells were cultured in ESFM supplemented with 10 ng/ml basic FGF and 5 μg/ml human fibronectin (Invitrogen). The morphology of ERG-3-ECs and ETV2-ECs was highly similar to that of HUVEC and EECs (FIG. 10).

Figure 11:
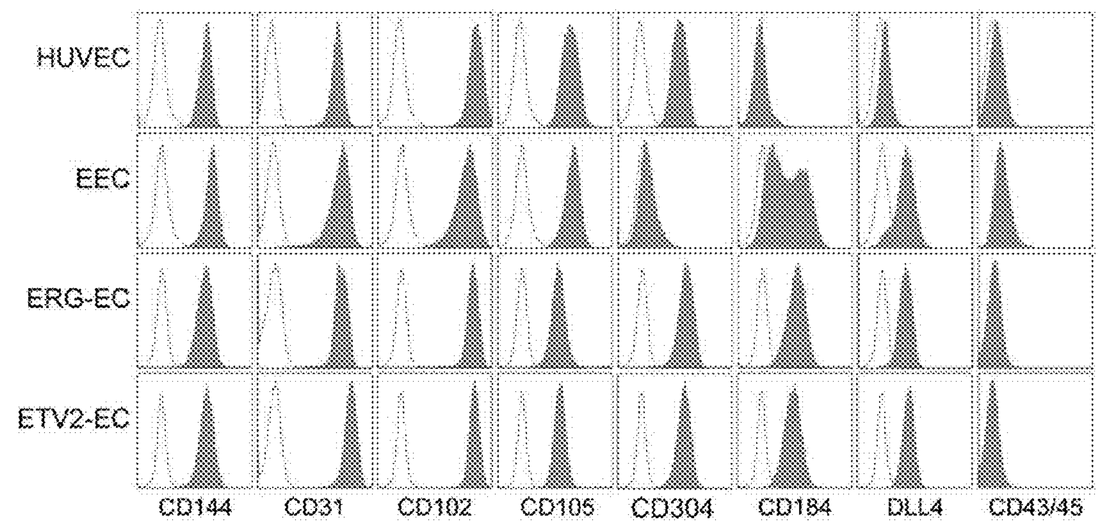
FIG. 11. Flow cytometric expression analysis of EC and hematopoietic markers. The expression of all three markers for arterial ECs (CD304/NRP1, CD184/CXCR4 and DLL4) in ERG-ECs and ETV2-ECs might suggest an arterial fate of these induced ECs, different from HUVEC and EECs.

Flow cytometric analysis of arterial EC markers. The expression of all three markers for arterial ECs (CD304/NRP1, CD184 and DLL4) in ERG-3-ECs and ETV2-ECs suggests an arterial fate of these induced ECs, different from HUVEC and EECs (FIG. 11).

Figure 12:
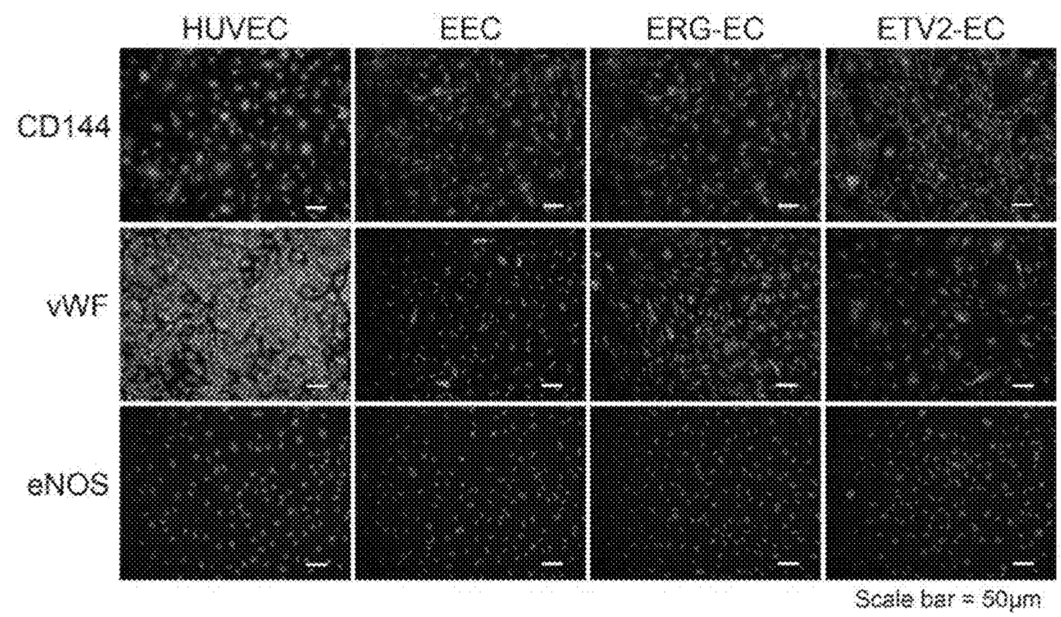
FIG. 12. Immunofluorescence analysis of ERG-ECs and ETV2-ECs: CD144, vWF and eNOS. DAPI was used to counterstain the nuclei. Although the staining was generally weaker than in HUVEC, vWF was clearly expressed in both ERG-ECs and ETV2-ECs.

Analysis of markers found in HUVEC. ERG-3-ECs and ETV2-ECs show a similar staining pattern for CD144, vWF, and eNOS as compared to HUVEC (FIG. 12). DAPI was used to counterstain the nuclei. Although the staining was generally weaker than in HUVEC, vWF was clearly expressed in both ERG-3-ECs and ETV2-ECs.

Figure 13:
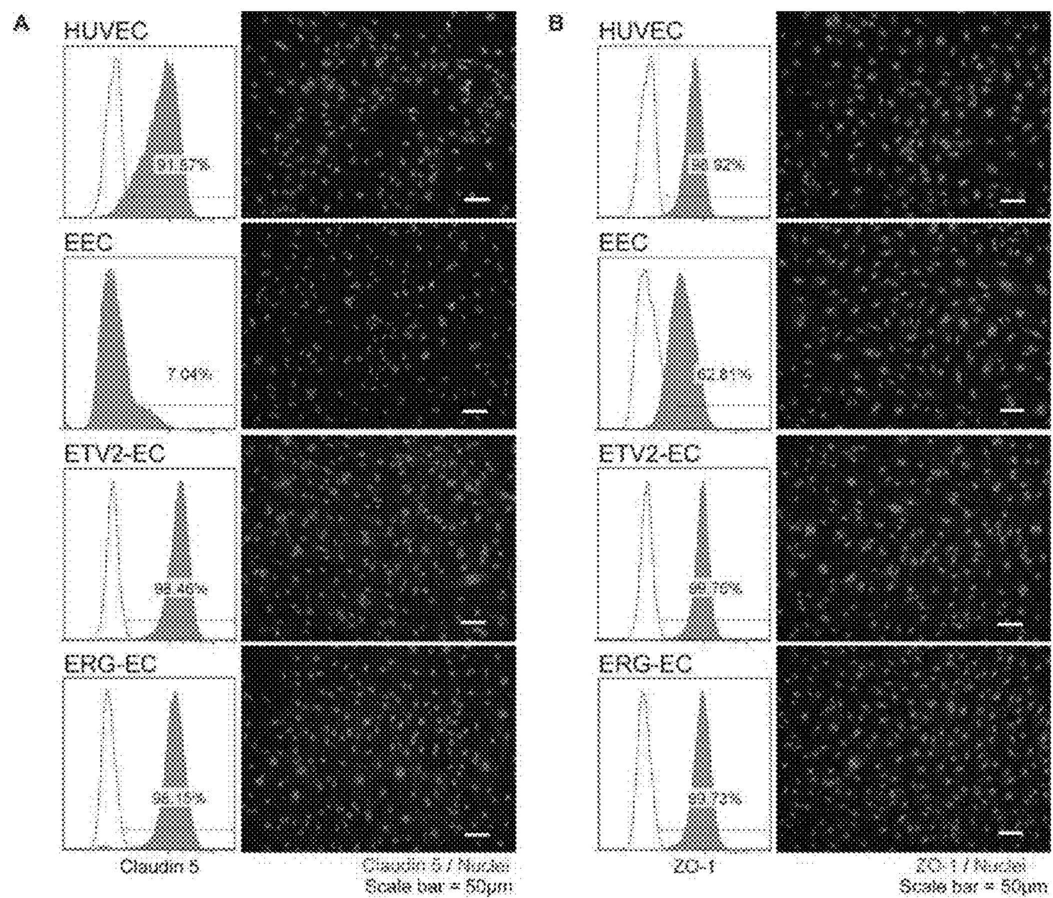
FIG. 13. Flow cytometric and Immunofluorescence analysis of tight junction proteins (Claudin 5 and ZO-1) expression in ERG-ECs and ETV2-ECs.

Analysis of proteins found in tight junctions. Tight junction proteins Claudin 5 and ZO-1 are expressed in ERG-3-ECs and ETV2-ECs (FIG. 13).

Figure 14:
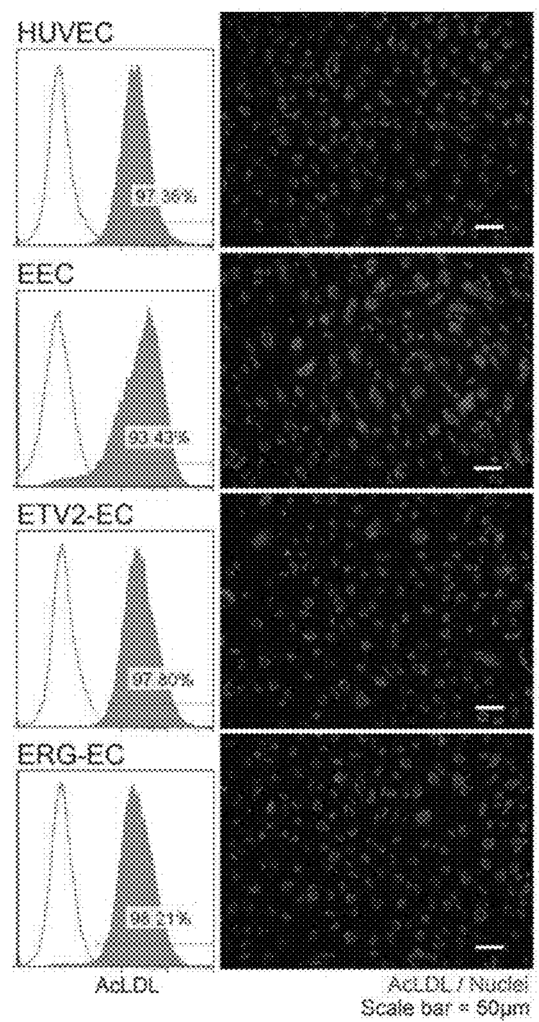
FIG. 14. Ac-LDL incorporation by ERG-ECs and ETV2-ECs. ECs were incubated with AcLDL-Dil conjugate (Invitrogen, 2 μg/ml) for 4 hours at 37° C., followed by incubation with 0.5 μg/ml Hoechst 33258 for 5 minutes for counterstaining. For flow cytometric analysis, the Ac-LDL-treated cultures were cultured in fresh medium overnight prior to Accutase dissociation. Non-treated ECs were used as control.
Figure 15:
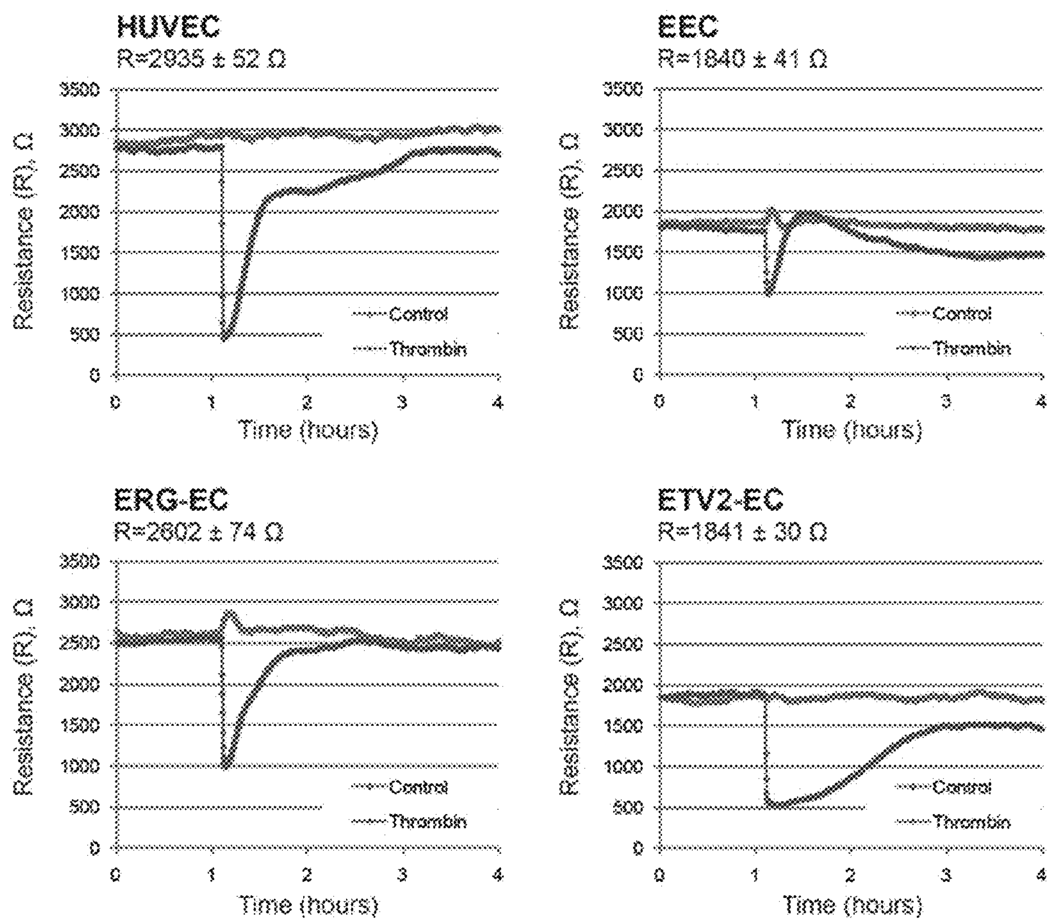
FIG. 15. Barrier function analysis of ERG-ECs and ETV2-ECs by measuring their transendothelial resistance (TER) using the ECIS ZΘinstrument (Applied Biophysics). The upper line shows the baseline TER, while the lower line shows the disruption and recovery of barrier function in response to thrombin (0.5 U/ml). The ERG-ECs showed similar kinetics in barrier function recovery as compared to HUVEC, while the ETV2-ECs were slower, suggesting that the ERG-ECs and ETV2-ECs are different.
Figure 16:
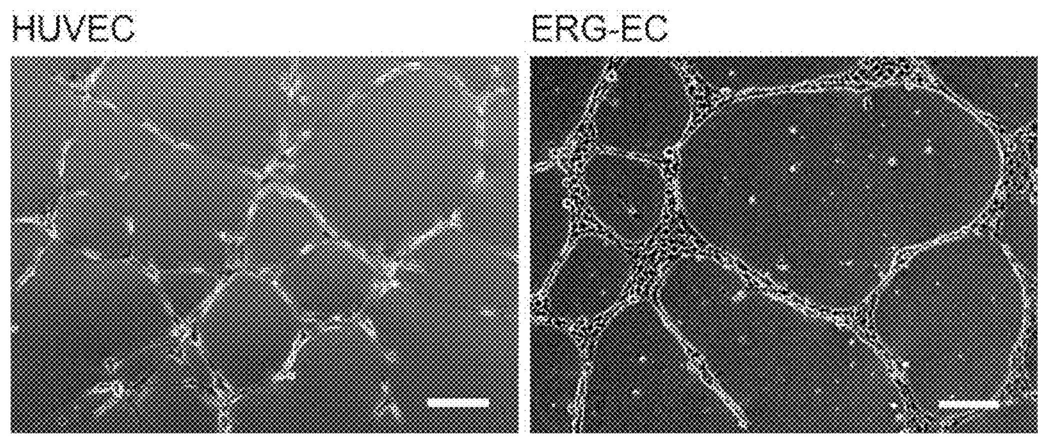
FIG. 16. Tube formation by ERG-induced ECs. ERG-ECs were plated on the solidified matrigel at 25000 cells/cm2 in ESFM supplemented with 40 ng/ml VEGF and incubated 12 hours.
Figure 17:
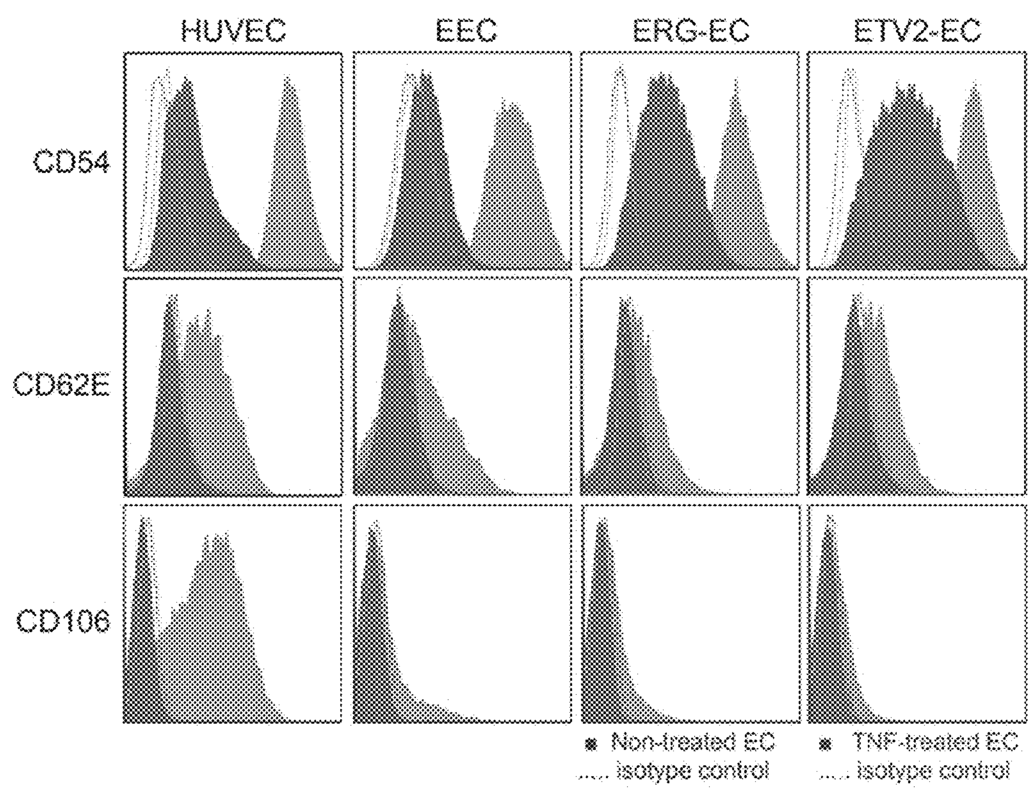
FIG. 17. Inflammatory responses of ERG-ECs and ETV2-ECs by increased expression of CD54, CD62E and CD106 activation markers in response to TNF treatment. EC cultures were treated with 25 ng/ml TNF for 24 hours and analyzed by flow cytometry.

Forward programmed ECs exhibit EC functional characteristics. Ac-LDL was incorporated by ERG-3-ECs and ETV2-ECs (FIG. 14). ECs were incubated with AcLDL-Dil conjugate (Invitrogen, 2 μg/ml) for 4 hours at 37° C., followed by incubation with 0.5 μg/ml Hoechst 33258 for 5 minutes for counterstaining. For flow cytometric analysis, the Ac-LDL-treated cultures were cultured in fresh medium overnight prior to accutase dissociation. Non-treated ECs were used as control. A barrier function test revealed that ERG-3-ECs are similar to HUVEC (FIG. 15). In particular, ERG-3-ECs showed similar kinetics in barrier function recovery as compared to HUVEC, while the ETV2-ECs were slower, suggesting that the ERG-3-ECs and ETV2-ECs are different with regard to barrier function. ERG-3-ECs were also similar to HUVEC in their ability to form tubes when plated on solidified matrigel (FIG. 16).

Figure 18:
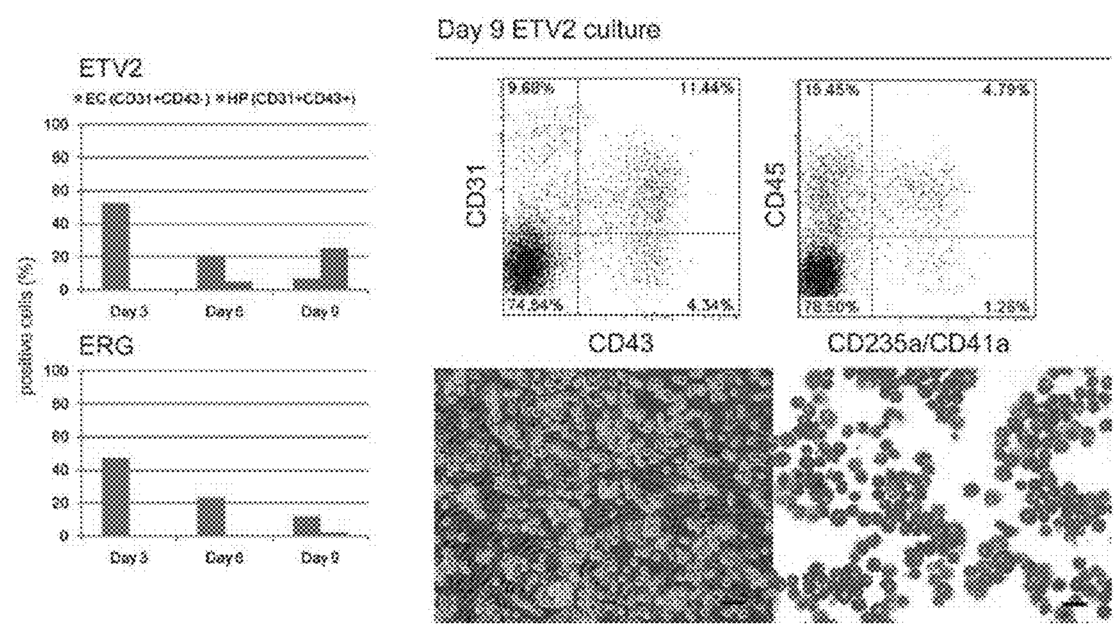
FIG. 18. Hemogenic function of ETV2-ECs. ETV2 and ERG induction was performed in medium containing 50% ESFM, 50% StemLine HSC medium (Sigma), 10 ng/ml FGF, 5 ng/ml VEGF, 50 ng/ml SCF, 20 ng/ml SCF, 10 ng/nl TPO, 10 ng/ml IL3 and 20 ng/ml IL6. Hematopoietic cells defined by CD31+CD43+ phenotype were detected in ETV2, but not in ERG-induced cultures. The majority of the hematopoietic cells in the day 9 ETV2 culture were also CD235a/CD41a-CD45+, suggesting definitive hematopoiesis.

Hemogenic function of forward programmed ECs. ETV2 and ERG-3 induction was performed in medium containing 50% ESFM, 50% StemLine HSC medium (Sigma), 10 ng/ml FGF, 5 ng/ml VEGF, 50 ng/ml SCF, 20 ng/ml SCF, 10 ng/nl TPO, 10 ng/ml IL3 and 20 ng/ml IL6. Hematopoietic cells (defined by CD31+CD43+ phenotype) were detected in ETV2, but not in ERG-3-induced cultures (FIG. 18). The majority of the hematopoietic cells in the day 9 ETV2 culture were also CD235a/CD41a-CD45+, suggesting definitive hematopoiesis.

Figure 19:
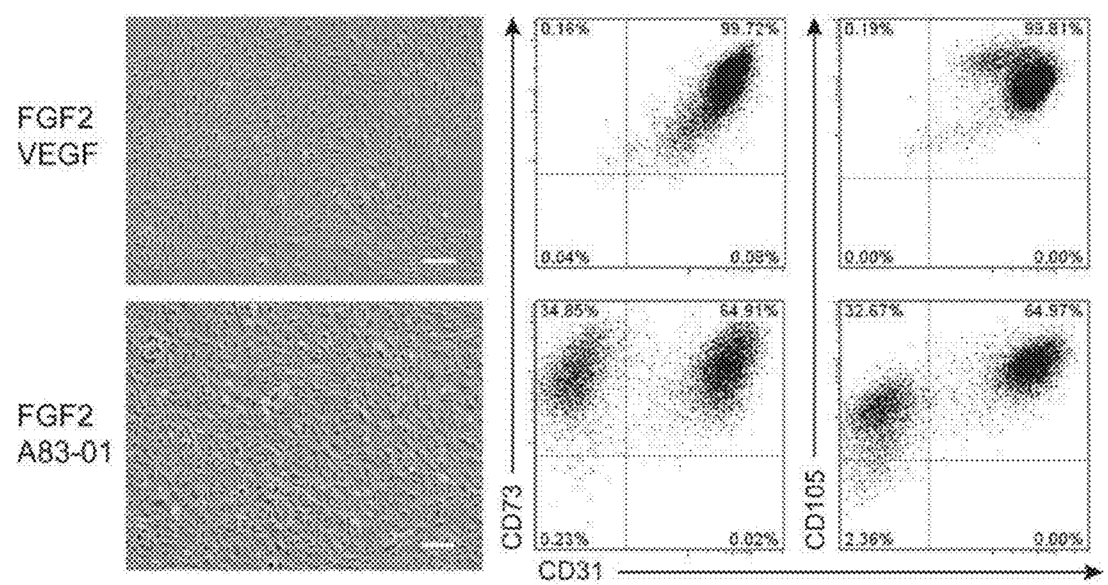
FIG. 19. Mesenchymogenic potential of ERG-ECs. ERG-ECs were cultured in ESFM containing 10 ng/ml FGF2 and additionally supplemented either with 20 ng/ml VEGF or with 1 μm A83-01 (TGFβ inhibitor). Gradual transition of ERG-EC to mesenchymal cells defined by CD31-CD73+ CD105+ phenotype was observed in cultures containing FGF+A83-01, but not FGF+VEGF. Although ETV2-EC cells undergo a similar mesenchymal transition, efficiency was lower than in ERG-EC.

Mesenchymogenic potential of forward programmed ECs. ERG-3-ECs were cultured in ESFM containing 10 ng/ml FGF2 and additionally supplemented either with 20 ng/ml VEGF or with 1 μm A83-01 (TGFβ inhibitor). Gradual transition of ERG-3-EC to mesenchymal cells (defined by CD31-CD73+CD105+ phenotype) was observed in cultures containing FGF+A83-01, but not FGF+VEGF (FIG. 19). Although ETV2-EC cells undergo a similar mesenchymal transition, efficiency was lower than in ERG-3-EC.

Example 2

Transdifferentiation into Endothelial Cells or Endothelial Precursor Cells

Similar to forward programming, endothelial cells or endothelial precursors may also be obtained via transdifferentiation from human somatic cells such as skin fibroblasts, adipose tissue-derived cells, keratinocytes, and blood cells. To identify genes that can convert somatic cells to endothelial cells or endothelial precursor cells, a lentiviral transgene delivery system will be used for the inducible expression of candidate genes (called the TET-ON system). Briefly, the cytomegalovirus (CMV) promoter will be used to drive the expression of the rtTET protein, and the candidate genes will be placed under the control of the rtTET-responsive inducible promoter (called Ptight). Both the rtTET and transgene-expressing lentivirus will be used to cotransduce cells. Doxycycline (0.2-1 μg/mL) will be added to the transduced cells to induce transgene expression, and the cell culture medium will be replaced with endothelial cell culture medium to support programming. Alternatively, the piggyBac vector system (rather than a lentiviral delivery system) may be used for the inducible expression of candidate genes.

The confirmation of endothelial cells or endothelial precursors will be carried out similarly to forward programming from hESC/iPSCs and may include morphological characteristics, cell-surface marker expression, and functional characteristics. Genes identified from forward programming from hESC/iPSCs, such as ERG and ETV2 are strong candidates for use in the transdifferentiation of human somatic cells to endothelial cells or endothelial precursors, although additional programming genes (e.g., iPSC reprogramming genes, such as OCT4) may be needed to achieve optimal programming efficiency by destabilizing the established differentiated state in the somatic cells.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,030,015
U.S. Pat. No. 5,302,523
U.S. Pat. No. 5,322,783
U.S. Pat. No. 5,384,253
U.S. Pat. No. 5,460,964

U.S. Pat. No. 5,464,765
U.S. Pat. No. 5,486,359
U.S. Pat. No. 5,486,359
U.S. Pat. No. 5,538,877
U.S. Pat. No. 5,538,880
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,635,387
U.S. Pat. No. 5,656,610
U.S. Pat. No. 5,677,136
U.S. Pat. No. 5,681,599
U.S. Pat. No. 5,702,932
U.S. Pat. No. 5,716,827
U.S. Pat. No. 5,736,396
U.S. Pat. No. 5,736,524
U.S. Pat. No. 5,750,397
U.S. Pat. No. 5,759,793
U.S. Pat. No. 5,780,448
U.S. Pat. No. 5,789,215
U.S. Pat. No. 5,811,094
U.S. Pat. No. 5,827,735
U.S. Pat. No. 5,827,740
U.S. Pat. No. 5,837,539
U.S. Pat. No. 5,837,670
U.S. Pat. No. 5,843,780
U.S. Pat. No. 5,925,565
U.S. Pat. No. 5,928,906
U.S. Pat. No. 5,935,819
U.S. Pat. No. 5,945,100
U.S. Pat. No. 5,981,274
U.S. Pat. No. 5,994,136
U.S. Pat. No. 5,994,624
U.S. Pat. No. 6,013,516
U.S. Pat. No. 6,184,038
U.S. Pat. No. 6,833,269
U.S. Pat. No. 6,991,897
U.S. Pat. No. 7,015,037
U.S. Pat. No. 7,399,632
U.S. Pat. No. 7,410,773
U.S. Pat. No. 7,410,798
U.S. Pat. No. 7,422,736
U.S. application Ser. No. 08/464,599
U.S. Appln. 61/058,858
U.S. Appln. 61/172,079
U.S. Appln. 61/184,546
U.S. Patent Publn. 2002/0102265
U.S. Patent Publn. 2003/0040038
U.S. Patent Publn. 20030211603
U.S. Patent Publn. 20070122388
U.S. Patent Publn. 20070141037
U.S. Patent Publn. 20070184122
U.S. Patent Publn. 20070238170
U.S. Patent Publn. 20070299508
U.S. Patent Publn. 20080063627
U.S. Patent Publn. 20080199843
U.S. Patent Publn. 20090149569
U.S. Patent Publn. 20090324683
U.S. Patent Publn. 20100145444
U.S. Patent Publn. 2003/0082561
U.S. Patent Publn. 20100081193
Alexander et al., *Proc. Nat. Acad. Sci. USA,* 85:5092-5096, 1988.
Alison et al, *Hepatol.,* 29:678-83, 1998.
Amit et al., *Dev. Bio.,* 227:271-278, 2000.
Andrews et al., In: *Teratocarcinomas and Embryonic Stem Cells*, Robertson (Ed.), IRL Press, 207-246, 1987.
Asoh et al., *Proc. Natl. Acad. Sci. USA,* 99(26):17107-12, 2002.
Ausubel et al., *Current Protocols in Molecular Biology*, Greene Publ. Assoc. Inc. & John Wiley & Sons, Inc., MA, 1996.
Ausubel et al., In: *Current Protocols in Molecular Biology*, John, Wiley & Sons, Inc, New York, 1994.
Bhardwaj et al., *Nat. Immunol.,* 2:172-180, 2001.
Bhatia et al., *J. Exp. Med.,* 189:1139-1148, 1999.
Blomer et al., *J. Virol.,* 71(9):6641-6649, 1997.
Boyer et al., *Cell,* 122(6):947-56, 2005.
Buss et al., *Mol. Cell. Biol.,* 8:3960-3963, 1988.
Byrne et al., *Nature,* 450(7169):497-502, 2007.
Cassiede et al., *J. Bone Miner. Res.,* 11(9):1264-1273, 1996.
Chadwick et al., *Blood,* 102(3):906-915, 2003.
Chalupowicz et al., *J. Cell Biol.,* 130(1):207-215, 1995.
Chambers et al., *Cell,* 113(5):643-55, 2003.
Chen and Okayama, *Mol. Cell Biol.,* 7(8):2745-2752, 1987.
Collins et al., *FASEB J.,* 9:899-909, 1995.
*Current Protocols in Stem Cell Biology*, Bhatia et. al. (Ed.), John Wiley and Sons, Inc., 2007.
Davidson and Zon, *Curr. Top Dev. Biol.,* 50:45-60, 2000.
Derossi et al., *J. Bio. Chem.,* 269:10444-10450, 1994.
Derossi et al., *J. Biol. Chem.,* 271:18188, 1996.
Derossi et al., *Trends in Cell Biol.,* 8:84-87, 1998.
DeVal et al., *Developmental Cell,* 16(2):180-195, 2009.
Dzau et al., *Hypertension,* 46:7-18, 2005.
Elliott and O'Hare, *Cell,* 88:223-234, 1997.
EP 1507865
EP0412700
Ercolani et al., *J. Biol. Chem.,* 263:15335-15341, 1988.
Evans, et al., In: *Cancer Principles and Practice of Oncology*, Devita et al. (Eds.), Lippincot-Raven, NY, 1054-1087, 1997.
Fawell et al., *Proc. Natl. Acad. Sci. USA,* 91:664-668, 1994.
Fechheimer et al., *Proc Natl. Acad. Sci. USA,* 84:8463-8467, 1987.
Fraley et al., *Proc. Natl. Acad. Sci. USA,* 76:3348-3352, 1979.
Frankel and Pabo, *Cell,* 55(6):1189-1193, 1988.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Gopal, *Mol. Cell Biol.,* 5:1188-1190, 1985.
Graf et al., *J. Cardiovas. Pharm.,* 20(Suppl. 9):516-820, 1992.
Graham and Van Der Eb, *Virology,* 52:456-467, 1973.
Gronthos, *Blood,* 84(12):41644173, 1994.
Hancock et al., *EMBO J.,* 10:4033-4039, 1991.
Harland and Weintraub, *J. Cell Biol.,* 101(3):1094-1099, 1985.
Hill et al., *Exp. Hematol.,* 24(8):936-943, 1996.
Ho et al., *Cancer Res.,* 61(2):474-7, 2001.
Huber et al., *Blood,* 92: 4128-4137, 1998.
*In vitro Methods in Pharmaceutical Research*, Academic Press, 1997.
Jaiswal et al., *J. Cell Biochem.,* 64(2):295-312, 1997.
Johnstone et al., 238(1):265-272, 1998.
Kaeppler et al., *Plant Cell Rep.,* 8:415-418, 1990.
Kaneda et al., *Science,* 243:375-378, 1989.
Karin et al. *Cell,* 36: 371-379, 1989.
Kato et al, *J. Biol. Chem.,* 266:3361-3364, 1991.
Kilic et al., *Stroke,* 34:1304-10, 2003.
King, et al., *Am. J. Physiol. Cell Physiol.,* 256:C1231-C1238, 1989.

Kirchmaier and Sugden, *J. Virol*., 72(6):4657-4666, 1998.
Klein et al., *Nature,* 327:70-73, 1987.
Kuzuya et al., *Arterioscl., Thromb. Vascular Biol.,* 21:765, 2001.
Langle-Rouault et al., *J. Virol.,* 72(7):6181-6185, 1998.
Levitskaya et al., *Proc. Natl. Acad. Sci. USA,* 94(23):12616-12621, 1997.
Li et al., *J. Cell Biochem.,* 106:194-199, 2009.
Lindgren et al., *Trends in Pharmacol. Sci.,* 21:99-103, 2000.
Lindner et. al., *J. Virol.,* 82(12):5693-702, 2008.
Liu et al., *Circulation Res.,* 77:638-643, 1995.
Macejak and Sarnow, *Nature,* 353:90-94, 1991.
Makino et al., *J. Clin. Invest.,* 103(5):697-705, 1999.
Maniatis, et al., *Molecular Cloning*, A Laboratory Manual, Cold Spring Harbor Press, Cold Spring Harbor, N.Y., 1988.
Mann and Frankel, *EMBO J.,* 10:1733-1739, 1991.
Mann et al., *Cell,* 33:153-159, 1983.
Manno et al., *Nat. Med.,* 12(3):342-7, 2006.
Marshall et al., *Blood,* 96:1591-1593, 2000.
McLaughlin et al., *Blood,* 98:3332-3339, 2001.
Miller et al., *Am. J. Clin. Oncol.,* 15(3):216-221, 1992.
Ming et al., *Molec. Cell. Biol.,* 22(24):8467-8477, 2002.
Nabel et al., *Science,* 244(4910):1342-1344, 1989.
Naldini et al., *Science,* 272(5259):263-267, 1996.
Ng, *Nuc. Acid Res.,* 17:601-615, 1989.
Nicolas and Rubenstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta,* 721:185-190, 1982.
Nicolau et al., *Methods Enzymol.,* 149:157-176, 1987.
Nikolova-Krstevski et al. *BMC Developmental Biology,* 9:72, 2009.
Paskind et al., *Virology,* 67:242-248, 1975.
PCT Appln. WO 03/059940
PCT Appln. WO 03/059941
PCT Appln. WO 94/09699
PCT Appln. WO 95/06128
PCT Appln. WO 96/39487
PCT Appln. WO 99/20741
PCT Appln. WO/2003/042405
Pelletier and Sonenberg, *Nature,* 334:320-325, 1988.
Potrykus et al., *Mol. Gen. Genet.,* 199(2):169-177, 1985.
Potten, *Philos. Trans. R Soc. Lond. B Biol. Sci.,* 353:821-30, 1998.
Potter et al., *Proc. Natl. Acad. Sci. USA,* 81:7161-7165, 1984.
Quitsche et al., *J. Biol. Chem.,* 264:9539-9545, 1989.
Reubinoff et al., *Nat. Biotechnol.,* 18:399B404, 2000.
Richards et al., *Cell,* 37: 263-272, 1984.
Rippe, et al., *Mol. Cell Biol.,* 10:689-695, 1990.
Rothbard et al., *Nat. Med.,* 6(11):1253-7, 2000.
Sambrook and Russell, *Molecular Cloning: A Laboratory Manual,* 3rd Ed. Cold Spring Harbor Lab. Press, 2001.
Sambrook et al., In: *Molecular Cloning: A Laboratory Manual*, Vol. 1, Cold Spring Harbor Laboratory Press, Cold Spring Harbor, N.Y., (7)7:19-17.29, 1989.
Schlaeger et al., *Proc. Natl. Acad. Sci. USA,* 94(7):3058-3063, 1997.
Schwarze et al., *Science,* 285(5433):1466-7, 1999.
Schwarze et al., *Science,* 285:1569-1572, 1999.
Smith, In: *Origins and Properties of Mouse Embryonic Stem Cells*, Annu. *Rev. Cell. Dev. Biol.,* 2000.
Takahashi and Yamanaka, *Cell,* 126:663-676, 2006.
Takahashi et al., *Cell,* 126(4):663-76, 2007.
Takahashi et al., *Cell,* 131:861-872, 2007.
Tanaka et al., *J. Immunol.,* 170(3):1291-8, 2003.
Temin, In: *Gene Transfer*, Kucherlapati (Ed.), NY, Plenum Press, 149-188, 1986.
Thomson and Marshall, *Curr. Top. Dev. Biol.,* 38:133-165, 1998.
Thomson and Odorico, *J. Trends. Biotechnol.,* 18:53-57, 2000.
Thomson et al. *Proc. Natl. Acad. Sci. USA,* 92:7844-7848, 1995.
Thomson et al., *Science,* 282:1145, 1998.
Tur-Kaspa et al., *Mol. Cell Biol.,* 6:716-718, 1986.
Vlaeminck-Guillem et al. *Mechanisms of Development,* 91: 331-335, 2009.
Voyta et al., *J. Cell Biol.,* 99:2034-2040, 1984.
Wang et al., *Nature Biotech.,* 25(3):317-318, 2007.
Watt, *Philos. Trans. R. Soc. Lond. B. Biol. Sci.,* 353:831, 1997.
Wender et al., *Proc. Natl. Acad. Sci. USA,* 97(24):13003-8, 2000.
Wilson et al., *Science,* 244:1344-1346, 1989.
Wong et al., *Gene,* 10:87-94, 1980.
Wu and Wu, *Biochemistry,* 27: 887-892, 1988.
Wu and Wu, *J. Biol. Chem.,* 262:4429-4432, 1987.
Xu et al., *Nat. Biotechnol.,* 19:971-974, 2001.
Yamamoto et al., *Eur. J. Pharmaceutics and Biopharmaceutics,* 71(3):484-89, 2009.
Yang and Russell, *Proc. Natl. Acad. Sci. USA,* 87:4144-4148, 1990.
Ying et al., *Cell,* 115:281-292, 2003.
Yoo et al., *J. Bone Joint Surg. Am.,* 80(12):1745-1757, 1998.
Yu and Thompson, *Genes Dev.,* 22(15):1987-97, 2008.
Yu et al., *Science,* 318:1917-1920, 2007.
Yu et al., *Science,* 324(5928):797-801, 2009.
Zufferey et al., *Nat. Biotechnol.,* 15(9):871-875, 1997.

What is claimed is:

1. An isolated cell population comprising human endothelial cells, wherein at least 80% of the endothelial cells comprise an exogenous expression cassette that comprises one or more endothelial programming factor genes comprising a gene encoding ETV2 or an isoform thereof and/or ERG or an isoform thereof.

2. An isolated cell population comprising human endothelial progenitor cells, wherein at least 80% of the endothelial progenitor cells comprise an exogenous expression cassette that comprises one or more endothelial programming factor genes comprising a gene encoding ETV2 or an isoform thereof and/or ERG or an isoform thereof.

3. The isolated cell population of claim 1 or 2, wherein said endothelial cells or progenitors express an ETV2, ERG, and/or isoforms thereof polypeptide encoded by said expression cassette.

4. The isolated cell population of claim 1 or 2, wherein said endothelial cells or progenitors express an ETV2, ERG, and/or isoforms thereof RNA encoded by said expression cassette.

5. The isolated cell population of claim 1 or 2, wherein the endothelial cells or progenitors express an ERG or an isoform thereof.

6. The isolated cell population of claim 5, wherein the ERG or isoform thereof is ERG isoform 3.

7. The isolated cell population of claim 1 or 2, wherein the endothelial cells or progenitors express an ETV2 or an isoform thereof.

* * * * *

SEQUENCE LISTING

```
<160> NUMBER OF SEQ ID NOS: 18

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Arg Lys Lys Arg Arg Gln Arg Arg Arg
1               5
```

```
<210> SEQ ID NO 2
<211> LENGTH: 11
<212> TYPE: PRT
<213> ORGANISM: Artificial Sequence
<220> FEATURE:
<223> OTHER INFORMATION: Synthetic peptide

<400> SEQUENCE: 2

Tyr Gly Arg Lys Lys Arg Arg Gln Arg Arg Arg
1               5                   10


<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Ala Lys Ile Trp Phe Gln Asn Arg Arg Met Lys Trp Lys Lys Glu Asn
1               5                   10                  15

Asn


<210> SEQ ID NO 4
<211> LENGTH: 34
<212> TYPE: PRT
<213> ORGANISM: Artificial Sequence
<220> FEATURE:
<223> OTHER INFORMATION: Synthetic peptide

<400> SEQUENCE: 4

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu


<210> SEQ ID NO 5
<211> LENGTH: 11
<212> TYPE: PRT
<213> ORGANISM: Artificial Sequence
<220> FEATURE:
<223> OTHER INFORMATION: Synthetic peptide

<400> SEQUENCE: 5

Tyr Ala Arg Lys Ala Arg Arg Gln Ala Arg Arg
1               5                   10


<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

Tyr Ala Arg Ala Ala Arg Arg Ala Ala Arg Arg
1               5                   10


<210> SEQ ID NO 7
<211> LENGTH: 11
<212> TYPE: PRT
<213> ORGANISM: Artificial Sequence
<220> FEATURE:
<223> OTHER INFORMATION: Synthetic peptide
```

<400> SEQUENCE: 7

```
Tyr Ala Arg Ala Ala Arg Arg Ala Ala Arg Ala
1               5                   10
```

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

```
Tyr Ala Arg Ala Ala Ala Arg Gln Ala Arg Ala
1               5                   10
```

<210> SEQ ID NO 9
<211> LENGTH: 5042
<212> TYPE: DNA
<213> ORGANISM: Homo sapiens
<220> FEATURE:
<221> NAME/KEY: CDS
<222> LOCATION: (273)..(1661)

<400> SEQUENCE: 9

```
gttttcactt ggtcggaatg gggagagtgt gcaagagatc gctgcgggac aggttcctag     60

agatcgctcc gggacggtcg tgacggcccc cgagggacat gagagaagag gagcggcgct    120

caggttattc caggatcttt ggagacccga ggaaagccgt gttgaccaaa agcaagacaa    180

atgactcaca gagaaaaaag atggcagaac caagggcaac taaagccgtc aggttctgaa    240

cagctggtag atgggctggc ttactgaagg ac atg att cag act gtc ccg gac      293
                                    Met Ile Gln Thr Val Pro Asp
                                    1               5

cca gca gct cat atc aag gaa gcc tta tca gtt gtg agt gag gac cag      341
Pro Ala Ala His Ile Lys Glu Ala Leu Ser Val Val Ser Glu Asp Gln
        10                  15                  20

tcg ttg ttt gag tgt gcc tac gga acg cca cac ctg gct aag aca gag      389
Ser Leu Phe Glu Cys Ala Tyr Gly Thr Pro His Leu Ala Lys Thr Glu
    25                  30                  35

atg acc gcg tcc tcc tcc agc gac tat gga cag act tcc aag atg agc      437
Met Thr Ala Ser Ser Ser Ser Asp Tyr Gly Gln Thr Ser Lys Met Ser
40                  45                  50                  55

cca cgc gtc cct cag cag gat tgg ctg tct caa ccc cca gcc agg gtc      485
Pro Arg Val Pro Gln Gln Asp Trp Leu Ser Gln Pro Pro Ala Arg Val
                60                  65                  70

acc atc aaa atg gaa tgt aac cct agc cag gtg aat ggc tca agg aac      533
Thr Ile Lys Met Glu Cys Asn Pro Ser Gln Val Asn Gly Ser Arg Asn
            75                  80                  85

tct cct gat gaa tgc agt gtg gcc aaa ggc ggg aag atg gtg ggc agc      581
Ser Pro Asp Glu Cys Ser Val Ala Lys Gly Gly Lys Met Val Gly Ser
        90                  95                  100

cca gac acc gtt ggg atg aac tac ggc agc tac atg gag gag aag cac      629
Pro Asp Thr Val Gly Met Asn Tyr Gly Ser Tyr Met Glu Glu Lys His
    105                 110                 115

atg cca ccc cca aac atg acc acg aac gag cgc aga gtt atc gtg cca      677
Met Pro Pro Pro Asn Met Thr Thr Asn Glu Arg Arg Val Ile Val Pro
120                 125                 130                 135

gca gat cct acg cta tgg agt aca gac cat gtg cgg cag tgg ctg gag      725
Ala Asp Pro Thr Leu Trp Ser Thr Asp His Val Arg Gln Trp Leu Glu
                140                 145                 150
```

```
tgg gcg gtg aaa gaa tat ggc ctt cca gac gtc aac atc ttg tta ttc      773
Trp Ala Val Lys Glu Tyr Gly Leu Pro Asp Val Asn Ile Leu Leu Phe
            155                 160                 165

cag aac atc gat ggg aag gaa ctg tgc aag atg acc aag gac gac ttc      821
Gln Asn Ile Asp Gly Lys Glu Leu Cys Lys Met Thr Lys Asp Asp Phe
        170                 175                 180

cag agg ctc acc ccc agc tac aac gcc gac atc ctt ctc tca cat ctc      869
Gln Arg Leu Thr Pro Ser Tyr Asn Ala Asp Ile Leu Leu Ser His Leu
    185                 190                 195

cac tac ctc aga gag act cct ctt cca cat ttg act tca gat gat gtt      917
His Tyr Leu Arg Glu Thr Pro Leu Pro His Leu Thr Ser Asp Asp Val
200                 205                 210                 215

gat aaa gcc tta caa aac tct cca cgg tta atg cat gct aga aac aca      965
Asp Lys Ala Leu Gln Asn Ser Pro Arg Leu Met His Ala Arg Asn Thr
                220                 225                 230

gat tta cca tat gag ccc ccc agg aga tca gcc tgg acc ggt cac ggc     1013
Asp Leu Pro Tyr Glu Pro Pro Arg Arg Ser Ala Trp Thr Gly His Gly
            235                 240                 245

cac ccc acg ccc cag tcg aaa gct gct caa cca tct cct tcc aca gtg     1061
His Pro Thr Pro Gln Ser Lys Ala Ala Gln Pro Ser Pro Ser Thr Val
        250                 255                 260

ccc aaa act gaa gac cag cgt cct cag tta gat cct tat cag att ctt     1109
Pro Lys Thr Glu Asp Gln Arg Pro Gln Leu Asp Pro Tyr Gln Ile Leu
    265                 270                 275

gga cca aca agt agc cgc ctt gca aat cca ggc agt ggc cag atc cag     1157
Gly Pro Thr Ser Ser Arg Leu Ala Asn Pro Gly Ser Gly Gln Ile Gln
280                 285                 290                 295

ctt tgg cag ttc ctc ctg gag ctc ctg tcg gac agc tcc aac tcc agc     1205
Leu Trp Gln Phe Leu Leu Glu Leu Leu Ser Asp Ser Ser Asn Ser Ser
                300                 305                 310

tgc atc acc tgg gaa ggc acc aac ggg gag ttc aag atg acg gat ccc     1253
Cys Ile Thr Trp Glu Gly Thr Asn Gly Glu Phe Lys Met Thr Asp Pro
            315                 320                 325

gac gag gtg gcc cgg cgc tgg gga gag cgg aag agc aaa ccc aac atg     1301
Asp Glu Val Ala Arg Arg Trp Gly Glu Arg Lys Ser Lys Pro Asn Met
        330                 335                 340

aac tac gat aag ctc agc cgc gcc ctc cgt tac tac tat gac aag aac     1349
Asn Tyr Asp Lys Leu Ser Arg Ala Leu Arg Tyr Tyr Tyr Asp Lys Asn
    345                 350                 355

atc atg acc aag gtc cat ggg aag cgc tac gcc tac aag ttc gac ttc     1397
Ile Met Thr Lys Val His Gly Lys Arg Tyr Ala Tyr Lys Phe Asp Phe
360                 365                 370                 375

cac ggg atc gcc cag gcc ctc cag ccc cac ccc ccg gag tca tct ctg     1445
His Gly Ile Ala Gln Ala Leu Gln Pro His Pro Pro Glu Ser Ser Leu
                380                 385                 390

tac aag tac ccc tca gac ctc ccg tac atg ggc tcc tat cac gcc cac     1493
Tyr Lys Tyr Pro Ser Asp Leu Pro Tyr Met Gly Ser Tyr His Ala His
            395                 400                 405

cca cag aag atg aac ttt gtg gcg ccc cac cct cca gcc ctc ccc gtg     1541
Pro Gln Lys Met Asn Phe Val Ala Pro His Pro Pro Ala Leu Pro Val
        410                 415                 420

aca tct tcc agt ttt ttt gct gcc cca aac cca tac tgg aat tca cca     1589
Thr Ser Ser Ser Phe Phe Ala Ala Pro Asn Pro Tyr Trp Asn Ser Pro
    425                 430                 435

act ggg ggt ata tac ccc aac act agg ctc ccc acc agc cat atg cct     1637
Thr Gly Gly Ile Tyr Pro Asn Thr Arg Leu Pro Thr Ser His Met Pro
440                 445                 450                 455

tct cat ctg ggc act tac tac taa agacctggcg gaggcttttc ccatcagcgt     1691
Ser His Leu Gly Thr Tyr Tyr
                460
```

-continued

```
gcattcacca gcccatcgcc acaaactcta tcggagaaca tgaatcaaaa gtgcctcaag   1751
aggaatgaaa aaagctttac tggggctggg gaaggaagcc ggggaagaga tccaaagact   1811
cttgggaggg agttactgaa gtcttactac agaaatgagg aggatgctaa aaatgtcacg   1871
aatatggaca tatcatctgt ggactgacct tgtaaaagac agtgtatgta gaagcatgaa   1931
gtcttaagga caaagtgcca aagaaagtgg tcttaagaaa tgtataaact ttagagtaga   1991
gtttggaatc ccactaatgc aaactgggat gaaactaaag caatagaaac aacacagttt   2051
tgacctaaca taccgtttat aatgccattt taaggaaaac tacctgtatt taaaaataga   2111
aacatatcaa aaacaagaga aaagacacga gagagactgt ggcccatcaa cagacgttga   2171
tatgcaactg catggcatgt gctgttttgg ttgaaatcaa atacattccg tttgatggac   2231
agctgtcagc tttctcaaac tgtgaagatg acccaaagtt tccaactcct ttacagtatt   2291
accgggacta tgaactaaaa ggtgggactg aggatgtgta tagagtgagc gtgtgattgt   2351
agacagaggg gtgaagaagg aggaggaaga ggcagagaag gaggagacca gggctgggaa   2411
agaaacttct caagcaatga agactggact caggacattt ggggactgtg tacaatgagt   2471
tatggagact cgagggttca tgcagtcagt gttataccaa acccagtgtt aggagaaagg   2531
acacagcgta atggagaaag gggaagtagt agaattcaga aacaaaaatg cgcatctctt   2591
tctttgtttg tcaaatgaaa attttaactg gaattgtctg atatttaaga gaaacattca   2651
ggacctcatc attatgtggg ggctttgttc tccacagggt caggtaagag atggccttct   2711
tggctgccac aatcagaaat cacgcaggca ttttgggtag gcggcctcca gttttccttt   2771
gagtcgcgaa cgctgtgcgt ttgtcagaat gaagtataca agtcaatgtt tttcccctt    2831
tttatataat aattatataa cttatgcatt tatacactac gagttgatct cggccagcca   2891
aagacacacg acaaaagaga caatcgatat aatgtggcct tgaattttaa ctctgtatgc   2951
ttaatgttta caatatgaag ttattagttc ttagaatgca gaatgtatgt aataaaataa   3011
gcttggccta gcatggcaaa tcagatttat acaggagtct gcatttgcac tttttttagt   3071
gactaaagtt gcttaatgaa aacatgtgct gaatgttgtg gattttgtgt tataatttac   3131
tttgtccagg aacttgtgca agggagagcc aaggaaatag gatgtttggc acccaaatgg   3191
cgtcagcctc tccaggtcct tcttgcctcc cctcctgtct tttatttcta gcccctttttg  3251
gaacagaagg accccgggtt tcacattgga gcctccatat ttatgcctgg aatggaaaga   3311
ggcctatgaa gctggggttg tcattgagaa attctagttc agcacctggt cacaaatcac   3371
ccttaattcc tgctatgatt aaaatacatt tgttgaacag tgaacaagct accactcgta   3431
aggcaaactg tattattact ggcaaataaa gcgtcatgga tagctgcaat ttctcacttt   3491
acagaaacaa gggataacgt ctagatttgc tgcggggttt ctctttcagg agctctcact   3551
aggtagacag ctttagtcct gctacatcag agttacctgg gcactgtggc ttgggattca   3611
ctagccctga gcctgatgtt gctggctatc ccttgaagac aatgtttatt tccataatct   3671
agagtcagtt tccctgggca tcttttcttt gaatcacaaa tgctgccaac cttggtccag   3731
gtgaaggcaa ctcaaaaggt gaaaatacaa ggtgaccgtg cgaaggcgct agccgaaaca   3791
tcttagctga ataggtttct gaactggccc ttttcatagc tgtttcaggg cctgtttttt   3851
tcacgttgca gtccttttgc tatgattatg tgaagttgcc aaacctctgt gctgtggatg   3911
ttttggcagt gggctttgaa gtcggcagga cacgattacc aatgctcctg acaccccgtg   3971
tcatttggat tagacggagc ccaaccatcc atcattttgc agcagcctgg gaaggcccac   4031
aaagtgcccg tatctcctta gggaaaataa ataaatacaa tcatgaaagc tggcagttag   4091
```

```
gctgacccaa actgtgctaa tggaaaagat cagtcatttt tattttggaa tgcaaagtca   4151

agacacacct acattcttca tagaaataca catttacttg gataatcact cagttctctc   4211

ttcaagactg tctcatgagc aagatcataa aaacaagaca tgattatcat attcaatttt   4271

aacagatgtt ttccattaga tccctcaacc ctccaccccc agtccaggtt attagcaagt   4331

cttatgagca actgggataa ttttggataa catgataata ctgagttcct tcaaatacat   4391

aattcttaaa ttgtttcaaa atggcattaa ctctctgtta ctgttgtaat ctaattccaa   4451

agccccctcc aggtcatatt cataattgca tgaacctttt ctctctgttt gtccctgtct   4511

cttggcttgc cctgatgtat actcagactc ctgtacaatc ttactcctgc tggcaagaga   4571

tttgtcttct tttcttgtct tcaattggct ttcgggcctt gtatgtggta aaatcaccaa   4631

atcacagtca agactgtgtt tttgttccta gtttgatgcc cttatgtccc ggaggggttc   4691

acaaagtgct ttgtcaggac tgctgcagtt agaaggctca ctgcttctcc taagccttct   4751

gcacagatgt ggcacctgca acccaggagc aggagccgga ggagctgccc tctgacagca   4811

ggtgcagcag agatggctac agctcaggag ctgggaaggt gatggggcac agggaaagca   4871

cagatgttct gcagcgcccc aaagtgaccc attgcctgga gaaagagaag aaaatatttt   4931

ttaaaaagct agtttattta gcttctcatt aattcattca aataaagtcg tgaggtgact   4991

aattagagaa taaaaattac tttggactac tcaaaaatac accaaaaaaa a            5042
```

<210> SEQ ID NO 10
<211> LENGTH: 462
<212> TYPE: PRT
<213> ORGANISM: Homo sapiens

<400> SEQUENCE: 10

```
Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30

Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205
```

```
His Leu Thr Ser Asp Asp Val Asp Lys Ala Leu Gln Asn Ser Pro Arg
    210                 215                 220

Leu Met His Ala Arg Asn Thr Asp Leu Pro Tyr Glu Pro Pro Arg Arg
225                 230                 235                 240

Ser Ala Trp Thr Gly His Gly His Pro Thr Pro Gln Ser Lys Ala Ala
                245                 250                 255

Gln Pro Ser Pro Ser Thr Val Pro Lys Thr Glu Asp Gln Arg Pro Gln
            260                 265                 270

Leu Asp Pro Tyr Gln Ile Leu Gly Pro Thr Ser Ser Arg Leu Ala Asn
        275                 280                 285

Pro Gly Ser Gly Gln Ile Gln Leu Trp Gln Phe Leu Leu Glu Leu Leu
    290                 295                 300

Ser Asp Ser Ser Asn Ser Ser Cys Ile Thr Trp Glu Gly Thr Asn Gly
305                 310                 315                 320

Glu Phe Lys Met Thr Asp Pro Asp Glu Val Ala Arg Arg Trp Gly Glu
                325                 330                 335

Arg Lys Ser Lys Pro Asn Met Asn Tyr Asp Lys Leu Ser Arg Ala Leu
            340                 345                 350

Arg Tyr Tyr Tyr Asp Lys Asn Ile Met Thr Lys Val His Gly Lys Arg
        355                 360                 365

Tyr Ala Tyr Lys Phe Asp Phe His Gly Ile Ala Gln Ala Leu Gln Pro
    370                 375                 380

His Pro Pro Glu Ser Ser Leu Tyr Lys Tyr Pro Ser Asp Leu Pro Tyr
385                 390                 395                 400

Met Gly Ser Tyr His Ala His Pro Gln Lys Met Asn Phe Val Ala Pro
                405                 410                 415

His Pro Pro Ala Leu Pro Val Thr Ser Ser Ser Phe Phe Ala Ala Pro
            420                 425                 430

Asn Pro Tyr Trp Asn Ser Pro Thr Gly Gly Ile Tyr Pro Asn Thr Arg
        435                 440                 445

Leu Pro Thr Ser His Met Pro Ser His Leu Gly Thr Tyr Tyr
    450                 455                 460


<210> SEQ ID NO 11
<211> LENGTH: 5114
<212> TYPE: DNA
<213> ORGANISM: Homo sapiens
<220> FEATURE:
<221> NAME/KEY: CDS
<222> LOCATION: (273)..(1733)

<400> SEQUENCE: 11

gttttcactt ggtcggaatg gggagagtgt gcaagagatc gctgcgggac aggttcctag      60

agatcgctcc gggacggtcg tgacggcccc cgagggacat gagagaagag gagcggcgct     120

caggttattc caggatcttt ggagacccga ggaaagccgt gttgaccaaa agcaagacaa     180

atgactcaca gagaaaaaag atggcagaac caagggcaac taaagccgtc aggttctgaa     240

cagctggtag atgggctggc ttactgaagg ac atg att cag act gtc ccg gac       293
                                    Met Ile Gln Thr Val Pro Asp
                                    1               5

cca gca gct cat atc aag gaa gcc tta tca gtt gtg agt gag gac cag       341
Pro Ala Ala His Ile Lys Glu Ala Leu Ser Val Val Ser Glu Asp Gln
        10                  15                  20

tcg ttg ttt gag tgt gcc tac gga acg cca cac ctg gct aag aca gag       389
Ser Leu Phe Glu Cys Ala Tyr Gly Thr Pro His Leu Ala Lys Thr Glu
    25                  30                  35
```

```
atg acc gcg tcc tcc tcc agc gac tat gga cag act tcc aag atg agc      437
Met Thr Ala Ser Ser Ser Ser Asp Tyr Gly Gln Thr Ser Lys Met Ser
40                  45                  50                  55

cca cgc gtc cct cag cag gat tgg ctg tct caa ccc cca gcc agg gtc      485
Pro Arg Val Pro Gln Gln Asp Trp Leu Ser Gln Pro Pro Ala Arg Val
                60                  65                  70

acc atc aaa atg gaa tgt aac cct agc cag gtg aat ggc tca agg aac      533
Thr Ile Lys Met Glu Cys Asn Pro Ser Gln Val Asn Gly Ser Arg Asn
            75                  80                  85

tct cct gat gaa tgc agt gtg gcc aaa ggc ggg aag atg gtg ggc agc      581
Ser Pro Asp Glu Cys Ser Val Ala Lys Gly Gly Lys Met Val Gly Ser
        90                  95                  100

cca gac acc gtt ggg atg aac tac ggc agc tac atg gag gag aag cac      629
Pro Asp Thr Val Gly Met Asn Tyr Gly Ser Tyr Met Glu Glu Lys His
    105                 110                 115

atg cca ccc cca aac atg acc acg aac gag cgc aga gtt atc gtg cca      677
Met Pro Pro Pro Asn Met Thr Thr Asn Glu Arg Arg Val Ile Val Pro
120                 125                 130                 135

gca gat cct acg cta tgg agt aca gac cat gtg cgg cag tgg ctg gag      725
Ala Asp Pro Thr Leu Trp Ser Thr Asp His Val Arg Gln Trp Leu Glu
                140                 145                 150

tgg gcg gtg aaa gaa tat ggc ctt cca gac gtc aac atc ttg tta ttc      773
Trp Ala Val Lys Glu Tyr Gly Leu Pro Asp Val Asn Ile Leu Leu Phe
            155                 160                 165

cag aac atc gat ggg aag gaa ctg tgc aag atg acc aag gac gac ttc      821
Gln Asn Ile Asp Gly Lys Glu Leu Cys Lys Met Thr Lys Asp Asp Phe
        170                 175                 180

cag agg ctc acc ccc agc tac aac gcc gac atc ctt ctc tca cat ctc      869
Gln Arg Leu Thr Pro Ser Tyr Asn Ala Asp Ile Leu Leu Ser His Leu
    185                 190                 195

cac tac ctc aga gag act cct ctt cca cat ttg act tca gat gat gtt      917
His Tyr Leu Arg Glu Thr Pro Leu Pro His Leu Thr Ser Asp Asp Val
200                 205                 210                 215

gat aaa gcc tta caa aac tct cca cgg tta atg cat gct aga aac aca      965
Asp Lys Ala Leu Gln Asn Ser Pro Arg Leu Met His Ala Arg Asn Thr
                220                 225                 230

ggg ggt gca gct ttt att ttc cca aat act tca gta tat cct gaa gct     1013
Gly Gly Ala Ala Phe Ile Phe Pro Asn Thr Ser Val Tyr Pro Glu Ala
            235                 240                 245

acg caa aga att aca act agg cca gat tta cca tat gag ccc ccc agg     1061
Thr Gln Arg Ile Thr Thr Arg Pro Asp Leu Pro Tyr Glu Pro Pro Arg
        250                 255                 260

aga tca gcc tgg acc ggt cac ggc cac ccc acg ccc cag tcg aaa gct     1109
Arg Ser Ala Trp Thr Gly His Gly His Pro Thr Pro Gln Ser Lys Ala
    265                 270                 275

gct caa cca tct cct tcc aca gtg ccc aaa act gaa gac cag cgt cct     1157
Ala Gln Pro Ser Pro Ser Thr Val Pro Lys Thr Glu Asp Gln Arg Pro
280                 285                 290                 295

cag tta gat cct tat cag att ctt gga cca aca agt agc cgc ctt gca     1205
Gln Leu Asp Pro Tyr Gln Ile Leu Gly Pro Thr Ser Ser Arg Leu Ala
                300                 305                 310

aat cca ggc agt ggc cag atc cag ctt tgg cag ttc ctc ctg gag ctc     1253
Asn Pro Gly Ser Gly Gln Ile Gln Leu Trp Gln Phe Leu Leu Glu Leu
            315                 320                 325

ctg tcg gac agc tcc aac tcc agc tgc atc acc tgg gaa ggc acc aac     1301
Leu Ser Asp Ser Ser Asn Ser Ser Cys Ile Thr Trp Glu Gly Thr Asn
        330                 335                 340

ggg gag ttc aag atg acg gat ccc gac gag gtg gcc cgg cgc tgg gga     1349
Gly Glu Phe Lys Met Thr Asp Pro Asp Glu Val Ala Arg Arg Trp Gly
    345                 350                 355
```

```
gag cgg aag agc aaa ccc aac atg aac tac gat aag ctc agc cgc gcc     1397
Glu Arg Lys Ser Lys Pro Asn Met Asn Tyr Asp Lys Leu Ser Arg Ala
360                 365                 370                 375

ctc cgt tac tac tat gac aag aac atc atg acc aag gtc cat ggg aag     1445
Leu Arg Tyr Tyr Tyr Asp Lys Asn Ile Met Thr Lys Val His Gly Lys
                380                 385                 390

cgc tac gcc tac aag ttc gac ttc cac ggg atc gcc cag gcc ctc cag     1493
Arg Tyr Ala Tyr Lys Phe Asp Phe His Gly Ile Ala Gln Ala Leu Gln
            395                 400                 405

ccc cac ccc ccg gag tca tct ctg tac aag tac ccc tca gac ctc ccg     1541
Pro His Pro Pro Glu Ser Ser Leu Tyr Lys Tyr Pro Ser Asp Leu Pro
        410                 415                 420

tac atg ggc tcc tat cac gcc cac cca cag aag atg aac ttt gtg gcg     1589
Tyr Met Gly Ser Tyr His Ala His Pro Gln Lys Met Asn Phe Val Ala
    425                 430                 435

ccc cac cct cca gcc ctc ccc gtg aca tct tcc agt ttt ttt gct gcc     1637
Pro His Pro Pro Ala Leu Pro Val Thr Ser Ser Ser Phe Phe Ala Ala
440                 445                 450                 455

cca aac cca tac tgg aat tca cca act ggg ggt ata tac ccc aac act     1685
Pro Asn Pro Tyr Trp Asn Ser Pro Thr Gly Gly Ile Tyr Pro Asn Thr
                460                 465                 470

agg ctc ccc acc agc cat atg cct tct cat ctg ggc act tac tac taa     1733
Arg Leu Pro Thr Ser His Met Pro Ser His Leu Gly Thr Tyr Tyr
            475                 480                 485

agacctggcg gaggcttttc ccatcagcgt gcattcacca gcccatcgcc acaaactcta   1793

tcggagaaca tgaatcaaaa gtgcctcaag aggaatgaaa aaagctttac tggggctggg   1853

gaaggaagcc ggggaagaga tccaaagact cttgggaggg agttactgaa gtcttactac   1913

agaaatgagg aggatgctaa aaatgtcacg aatatggaca tatcatctgt ggactgacct   1973

tgtaaaagac agtgtatgta gaagcatgaa gtcttaagga caaagtgcca aagaaagtgg   2033

tcttaagaaa tgtataaact ttagagtaga gtttggaatc ccactaatgc aaactgggat   2093

gaaactaaag caatagaaac aacacagttt tgacctaaca taccgtttat aatgccattt   2153

taaggaaaac tacctgtatt taaaaataga aacatatcaa aaacaagaga aaagacacga   2213

gagagactgt ggcccatcaa cagacgttga tatgcaactg catggcatgt gctgttttgg   2273

ttgaaatcaa atacattccg tttgatggac agctgtcagc tttctcaaac tgtgaagatg   2333

acccaaagtt tccaactcct ttacagtatt accgggacta tgaactaaaa ggtgggactg   2393

aggatgtgta tagagtgagc gtgtgattgt agacagaggg gtgaagaagg aggaggaaga   2453

ggcagagaag gaggagacca gggctgggaa agaaacttct caagcaatga agactggact   2513

caggacattt ggggactgtg tacaatgagt tatggagact cgagggttca tgcagtcagt   2573

gttataccaa acccagtgtt aggagaaagg acacagcgta atggagaaag gggaagtagt   2633

agaattcaga aacaaaaatg cgcatctctt tctttgtttg tcaaatgaaa attttaactg   2693

gaattgtctg atatttaaga gaaacattca ggacctcatc attatgtggg ggctttgttc   2753

tccacagggt caggtaagag atggccttct tggctgccac aatcagaaat cacgcaggca   2813

ttttgggtag gcggcctcca gttttccttt gagtcgcgaa cgctgtgcgt ttgtcagaat   2873

gaagtataca agtcaatgtt tttcccccttt tttatataat aattatataa cttatgcatt  2933

tatacactac gagttgatct cggccagcca aagacacacg acaaaagaga caatcgatat   2993

aatgtggcct tgaattttaa ctctgtatgc ttaatgttta caatatgaag ttattagttc   3053

ttagaatgca gaatgtatgt aataaaataa gcttggccta gcatggcaaa tcagatttat   3113

acaggagtct gcatttgcac ttttttagt gactaaagtt gcttaatgaa aacatgtgct    3173
```

```
gaatgttgtg gattttgtgt tataatttac tttgtccagg aacttgtgca agggagagcc   3233
aaggaaatag gatgtttggc acccaaatgg cgtcagcctc tccaggtcct tcttgcctcc   3293
cctcctgtct tttatttcta gcccctttg gaacagaagg accccgggtt tcacattgga   3353
gcctccatat ttatgcctgg aatggaaaga ggcctatgaa gctggggttg tcattgagaa   3413
attctagttc agcacctggt cacaaatcac ccttaattcc tgctatgatt aaaatacatt   3473
tgttgaacag tgaacaagct accactcgta aggcaaactg tattattact ggcaaataaa   3533
gcgtcatgga tagctgcaat ttctcacttt acagaaacaa gggataacgt ctagatttgc   3593
tgcggggttt ctctttcagg agctctcact aggtagacag ctttagtcct gctacatcag   3653
agttacctgg gcactgtggc ttgggattca ctagccctga gcctgatgtt gctggctatc   3713
ccttgaagac aatgtttatt tccataatct agagtcagtt tccctgggca tcttttcttt   3773
gaatcacaaa tgctgccaac cttggtccag gtgaaggcaa ctcaaaaggt gaaaatacaa   3833
ggtgaccgtg cgaaggcgct agccgaaaca tcttagctga ataggtttct gaactggccc   3893
ttttcatagc tgtttcaggg cctgtttttt tcacgttgca gtccttttgc tatgattatg   3953
tgaagttgcc aaacctctgt gctgtggatg ttttggcagt gggctttgaa gtcggcagga   4013
cacgattacc aatgctcctg acaccccgtg tcatttggat tagacggagc ccaaccatcc   4073
atcattttgc agcagcctgg gaaggcccac aaagtgcccg tatctcctta gggaaaataa   4133
ataaatacaa tcatgaaagc tggcagttag gctgacccaa actgtgctaa tggaaaagat   4193
cagtcatttt tattttggaa tgcaaagtca agacacacct acattcttca tagaaataca   4253
catttacttg gataatcact cagttctctc ttcaagactg tctcatgagc aagatcataa   4313
aaacaagaca tgattatcat attcaatttt aacagatgtt ttccattaga tccctcaacc   4373
ctccaccccc agtccaggtt attagcaagt cttatgagca actgggataa ttttggataa   4433
catgataata ctgagttcct tcaaatacat aattcttaaa ttgtttcaaa atggcattaa   4493
ctctctgtta ctgttgtaat ctaattccaa agccccctcc aggtcatatt cataattgca   4553
tgaacctttt ctctctgttt gtccctgtct cttggcttgc cctgatgtat actcagactc   4613
ctgtacaatc ttactcctgc tggcaagaga tttgtcttct tttcttgtct tcaattggct   4673
ttcgggcctt gtatgtggta aaatcaccaa atcacagtca agactgtgtt tttgttccta   4733
gtttgatgcc cttatgtccc ggaggggttc acaaagtgct ttgtcaggac tgctgcagtt   4793
agaaggctca ctgcttctcc taagccttct gcacagatgt ggcacctgca acccaggagc   4853
aggagccgga ggagctgccc tctgacagca ggtgcagcag agatggctac agctcaggag   4913
ctgggaaggt gatggggcac agggaaagca cagatgttct gcagcgcccc aaagtgaccc   4973
attgcctgga gaaagagaag aaaatatttt ttaaaaagct agtttattta gcttctcatt   5033
aattcattca aataaagtcg tgaggtgact aattagagaa taaaaattac tttggactac   5093
tcaaaaatac accaaaaaaa a                                              5114
```

<210> SEQ ID NO 12
<211> LENGTH: 486
<212> TYPE: PRT
<213> ORGANISM: Homo sapiens

<400> SEQUENCE: 12

```
Met Ile Gln Thr Val Pro Asp Pro Ala Ala His Ile Lys Glu Ala Leu
1               5                   10                  15

Ser Val Val Ser Glu Asp Gln Ser Leu Phe Glu Cys Ala Tyr Gly Thr
            20                  25                  30
```

```
Pro His Leu Ala Lys Thr Glu Met Thr Ala Ser Ser Ser Ser Asp Tyr
        35                  40                  45

Gly Gln Thr Ser Lys Met Ser Pro Arg Val Pro Gln Gln Asp Trp Leu
    50                  55                  60

Ser Gln Pro Pro Ala Arg Val Thr Ile Lys Met Glu Cys Asn Pro Ser
65                  70                  75                  80

Gln Val Asn Gly Ser Arg Asn Ser Pro Asp Glu Cys Ser Val Ala Lys
                85                  90                  95

Gly Gly Lys Met Val Gly Ser Pro Asp Thr Val Gly Met Asn Tyr Gly
            100                 105                 110

Ser Tyr Met Glu Glu Lys His Met Pro Pro Pro Asn Met Thr Thr Asn
        115                 120                 125

Glu Arg Arg Val Ile Val Pro Ala Asp Pro Thr Leu Trp Ser Thr Asp
    130                 135                 140

His Val Arg Gln Trp Leu Glu Trp Ala Val Lys Glu Tyr Gly Leu Pro
145                 150                 155                 160

Asp Val Asn Ile Leu Leu Phe Gln Asn Ile Asp Gly Lys Glu Leu Cys
                165                 170                 175

Lys Met Thr Lys Asp Asp Phe Gln Arg Leu Thr Pro Ser Tyr Asn Ala
            180                 185                 190

Asp Ile Leu Leu Ser His Leu His Tyr Leu Arg Glu Thr Pro Leu Pro
        195                 200                 205

His Leu Thr Ser Asp Asp Val Asp Lys Ala Leu Gln Asn Ser Pro Arg
    210                 215                 220

Leu Met His Ala Arg Asn Thr Gly Gly Ala Ala Phe Ile Phe Pro Asn
225                 230                 235                 240

Thr Ser Val Tyr Pro Glu Ala Thr Gln Arg Ile Thr Thr Arg Pro Asp
                245                 250                 255

Leu Pro Tyr Glu Pro Pro Arg Arg Ser Ala Trp Thr Gly His Gly His
            260                 265                 270

Pro Thr Pro Gln Ser Lys Ala Ala Gln Pro Ser Pro Ser Thr Val Pro
        275                 280                 285

Lys Thr Glu Asp Gln Arg Pro Gln Leu Asp Pro Tyr Gln Ile Leu Gly
    290                 295                 300

Pro Thr Ser Ser Arg Leu Ala Asn Pro Gly Ser Gly Gln Ile Gln Leu
305                 310                 315                 320

Trp Gln Phe Leu Leu Glu Leu Leu Ser Asp Ser Ser Asn Ser Ser Cys
                325                 330                 335

Ile Thr Trp Glu Gly Thr Asn Gly Glu Phe Lys Met Thr Asp Pro Asp
            340                 345                 350

Glu Val Ala Arg Arg Trp Gly Glu Arg Lys Ser Lys Pro Asn Met Asn
        355                 360                 365

Tyr Asp Lys Leu Ser Arg Ala Leu Arg Tyr Tyr Tyr Asp Lys Asn Ile
    370                 375                 380

Met Thr Lys Val His Gly Lys Arg Tyr Ala Tyr Lys Phe Asp Phe His
385                 390                 395                 400

Gly Ile Ala Gln Ala Leu Gln Pro His Pro Pro Glu Ser Ser Leu Tyr
                405                 410                 415

Lys Tyr Pro Ser Asp Leu Pro Tyr Met Gly Ser Tyr His Ala His Pro
            420                 425                 430

Gln Lys Met Asn Phe Val Ala Pro His Pro Pro Ala Leu Pro Val Thr
        435                 440                 445
```

```
Ser Ser Ser Phe Phe Ala Ala Pro Asn Pro Tyr Trp Asn Ser Pro Thr
    450                 455                 460

Gly Gly Ile Tyr Pro Asn Thr Arg Leu Pro Thr Ser His Met Pro Ser
465                 470                 475                 480

His Leu Gly Thr Tyr Tyr
                485


<210> SEQ ID NO 13
<211> LENGTH: 4945
<212> TYPE: DNA
<213> ORGANISM: Homo sapiens
<220> FEATURE:
<221> NAME/KEY: CDS
<222> LOCATION: (125)..(1564)

<400> SEQUENCE: 13

ttcatttccc agacttagca caatctcatc cgctctaaac aacctcatca aaactacttt      60

ctggtcagag agaagcaata attattatta acatttatta acgatcaata aacttgatcg     120

catt atg gcc agc act att aag gaa gcc tta tca gtt gtg agt gag gac      169
     Met Ala Ser Thr Ile Lys Glu Ala Leu Ser Val Val Ser Glu Asp
     1               5                   10                  15

cag tcg ttg ttt gag tgt gcc tac gga acg cca cac ctg gct aag aca      217
Gln Ser Leu Phe Glu Cys Ala Tyr Gly Thr Pro His Leu Ala Lys Thr
                20                  25                  30

gag atg acc gcg tcc tcc tcc agc gac tat gga cag act tcc aag atg      265
Glu Met Thr Ala Ser Ser Ser Ser Asp Tyr Gly Gln Thr Ser Lys Met
            35                  40                  45

agc cca cgc gtc cct cag cag gat tgg ctg tct caa ccc cca gcc agg      313
Ser Pro Arg Val Pro Gln Gln Asp Trp Leu Ser Gln Pro Pro Ala Arg
        50                  55                  60

gtc acc atc aaa atg gaa tgt aac cct agc cag gtg aat ggc tca agg      361
Val Thr Ile Lys Met Glu Cys Asn Pro Ser Gln Val Asn Gly Ser Arg
    65                  70                  75

aac tct cct gat gaa tgc agt gtg gcc aaa ggc ggg aag atg gtg ggc      409
Asn Ser Pro Asp Glu Cys Ser Val Ala Lys Gly Gly Lys Met Val Gly
80                  85                  90                  95

agc cca gac acc gtt ggg atg aac tac ggc agc tac atg gag gag aag      457
Ser Pro Asp Thr Val Gly Met Asn Tyr Gly Ser Tyr Met Glu Glu Lys
                100                 105                 110

cac atg cca ccc cca aac atg acc acg aac gag cgc aga gtt atc gtg      505
His Met Pro Pro Pro Asn Met Thr Thr Asn Glu Arg Arg Val Ile Val
            115                 120                 125

cca gca gat cct acg cta tgg agt aca gac cat gtg cgg cag tgg ctg      553
Pro Ala Asp Pro Thr Leu Trp Ser Thr Asp His Val Arg Gln Trp Leu
        130                 135                 140

gag tgg gcg gtg aaa gaa tat ggc ctt cca gac gtc aac atc ttg tta      601
Glu Trp Ala Val Lys Glu Tyr Gly Leu Pro Asp Val Asn Ile Leu Leu
    145                 150                 155

ttc cag aac atc gat ggg aag gaa ctg tgc aag atg acc aag gac gac      649
Phe Gln Asn Ile Asp Gly Lys Glu Leu Cys Lys Met Thr Lys Asp Asp
160                 165                 170                 175

ttc cag agg ctc acc ccc agc tac aac gcc gac atc ctt ctc tca cat      697
Phe Gln Arg Leu Thr Pro Ser Tyr Asn Ala Asp Ile Leu Leu Ser His
                180                 185                 190

ctc cac tac ctc aga gag act cct ctt cca cat ttg act tca gat gat      745
Leu His Tyr Leu Arg Glu Thr Pro Leu Pro His Leu Thr Ser Asp Asp
            195                 200                 205

gtt gat aaa gcc tta caa aac tct cca cgg tta atg cat gct aga aac      793
Val Asp Lys Ala Leu Gln Asn Ser Pro Arg Leu Met His Ala Arg Asn
        210                 215                 220
```

-continued

```
aca ggg ggt gca gct ttt att ttc cca aat act tca gta tat cct gaa      841
Thr Gly Gly Ala Ala Phe Ile Phe Pro Asn Thr Ser Val Tyr Pro Glu
    225                 230                 235

gct acg caa aga att aca act agg cca gat tta cca tat gag ccc ccc      889
Ala Thr Gln Arg Ile Thr Thr Arg Pro Asp Leu Pro Tyr Glu Pro Pro
240                 245                 250                 255

agg aga tca gcc tgg acc ggt cac ggc cac ccc acg ccc cag tcg aaa      937
Arg Arg Ser Ala Trp Thr Gly His Gly His Pro Thr Pro Gln Ser Lys
                260                 265                 270

gct gct caa cca tct cct tcc aca gtg ccc aaa act gaa gac cag cgt      985
Ala Ala Gln Pro Ser Pro Ser Thr Val Pro Lys Thr Glu Asp Gln Arg
            275                 280                 285

cct cag tta gat cct tat cag att ctt gga cca aca agt agc cgc ctt     1033
Pro Gln Leu Asp Pro Tyr Gln Ile Leu Gly Pro Thr Ser Ser Arg Leu
        290                 295                 300

gca aat cca ggc agt ggc cag atc cag ctt tgg cag ttc ctc ctg gag     1081
Ala Asn Pro Gly Ser Gly Gln Ile Gln Leu Trp Gln Phe Leu Leu Glu
    305                 310                 315

ctc ctg tcg gac agc tcc aac tcc agc tgc atc acc tgg gaa ggc acc     1129
Leu Leu Ser Asp Ser Ser Asn Ser Ser Cys Ile Thr Trp Glu Gly Thr
320                 325                 330                 335

aac ggg gag ttc aag atg acg gat ccc gac gag gtg gcc cgg cgc tgg     1177
Asn Gly Glu Phe Lys Met Thr Asp Pro Asp Glu Val Ala Arg Arg Trp
                340                 345                 350

gga gag cgg aag agc aaa ccc aac atg aac tac gat aag ctc agc cgc     1225
Gly Glu Arg Lys Ser Lys Pro Asn Met Asn Tyr Asp Lys Leu Ser Arg
            355                 360                 365

gcc ctc cgt tac tac tat gac aag aac atc atg acc aag gtc cat ggg     1273
Ala Leu Arg Tyr Tyr Tyr Asp Lys Asn Ile Met Thr Lys Val His Gly
        370                 375                 380

aag cgc tac gcc tac aag ttc gac ttc cac ggg atc gcc cag gcc ctc     1321
Lys Arg Tyr Ala Tyr Lys Phe Asp Phe His Gly Ile Ala Gln Ala Leu
    385                 390                 395

cag ccc cac ccc ccg gag tca tct ctg tac aag tac ccc tca gac ctc     1369
Gln Pro His Pro Pro Glu Ser Ser Leu Tyr Lys Tyr Pro Ser Asp Leu
400                 405                 410                 415

ccg tac atg ggc tcc tat cac gcc cac cca cag aag atg aac ttt gtg     1417
Pro Tyr Met Gly Ser Tyr His Ala His Pro Gln Lys Met Asn Phe Val
                420                 425                 430

gcg ccc cac cct cca gcc ctc ccc gtg aca tct tcc agt ttt ttt gct     1465
Ala Pro His Pro Pro Ala Leu Pro Val Thr Ser Ser Ser Phe Phe Ala
            435                 440                 445

gcc cca aac cca tac tgg aat tca cca act ggg ggt ata tac ccc aac     1513
Ala Pro Asn Pro Tyr Trp Asn Ser Pro Thr Gly Gly Ile Tyr Pro Asn
        450                 455                 460

act agg ctc ccc acc agc cat atg cct tct cat ctg ggc act tac tac     1561
Thr Arg Leu Pro Thr Ser His Met Pro Ser His Leu Gly Thr Tyr Tyr
    465                 470                 475

taa agacctggcg gaggcttttc ccatcagcgt gcattcacca gcccatcgcc          1614

acaaactcta tcggagaaca tgaatcaaaa gtgcctcaag aggaatgaaa aaagctttac   1674

tggggctggg gaaggaagcc ggggaagaga tccaaagact cttgggaggg agttactgaa   1734

gtcttactac agaaatgagg aggatgctaa aaatgtcacg aatatggaca tatcatctgt   1794

ggactgacct tgtaaaagac agtgtatgta gaagcatgaa gtcttaagga caaagtgcca   1854

aagaaagtgg tcttaagaaa tgtataaact ttagagtaga gtttggaatc ccactaatgc   1914

aaactgggat gaaactaaag caatagaaac aacacagttt tgacctaaca taccgtttat   1974

aatgccattt taaggaaaac tacctgtatt taaaaataga aacatatcaa aaacaagaga   2034
```

```
aaagacacga gagagactgt ggcccatcaa cagacgttga tatgcaactg catggcatgt   2094
gctgttttgg ttgaaatcaa atacattccg tttgatggac agctgtcagc tttctcaaac   2154
tgtgaagatg acccaaagtt tccaactcct ttacagtatt accgggacta tgaactaaaa   2214
ggtgggactg aggatgtgta tagagtgagc gtgtgattgt agacagaggg gtgaagaagg   2274
aggaggaaga ggcagagaag gaggagacca gggctgggaa agaaacttct caagcaatga   2334
agactggact caggacattt ggggactgtg tacaatgagt tatggagact cgagggttca   2394
tgcagtcagt gttataccaa acccagtgtt aggagaaagg acacagcgta atggagaaag   2454
gggaagtagt agaattcaga aacaaaaatg cgcatctctt tctttgtttg tcaaatgaaa   2514
attttaactg gaattgtctg atatttaaga gaaacattca ggacctcatc attatgtggg   2574
ggctttgttc tccacagggt caggtaagag atggccttct tggctgccac aatcagaaat   2634
cacgcaggca ttttgggtag gcggcctcca gttttccttt gagtcgcgaa cgctgtgcgt   2694
ttgtcagaat gaagtataca agtcaatgtt tttccccctt tttatataat aattatataa   2754
cttatgcatt tatacactac gagttgatct cggccagcca aagacacacg acaaaagaga   2814
caatcgatat aatgtggcct tgaattttaa ctctgtatgc ttaatgttta caatatgaag   2874
ttattagttc ttagaatgca gaatgtatgt aataaaaataa gcttggccta gcatggcaaa   2934
tcagatttat acaggagtct gcatttgcac ttttttttagt gactaaagtt gcttaatgaa   2994
aacatgtgct gaatgttgtg gattttgtgt tataatttac tttgtccagg aacttgtgca   3054
agggagagcc aaggaaatag gatgtttggc acccaaatgg cgtcagcctc tccaggtcct   3114
tcttgcctcc cctcctgtct tttatttcta gcccctttttg gaacagaagg accccgggtt   3174
tcacattgga gcctccatat ttatgcctgg aatggaaaga ggcctatgaa gctggggttg   3234
tcattgagaa attctagttc agcacctggt cacaaatcac ccttaattcc tgctatgatt   3294
aaaatacatt tgttgaacag tgaacaagct accactcgta aggcaaactg tattattact   3354
ggcaaataaa gcgtcatgga tagctgcaat ttctcacttt acagaaacaa gggataacgt   3414
ctagatttgc tgcggggttt ctctttcagg agctctcact aggtagacag ctttagtcct   3474
gctacatcag agttacctgg gcactgtggc ttgggattca ctagccctga gcctgatgtt   3534
gctggctatc ccttgaagac aatgtttatt tccataatct agagtcagtt tccctgggca   3594
tcttttcttt gaatcacaaa tgctgccaac cttggtccag gtgaaggcaa ctcaaaaggt   3654
gaaaatacaa ggtgaccgtg cgaaggcgct agccgaaaca tcttagctga ataggtttct   3714
gaactggccc ttttcatagc tgtttcaggg cctgtttttt tcacgttgca gtccttttgc   3774
tatgattatg tgaagttgcc aaacctctgt gctgtggatg ttttggcagt gggctttgaa   3834
gtcggcagga cacgattacc aatgctcctg acaccccgtg tcatttggat tagacggagc   3894
ccaaccatcc atcattttgc agcagcctgg gaaggcccac aaagtgcccg tatctcctta   3954
gggaaaataa ataaatacaa tcatgaaagc tggcagttag gctgacccaa actgtgctaa   4014
tggaaaagat cagtcatttt tattttggaa tgcaaagtca agacacacct acattcttca   4074
tagaaataca catttacttg gataatcact cagttctctc ttcaagactg tctcatgagc   4134
aagatcataa aaacaagaca tgattatcat attcaatttt aacagatgtt ttccattaga   4194
tccctcaacc ctccaccccc agtccaggtt attagcaagt cttatgagca actgggataa   4254
ttttggataa catgataata ctgagttcct tcaaatacat aattcttaaa ttgtttcaaa   4314
atggcattaa ctctctgtta ctgttgtaat ctaattccaa agccccctcc aggtcatatt   4374
cataattgca tgaacctttt ctctctgttt gtccctgtct cttggcttgc cctgatgtat   4434
```

```
actcagactc ctgtacaatc ttactcctgc tggcaagaga tttgtcttct tttcttgtct   4494

tcaattggct ttcgggcctt gtatgtggta aaatcaccaa atcacagtca agactgtgtt   4554

tttgttccta gtttgatgcc cttatgtccc ggaggggttc acaaagtgct ttgtcaggac   4614

tgctgcagtt agaaggctca ctgcttctcc taagccttct gcacagatgt ggcacctgca   4674

acccaggagc aggagccgga ggagctgccc tctgacagca ggtgcagcag agatggctac   4734

agctcaggag ctgggaaggt gatggggcac agggaaagca cagatgttct gcagcgcccc   4794

aaagtgaccc attgcctgga gaaagagaag aaaatatttt ttaaaaagct agtttattta   4854

gcttctcatt aattcattca aataaagtcg tgaggtgact aattagagaa taaaaattac   4914

tttggactac tcaaaaatac accaaaaaaa a                                  4945
```

```
<210> SEQ ID NO 14
<211> LENGTH: 479
<212> TYPE: PRT
<213> ORGANISM: Homo sapiens

<400> SEQUENCE: 14

Met Ala Ser Thr Ile Lys Glu Ala Leu Ser Val Val Ser Glu Asp Gln
1               5                   10                  15

Ser Leu Phe Glu Cys Ala Tyr Gly Thr Pro His Leu Ala Lys Thr Glu
            20                  25                  30

Met Thr Ala Ser Ser Ser Ser Asp Tyr Gly Gln Thr Ser Lys Met Ser
        35                  40                  45

Pro Arg Val Pro Gln Gln Asp Trp Leu Ser Gln Pro Pro Ala Arg Val
    50                  55                  60

Thr Ile Lys Met Glu Cys Asn Pro Ser Gln Val Asn Gly Ser Arg Asn
65                  70                  75                  80

Ser Pro Asp Glu Cys Ser Val Ala Lys Gly Gly Lys Met Val Gly Ser
                85                  90                  95

Pro Asp Thr Val Gly Met Asn Tyr Gly Ser Tyr Met Glu Glu Lys His
            100                 105                 110

Met Pro Pro Pro Asn Met Thr Thr Asn Glu Arg Arg Val Ile Val Pro
        115                 120                 125

Ala Asp Pro Thr Leu Trp Ser Thr Asp His Val Arg Gln Trp Leu Glu
    130                 135                 140

Trp Ala Val Lys Glu Tyr Gly Leu Pro Asp Val Asn Ile Leu Leu Phe
145                 150                 155                 160

Gln Asn Ile Asp Gly Lys Glu Leu Cys Lys Met Thr Lys Asp Asp Phe
                165                 170                 175

Gln Arg Leu Thr Pro Ser Tyr Asn Ala Asp Ile Leu Leu Ser His Leu
            180                 185                 190

His Tyr Leu Arg Glu Thr Pro Leu Pro His Leu Thr Ser Asp Asp Val
        195                 200                 205

Asp Lys Ala Leu Gln Asn Ser Pro Arg Leu Met His Ala Arg Asn Thr
    210                 215                 220

Gly Gly Ala Ala Phe Ile Phe Pro Asn Thr Ser Val Tyr Pro Glu Ala
225                 230                 235                 240

Thr Gln Arg Ile Thr Thr Arg Pro Asp Leu Pro Tyr Glu Pro Pro Arg
                245                 250                 255

Arg Ser Ala Trp Thr Gly His Gly His Pro Thr Pro Gln Ser Lys Ala
            260                 265                 270

Ala Gln Pro Ser Pro Ser Thr Val Pro Lys Thr Glu Asp Gln Arg Pro
        275                 280                 285
```

```
Gln Leu Asp Pro Tyr Gln Ile Leu Gly Pro Thr Ser Ser Arg Leu Ala
    290                 295                 300

Asn Pro Gly Ser Gly Gln Ile Gln Leu Trp Gln Phe Leu Leu Glu Leu
305                 310                 315                 320

Leu Ser Asp Ser Ser Asn Ser Ser Cys Ile Thr Trp Glu Gly Thr Asn
                325                 330                 335

Gly Glu Phe Lys Met Thr Asp Pro Asp Glu Val Ala Arg Arg Trp Gly
            340                 345                 350

Glu Arg Lys Ser Lys Pro Asn Met Asn Tyr Asp Lys Leu Ser Arg Ala
        355                 360                 365

Leu Arg Tyr Tyr Tyr Asp Lys Asn Ile Met Thr Lys Val His Gly Lys
    370                 375                 380

Arg Tyr Ala Tyr Lys Phe Asp Phe His Gly Ile Ala Gln Ala Leu Gln
385                 390                 395                 400

Pro His Pro Pro Glu Ser Ser Leu Tyr Lys Tyr Pro Ser Asp Leu Pro
                405                 410                 415

Tyr Met Gly Ser Tyr His Ala His Pro Gln Lys Met Asn Phe Val Ala
            420                 425                 430

Pro His Pro Pro Ala Leu Pro Val Thr Ser Ser Ser Phe Phe Ala Ala
        435                 440                 445

Pro Asn Pro Tyr Trp Asn Ser Pro Thr Gly Gly Ile Tyr Pro Asn Thr
    450                 455                 460

Arg Leu Pro Thr Ser His Met Pro Ser His Leu Gly Thr Tyr Tyr
465                 470                 475


<210> SEQ ID NO 15
<211> LENGTH: 4727
<212> TYPE: DNA
<213> ORGANISM: Homo sapiens
<220> FEATURE:
<221> NAME/KEY: CDS
<222> LOCATION: (183)..(1346)

<400> SEQUENCE: 15

ttcatttccc agacttagca caatctcatc cgctctaaac aacctcatca aaactacttt      60

ctggtcagag agaagcaata attattatta acatttatta acgatcaata aacttgatcg     120

cattatggcc agcactatta aggaactctc ctgatgaatg cagtgtggcc aaaggcggga     180

ag atg gtg ggc agc cca gac acc gtt ggg atg aac tac ggc agc tac        227
   Met Val Gly Ser Pro Asp Thr Val Gly Met Asn Tyr Gly Ser Tyr
   1               5                   10                  15

atg gag gag aag cac atg cca ccc cca aac atg acc acg aac gag cgc       275
Met Glu Glu Lys His Met Pro Pro Pro Asn Met Thr Thr Asn Glu Arg
                20                  25                  30

aga gtt atc gtg cca gca gat cct acg cta tgg agt aca gac cat gtg       323
Arg Val Ile Val Pro Ala Asp Pro Thr Leu Trp Ser Thr Asp His Val
            35                  40                  45

cgg cag tgg ctg gag tgg gcg gtg aaa gaa tat ggc ctt cca gac gtc       371
Arg Gln Trp Leu Glu Trp Ala Val Lys Glu Tyr Gly Leu Pro Asp Val
        50                  55                  60

aac atc ttg tta ttc cag aac atc gat ggg aag gaa ctg tgc aag atg       419
Asn Ile Leu Leu Phe Gln Asn Ile Asp Gly Lys Glu Leu Cys Lys Met
    65                  70                  75

acc aag gac gac ttc cag agg ctc acc ccc agc tac aac gcc gac atc       467
Thr Lys Asp Asp Phe Gln Arg Leu Thr Pro Ser Tyr Asn Ala Asp Ile
80                  85                  90                  95
```

-continued

```
ctt ctc tca cat ctc cac tac ctc aga gag act cct ctt cca cat ttg      515
Leu Leu Ser His Leu His Tyr Leu Arg Glu Thr Pro Leu Pro His Leu
                100                 105                 110

act tca gat gat gtt gat aaa gcc tta caa aac tct cca cgg tta atg      563
Thr Ser Asp Asp Val Asp Lys Ala Leu Gln Asn Ser Pro Arg Leu Met
            115                 120                 125

cat gct aga aac aca ggg ggt gca gct ttt att ttc cca aat act tca      611
His Ala Arg Asn Thr Gly Gly Ala Ala Phe Ile Phe Pro Asn Thr Ser
        130                 135                 140

gta tat cct gaa gct acg caa aga att aca act agg cca gat tta cca      659
Val Tyr Pro Glu Ala Thr Gln Arg Ile Thr Thr Arg Pro Asp Leu Pro
    145                 150                 155

tat gag ccc ccc agg aga tca gcc tgg acc ggt cac ggc cac ccc acg      707
Tyr Glu Pro Pro Arg Arg Ser Ala Trp Thr Gly His Gly His Pro Thr
160                 165                 170                 175

ccc cag tcg aaa gct gct caa cca tct cct tcc aca gtg ccc aaa act      755
Pro Gln Ser Lys Ala Ala Gln Pro Ser Pro Ser Thr Val Pro Lys Thr
                180                 185                 190

gaa gac cag cgt cct cag tta gat cct tat cag att ctt gga cca aca      803
Glu Asp Gln Arg Pro Gln Leu Asp Pro Tyr Gln Ile Leu Gly Pro Thr
            195                 200                 205

agt agc cgc ctt gca aat cca ggc agt ggc cag atc cag ctt tgg cag      851
Ser Ser Arg Leu Ala Asn Pro Gly Ser Gly Gln Ile Gln Leu Trp Gln
        210                 215                 220

ttc ctc ctg gag ctc ctg tcg gac agc tcc aac tcc agc tgc atc acc      899
Phe Leu Leu Glu Leu Leu Ser Asp Ser Ser Asn Ser Ser Cys Ile Thr
    225                 230                 235

tgg gaa ggc acc aac ggg gag ttc aag atg acg gat ccc gac gag gtg      947
Trp Glu Gly Thr Asn Gly Glu Phe Lys Met Thr Asp Pro Asp Glu Val
240                 245                 250                 255

gcc cgg cgc tgg gga gag cgg aag agc aaa ccc aac atg aac tac gat      995
Ala Arg Arg Trp Gly Glu Arg Lys Ser Lys Pro Asn Met Asn Tyr Asp
                260                 265                 270

aag ctc agc cgc gcc ctc cgt tac tac tat gac aag aac atc atg acc     1043
Lys Leu Ser Arg Ala Leu Arg Tyr Tyr Tyr Asp Lys Asn Ile Met Thr
            275                 280                 285

aag gtc cat ggg aag cgc tac gcc tac aag ttc gac ttc cac ggg atc     1091
Lys Val His Gly Lys Arg Tyr Ala Tyr Lys Phe Asp Phe His Gly Ile
        290                 295                 300

gcc cag gcc ctc cag ccc cac ccc ccg gag tca tct ctg tac aag tac     1139
Ala Gln Ala Leu Gln Pro His Pro Pro Glu Ser Ser Leu Tyr Lys Tyr
    305                 310                 315

ccc tca gac ctc ccg tac atg ggc tcc tat cac gcc cac cca cag aag     1187
Pro Ser Asp Leu Pro Tyr Met Gly Ser Tyr His Ala His Pro Gln Lys
320                 325                 330                 335

atg aac ttt gtg gcg ccc cac cct cca gcc ctc ccc gtg aca tct tcc     1235
Met Asn Phe Val Ala Pro His Pro Pro Ala Leu Pro Val Thr Ser Ser
                340                 345                 350

agt ttt ttt gct gcc cca aac cca tac tgg aat tca cca act ggg ggt     1283
Ser Phe Phe Ala Ala Pro Asn Pro Tyr Trp Asn Ser Pro Thr Gly Gly
            355                 360                 365

ata tac ccc aac act agg ctc ccc acc agc cat atg cct tct cat ctg     1331
Ile Tyr Pro Asn Thr Arg Leu Pro Thr Ser His Met Pro Ser His Leu
        370                 375                 380

ggc act tac tac taa agacctggcg gaggcttttc ccatcagcgt gcattcacca     1386
Gly Thr Tyr Tyr
    385

gcccatcgcc acaaactcta tcggagaaca tgaatcaaaa gtgcctcaag aggaatgaaa   1446

aaagctttac tggggctggg gaaggaagcc ggggaagaga tccaaagact cttgggaggg   1506
```

```
agttactgaa gtcttactac agaaatgagg aggatgctaa aaatgtcacg aatatggaca   1566
tatcatctgt ggactgacct tgtaaaagac agtgtatgta gaagcatgaa gtcttaagga   1626
caaagtgcca aagaaagtgg tcttaagaaa tgtataaact ttagagtaga gtttggaatc   1686
ccactaatgc aaactgggat gaaactaaag caatagaaac aacacagttt tgacctaaca   1746
taccgtttat aatgccattt taaggaaaac tacctgtatt taaaaataga aacatatcaa   1806
aaacaagaga aaagacacga gagagactgt ggcccatcaa cagacgttga tatgcaactg   1866
catggcatgt gctgttttgg ttgaaatcaa atacattccg tttgatggac agctgtcagc   1926
tttctcaaac tgtgaagatg acccaaagtt tccaactcct ttacagtatt accgggacta   1986
tgaactaaaa ggtgggactg aggatgtgta tagagtgagc gtgtgattgt agacagaggg   2046
gtgaagaagg aggaggaaga ggcagagaag gaggagacca gggctgggaa agaaacttct   2106
caagcaatga agactggact caggacattt ggggactgtg tacaatgagt tatggagact   2166
cgagggttca tgcagtcagt gttataccaa acccagtgtt aggagaaagg acacagcgta   2226
atggagaaag gggaagtagt agaattcaga aacaaaaatg cgcatctctt tctttgtttg   2286
tcaaatgaaa attttaactg gaattgtctg atatttaaga gaaacattca ggacctcatc   2346
attatgtggg ggctttgttc tccacagggt caggtaagag atggccttct tggctgccac   2406
aatcagaaat cacgcaggca ttttgggtag gcggcctcca gttttccttt gagtcgcgaa   2466
cgctgtgcgt ttgtcagaat gaagtataca agtcaatgtt tttccccctt tttatataat   2526
aattatataa cttatgcatt tatacactac gagttgatct cggccagcca aagacacacg   2586
acaaaagaga caatcgatat aatgtggcct tgaattttaa ctctgtatgc ttaatgttta   2646
caatatgaag ttattagttc ttagaatgca gaatgtatgt aataaaataa gcttggccta   2706
gcatggcaaa tcagatttat acaggagtct gcatttgcac ttttttttagt gactaaagtt   2766
gcttaatgaa aacatgtgct gaatgttgtg gattttgtgt tataatttac tttgtccagg   2826
aacttgtgca agggagagcc aaggaaatag gatgtttggc acccaaatgg cgtcagcctc   2886
tccaggtcct tcttgcctcc cctcctgtct tttatttcta gccccttttg gaacagaagg   2946
accccgggtt tcacattgga gcctccatat ttatgcctgg aatggaaaga ggcctatgaa   3006
gctggggttg tcattgagaa attctagttc agcacctggt cacaaatcac ccttaattcc   3066
tgctatgatt aaaatacatt tgttgaacag tgaacaagct accactcgta aggcaaactg   3126
tattattact ggcaaataaa gcgtcatgga tagctgcaat ttctcacttt acagaaacaa   3186
gggataacgt ctagatttgc tgcggggttt ctctttcagg agctctcact aggtagacag   3246
ctttagtcct gctacatcag agttacctgg gcactgtggc ttgggattca ctagccctga   3306
gcctgatgtt gctggctatc ccttgaagac aatgtttatt tccataatct agagtcagtt   3366
tccctgggca tcttttcttt gaatcacaaa tgctgccaac cttggtccag gtgaaggcaa   3426
ctcaaaaggt gaaaatacaa ggtgaccgtg cgaaggcgct agccgaaaca tcttagctga   3486
ataggtttct gaactggccc ttttcatagc tgtttcaggg cctgtttttt tcacgttgca   3546
gtccttttgc tatgattatg tgaagttgcc aaacctctgt gctgtggatg ttttggcagt   3606
gggctttgaa gtcggcagga cacgattacc aatgctcctg acaccccgtg tcatttggat   3666
tagacggagc ccaaccatcc atcattttgc agcagcctgg gaaggcccac aaagtgcccg   3726
tatctcctta gggaaaataa ataaatacaa tcatgaaagc tggcagttag gctgacccaa   3786
actgtgctaa tggaaaagat cagtcatttt tattttggaa tgcaaagtca agacacacct   3846
acattcttca tagaaataca catttacttg gataatcact cagttctctc ttcaagactg   3906
```

```
tctcatgagc aagatcataa aaacaagaca tgattatcat attcaatttt aacagatgtt   3966

ttccattaga tccctcaacc ctccaccccc agtccaggtt attagcaagt cttatgagca   4026

actgggataa ttttggataa catgataata ctgagttcct tcaaatacat aattcttaaa   4086

ttgtttcaaa atggcattaa ctctctgtta ctgttgtaat ctaattccaa agccccctcc   4146

aggtcatatt cataattgca tgaacctttt ctctctgttt gtccctgtct cttggcttgc   4206

cctgatgtat actcagactc ctgtacaatc ttactcctgc tggcaagaga tttgtcttct   4266

tttcttgtct tcaattggct ttcgggcctt gtatgtggta aaatcaccaa atcacagtca   4326

agactgtgtt tttgttccta gtttgatgcc cttatgtccc ggaggggttc acaaagtgct   4386

ttgtcaggac tgctgcagtt agaaggctca ctgcttctcc taagccttct gcacagatgt   4446

ggcacctgca acccaggagc aggagccgga ggagctgccc tctgacagca ggtgcagcag   4506

agatggctac agctcaggag ctgggaaggt gatggggcac agggaaagca cagatgttct   4566

gcagcgcccc aaagtgaccc attgcctgga gaaagagaag aaaatatttt ttaaaaagct   4626

agtttattta gcttctcatt aattcattca aataaagtcg tgaggtgact aattagagaa   4686

taaaaattac tttggactac tcaaaaatac accaaaaaaa a                       4727
```

<210> SEQ ID NO 16
<211> LENGTH: 387
<212> TYPE: PRT
<213> ORGANISM: Homo sapiens

<400> SEQUENCE: 16

```
Met Val Gly Ser Pro Asp Thr Val Gly Met Asn Tyr Gly Ser Tyr Met
1               5                   10                  15

Glu Glu Lys His Met Pro Pro Pro Asn Met Thr Thr Asn Glu Arg Arg
            20                  25                  30

Val Ile Val Pro Ala Asp Pro Thr Leu Trp Ser Thr Asp His Val Arg
        35                  40                  45

Gln Trp Leu Glu Trp Ala Val Lys Glu Tyr Gly Leu Pro Asp Val Asn
    50                  55                  60

Ile Leu Leu Phe Gln Asn Ile Asp Gly Lys Glu Leu Cys Lys Met Thr
65                  70                  75                  80

Lys Asp Asp Phe Gln Arg Leu Thr Pro Ser Tyr Asn Ala Asp Ile Leu
                85                  90                  95

Leu Ser His Leu His Tyr Leu Arg Glu Thr Pro Leu Pro His Leu Thr
            100                 105                 110

Ser Asp Asp Val Asp Lys Ala Leu Gln Asn Ser Pro Arg Leu Met His
        115                 120                 125

Ala Arg Asn Thr Gly Gly Ala Ala Phe Ile Phe Pro Asn Thr Ser Val
    130                 135                 140

Tyr Pro Glu Ala Thr Gln Arg Ile Thr Thr Arg Pro Asp Leu Pro Tyr
145                 150                 155                 160

Glu Pro Pro Arg Arg Ser Ala Trp Thr Gly His Gly His Pro Thr Pro
                165                 170                 175

Gln Ser Lys Ala Ala Gln Pro Ser Pro Ser Thr Val Pro Lys Thr Glu
            180                 185                 190

Asp Gln Arg Pro Gln Leu Asp Pro Tyr Gln Ile Leu Gly Pro Thr Ser
        195                 200                 205

Ser Arg Leu Ala Asn Pro Gly Ser Gly Gln Ile Gln Leu Trp Gln Phe
    210                 215                 220
```

```
Leu Leu Glu Leu Leu Ser Asp Ser Ser Asn Ser Ser Cys Ile Thr Trp
225                 230                 235                 240

Glu Gly Thr Asn Gly Glu Phe Lys Met Thr Asp Pro Asp Glu Val Ala
                245                 250                 255

Arg Arg Trp Gly Glu Arg Lys Ser Lys Pro Asn Met Asn Tyr Asp Lys
            260                 265                 270

Leu Ser Arg Ala Leu Arg Tyr Tyr Tyr Asp Lys Asn Ile Met Thr Lys
        275                 280                 285

Val His Gly Lys Arg Tyr Ala Tyr Lys Phe Asp Phe His Gly Ile Ala
    290                 295                 300

Gln Ala Leu Gln Pro His Pro Pro Glu Ser Ser Leu Tyr Lys Tyr Pro
305                 310                 315                 320

Ser Asp Leu Pro Tyr Met Gly Ser Tyr His Ala His Pro Gln Lys Met
                325                 330                 335

Asn Phe Val Ala Pro His Pro Pro Ala Leu Pro Val Thr Ser Ser Ser
            340                 345                 350

Phe Phe Ala Ala Pro Asn Pro Tyr Trp Asn Ser Pro Thr Gly Gly Ile
        355                 360                 365

Tyr Pro Asn Thr Arg Leu Pro Thr Ser His Met Pro Ser His Leu Gly
    370                 375                 380

Thr Tyr Tyr
385


<210> SEQ ID NO 17
<211> LENGTH: 1490
<212> TYPE: DNA
<213> ORGANISM: Homo sapiens
<220> FEATURE:
<221> NAME/KEY: CDS
<222> LOCATION: (440)..(1468)

<400> SEQUENCE: 17

gcagataagc ccagcttagc ccagctgacc ccagaccctc tcccctcact ccccccatgt      60

cgcaggatcg agaccctgag gcagacagcc cgttcaccaa gcccccccgcc ccgcccccat    120

caccccgtaa acttctccca gcctccgccc tgccctcacc cagcccgctg ttccccaagc     180

ctcgctccaa gcccacgcca cccctgcagc agggcagccc cagaggccag cacctatccc     240

cgaggctggg gtcgaggctc ggccccgccc ctgcctctgc aacttgagcc tggctgcgac     300

ccctgctctg acgtctcgga aaattccccc ttgcccaggc ccttgggggga gggggtgcat    360

ggtatgaaat ggggctgaga cccccggctg ggggcagagg aacccgccag agaacattca     420

gaaggccttc atcgcatcc atg gac ctg tgg aac tgg gat gag gca tcc cca      472
                     Met Asp Leu Trp Asn Trp Asp Glu Ala Ser Pro
                     1               5                   10

cag gaa gtg cct cca ggg aac aag ctg gca ggg ctt gaa gga gcc aaa      520
Gln Glu Val Pro Pro Gly Asn Lys Leu Ala Gly Leu Glu Gly Ala Lys
            15                  20                  25

tta ggc ttc tgt ttc cct gat ctg gca ctc caa ggg gac acg ccg aca      568
Leu Gly Phe Cys Phe Pro Asp Leu Ala Leu Gln Gly Asp Thr Pro Thr
        30                  35                  40

gcg aca gca gag aca tgc tgg aaa ggt aca agc tca tcc ctg gca agc      616
Ala Thr Ala Glu Thr Cys Trp Lys Gly Thr Ser Ser Ser Leu Ala Ser
    45                  50                  55

ttc cca cag ctg gac tgg ggc tcc gcg tta ctg cac cca gaa gtt cca      664
Phe Pro Gln Leu Asp Trp Gly Ser Ala Leu Leu His Pro Glu Val Pro
60                  65                  70                  75
```

```
tgg ggg gcg gag ccc gac tct cag gct ctt ccg tgg tcc ggg gac tgg      712
Trp Gly Ala Glu Pro Asp Ser Gln Ala Leu Pro Trp Ser Gly Asp Trp
            80                  85                  90

aca gac atg gcg tgc aca gcc tgg gac tct tgg agc ggc gcc tcg cag      760
Thr Asp Met Ala Cys Thr Ala Trp Asp Ser Trp Ser Gly Ala Ser Gln
            95                  100                 105

acc ctg ggc ccc gcc cct ctc ggc ccg ggc ccc atc ccc gcc gcc ggc      808
Thr Leu Gly Pro Ala Pro Leu Gly Pro Gly Pro Ile Pro Ala Ala Gly
        110                 115                 120

tcc gaa ggc gcc gcg ggc cag aac tgc gtc ccc gtg gcg gga gag gcc      856
Ser Glu Gly Ala Ala Gly Gln Asn Cys Val Pro Val Ala Gly Glu Ala
    125                 130                 135

acc tcg tgg tcg cgc gcc cag gcc gcc ggg agc aac acc agc tgg gac      904
Thr Ser Trp Ser Arg Ala Gln Ala Ala Gly Ser Asn Thr Ser Trp Asp
140                 145                 150                 155

tgt tct gtg ggg ccc gac ggc gat acc tac tgg ggc agt ggc ctg ggc      952
Cys Ser Val Gly Pro Asp Gly Asp Thr Tyr Trp Gly Ser Gly Leu Gly
            160                 165                 170

ggg gag ccg cgc acg gac tgt acc att tcg tgg ggc ggg ccc gcg ggc     1000
Gly Glu Pro Arg Thr Asp Cys Thr Ile Ser Trp Gly Gly Pro Ala Gly
            175                 180                 185

ccg gac tgt acc acc tcc tgg aac ccg ggg ctg cat gcg ggt ggc acc     1048
Pro Asp Cys Thr Thr Ser Trp Asn Pro Gly Leu His Ala Gly Gly Thr
        190                 195                 200

acc tct ttg aag cgg tac cag agc tca gct ctc acc gtt tgc tcc gaa     1096
Thr Ser Leu Lys Arg Tyr Gln Ser Ser Ala Leu Thr Val Cys Ser Glu
    205                 210                 215

ccg agc ccg cag tcg gac cgt gcc agt ttg gct cga tgc ccc aaa act     1144
Pro Ser Pro Gln Ser Asp Arg Ala Ser Leu Ala Arg Cys Pro Lys Thr
220                 225                 230                 235

aac cac cga ggt ccc att cag ctg tgg cag ttc ctc ctg gag ctg ctc     1192
Asn His Arg Gly Pro Ile Gln Leu Trp Gln Phe Leu Leu Glu Leu Leu
            240                 245                 250

cac gac ggg gcg cgt agc agc tgc atc cgt tgg act ggc aac agc cgc     1240
His Asp Gly Ala Arg Ser Ser Cys Ile Arg Trp Thr Gly Asn Ser Arg
            255                 260                 265

gag ttc cag ctg tgc gac ccc aaa gag gtg gct cgg ctg tgg ggc gag     1288
Glu Phe Gln Leu Cys Asp Pro Lys Glu Val Ala Arg Leu Trp Gly Glu
        270                 275                 280

cgc aag aga aag ccg ggc atg aat tac gag aag ctg agc cgg ggc ctt     1336
Arg Lys Arg Lys Pro Gly Met Asn Tyr Glu Lys Leu Ser Arg Gly Leu
    285                 290                 295

cgc tac tac tat cgc cgc gac atc gtg cgc aag agc ggg ggg cga aag     1384
Arg Tyr Tyr Tyr Arg Arg Asp Ile Val Arg Lys Ser Gly Gly Arg Lys
300                 305                 310                 315

tac acg tac cgc ttc ggg ggc cgc gtg ccc agc cta gcc tat ccg gac     1432
Tyr Thr Tyr Arg Phe Gly Gly Arg Val Pro Ser Leu Ala Tyr Pro Asp
            320                 325                 330

tgt gcg gga ggc gga cgg gga gca gag aca caa taa aaattcccgg          1478
Cys Ala Gly Gly Gly Arg Gly Ala Glu Thr Gln
            335                 340

tcaaacctca aa                                                       1490
```

<210> SEQ ID NO 18
<211> LENGTH: 342
<212> TYPE: PRT
<213> ORGANISM: Homo sapiens

```
<400> SEQUENCE: 18

Met Asp Leu Trp Asn Trp Asp Glu Ala Ser Pro Gln Glu Val Pro Pro
1               5                   10                  15

Gly Asn Lys Leu Ala Gly Leu Glu Gly Ala Lys Leu Gly Phe Cys Phe
            20                  25                  30

Pro Asp Leu Ala Leu Gln Gly Asp Thr Pro Thr Ala Thr Ala Glu Thr
        35                  40                  45

Cys Trp Lys Gly Thr Ser Ser Ser Leu Ala Ser Phe Pro Gln Leu Asp
    50                  55                  60

Trp Gly Ser Ala Leu Leu His Pro Glu Val Pro Trp Gly Ala Glu Pro
65                  70                  75                  80

Asp Ser Gln Ala Leu Pro Trp Ser Gly Asp Trp Thr Asp Met Ala Cys
                85                  90                  95

Thr Ala Trp Asp Ser Trp Ser Gly Ala Ser Gln Thr Leu Gly Pro Ala
            100                 105                 110

Pro Leu Gly Pro Gly Pro Ile Pro Ala Ala Gly Ser Glu Gly Ala Ala
        115                 120                 125

Gly Gln Asn Cys Val Pro Val Ala Gly Glu Ala Thr Ser Trp Ser Arg
    130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Gly Glu Pro Arg Thr
                165                 170                 175

Asp Cys Thr Ile Ser Trp Gly Gly Pro Ala Gly Pro Asp Cys Thr Thr
            180                 185                 190

Ser Trp Asn Pro Gly Leu His Ala Gly Gly Thr Thr Ser Leu Lys Arg
        195                 200                 205

Tyr Gln Ser Ser Ala Leu Thr Val Cys Ser Glu Pro Ser Pro Gln Ser
    210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
            260                 265                 270

Asp Pro Lys Glu Val Ala Arg Leu Trp Gly Glu Arg Lys Arg Lys Pro
        275                 280                 285

Gly Met Asn Tyr Glu Lys Leu Ser Arg Gly Leu Arg Tyr Tyr Tyr Arg
    290                 295                 300

Arg Asp Ile Val Arg Lys Ser Gly Gly Arg Lys Tyr Thr Tyr Arg Phe
305                 310                 315                 320

Gly Gly Arg Val Pro Ser Leu Ala Tyr Pro Asp Cys Ala Gly Gly Gly
                325                 330                 335

Arg Gly Ala Glu Thr Gln
            340
```